(12) United States Patent
Fadli et al.

(10) Patent No.: US 8,034,124 B2
(45) Date of Patent: Oct. 11, 2011

(54) AZO DERIVATIVES CONTAINING A PYRAZOLINONE UNIT FOR DYEING KERATIN FIBRES

(75) Inventors: Aziz Fadli, Chelles (FR); Eric Metais, St. Leu la Forêt (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/666,123

(22) PCT Filed: Jun. 19, 2008

(86) PCT No.: PCT/EP2008/057819
§ 371 (c)(1), (2), (4) Date: Jul. 9, 2010

(87) PCT Pub. No.: WO2009/000753
PCT Pub. Date: Dec. 31, 2008

(65) Prior Publication Data
US 2010/0269269 A1  Oct. 28, 2010

Related U.S. Application Data

(60) Provisional application No. 60/929,601, filed on Jul. 5, 2007.

(30) Foreign Application Priority Data

Jun. 22, 2007  (FR) .................................... 07 55966

(51) Int. Cl.
*A61Q 5/10* (2006.01)
*C07D 231/00* (2006.01)
(52) U.S. Cl. ............ 8/405; 8/407; 8/409; 8/423; 8/437; 8/466; 8/573; 548/356.1
(58) Field of Classification Search .............. 8/405, 407, 8/409, 423, 437, 466, 573; 548/356.1
See application file for complete search history.

(56) References Cited

U.S. PATENT DOCUMENTS
4,731,094 A  3/1988 Kaiser et al.

FOREIGN PATENT DOCUMENTS
WO  WO 2006/024858 A1  3/2006
WO  WO 2006/082229  8/2006

OTHER PUBLICATIONS

STIC Search Report dated Nov. 9, 2010.*
Smaglyuk et al., "Antipyrine azo derivatives. Spectrophometric study and use in analysis." Zurnal Analiticeskoj Himii, Nauka, Moscow, Ru, vol. 30, No. 9, pp. 1680-1688 (1975).
A.A. Elbahnsawy et al., "Utility of 5-antipyrylazopyridin-2-thione: Synthesis of 5-antipyrylazothineno [2,3-*b*] Pyridines and 4-antipyrylazopyrido [3-4-*d*} Pyridazine Derivatives," Indian Journal of Heterocyclic Chemistry, vol. 10, pp. 135-140 (2000).
S. Senapati et al, "Synthesis and spectral characterization of palladium (II) and silver (I) complexes of antipyrine-azo-imadazoles," Indian Journal of Chemistry, vol. 45A, pp. 1153-1157 (2006).
International Search Report for PCT/EP2008/057819, dated Aug. 13, 2008.

* cited by examiner

*Primary Examiner* — Eisa Elhilo
(74) *Attorney, Agent, or Firm* — Finnegan, Henderson, Farabow, Garrett & Dunner, LLP

(57) ABSTRACT

The subject of the present invention is azo derivatives containing a pyrazolinone unit having the following formula (I), their mesomeric forms, their addition salts with an acid and their solvates and their use for dyeing keratin fibers. The subject of the invention is also a composition for dying keratin fibers comprising at least one azo derivative containing a pyrazolinone unit of formula (I) as direct dye, and the method for dyeing keratin fibers using this composition. The present invention makes it possible in particular to obtain chromatic colors that are resistant to the various attacks to which the hair may be subjected, in particular to shampoos and to light.

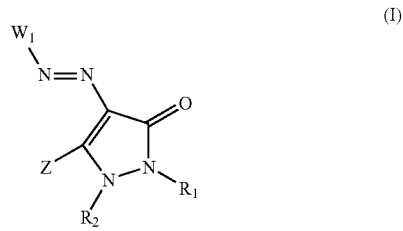

(I)

29 Claims, No Drawings

AZO DERIVATIVES CONTAINING A PYRAZOLINONE UNIT FOR DYEING KERATIN FIBRES

CROSS REFERENCE TO RELATED APPLICATIONS

This application is a National Phase application based on PCT/EP2008/057819 filed on Jun. 19, 2008, and claims the priority of French Application No. 0755966, filed on Jun. 22, 2007, and the benefit of U.S. Provisional Application No. 60/929,601, filed on Jul. 5, 2007, the content of all of which is incorporated herein by reference.

The subject of the present invention is azo derivatives containing a pyrazolinone unit, and their use as direct dyes for dyeing keratin fibres, and in particular human keratin fibres such as the hair.

It is known to dye keratin fibres with dye compositions containing direct dyes. These compounds are coloured and dyeing molecules having an affinity for the fibres. It is known, for example, to use direct dyes of the nitrobenzene type, anthraquinone dyes, nitropyridines, dyes of the azo, xanthene, acridine, azine or triarylmethane type.

Usually, these dyes are applied to the fibres, optionally in the presence of an oxidizing agent, if it is desired to obtain a simultaneous effect of lightening of the fibres. Once the exposure time has elapsed, the fibres are rinsed, optionally washed and dried.

The colours resulting from the use of direct dyes are often chromatic colours which are nevertheless temporary or semi-permanent because the nature of the interactions which link the direct dyes to the keratin fibre, and their desorption from the surface and/or the core of the fibre are responsible for their weak dyeing power and their relative poor fastness to washing or perspiration. These direct dyes are in addition generally sensitive to light because the resistance of the chromophore to photochemical attacks is low, which leads to fading of the colour of the hair over time. The sensitivity of these dyes to light depends on their uniform distribution or their distribution in the form of aggregates in and/or on the keratin fibre.

The aim of the present invention is to provide direct dyes not exhibiting the disadvantages of the existing direct dyes.

In particular, one of the aims of the present invention is to provide direct dyes which make it possible to obtain a colour with varied shades, which is intense, chromatic, aesthetic, not very selective and which withstands the various attacks to which the hair may be subjected such as shampoos, light, sweat and permanent deformations.

This aim is achieved with the present invention whose subject is azo derivatives containing a pyrazolinone unit having the following formula (I), their mesomeric forms, and their addition salts with an acid and their solvates:

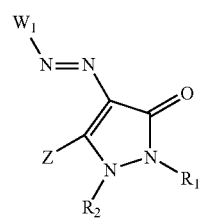

(I)

in which:
W$_1$ is attached to the azo functional group by means of a carbon atom and represents:
an aromatic heterocyclic group chosen from imidazole, benzimidazole, pyrazole, thiazole, benzothiazole, pyridine, pyrimidine, pyrazine, pyridazine rings optionally substituted with one or more substituents;
a cationic aromatic heterocyclic group chosen from imidazolium, benzimidazolium, pyrazolium, thiazolium, benzothiazolium, pyridinium, pyrimidinium, pyrazinium, pyridazinium rings substituted with one or more substituents, one of the substituents being carried by a nitrogen atom and combined with an organic or inorganic anion;
a phenyl radical substituted with a group chosen from an aromatic heterocyclic group chosen from imidazole, benzimidazole, pyrazole, thiazole, benzothiazole, pyridine, pyrimidinine, pyrazine and pyridazine rings optionally substituted with one or more substituents; a cationic aromatic heterocyclic group chosen from imidazolium, benzimidazolium, pyrazolium, thiazolium, benzothiazolium, pyridinium, pyrimidinium, pyrazinium and pyridazinium rings substituted with one or more substituents, one of the substituents being carried by a nitrogen atom and combined with an organic or inorganic anion; a radical NR'$_1$R'$_2$; a cationic group of the quaternary ammonium type having the following formula (II):

(II)

where:
R'$_1$ and R'$_2$, which are identical or different, represent a carboxyl radical, a C$_1$-C$_6$ alkyl radical optionally substituted with one or more radicals chosen from a hydroxyl, (C$_1$-C$_6$)alkoxy, cyano, amino, (C$_1$-C$_6$)(di)alkylamino, carboxyl, C$_1$-C$_6$ alkyl carboxylate, sulphonic, C$_1$-C$_6$ alkyl sulphonate and phenyl radical, a phenyl radical, a benzyl radical, a C$_1$-C$_6$ aminoalkyl radical, a (C$_1$-C$_6$)trialkyl-silane(C$_1$-C$_6$)alkyl radical or a C$_1$-C$_6$ aminoalkyl radical whose amine is protected by a (C$_1$-C$_6$)alkylcarbonyl, carbamyl, or (C$_1$-C$_6$)alkylsulphonyl radical; the radicals R'$_1$ and R'$_2$ may also form together, with the nitrogen atom to which they are attached, a 5- or 7-membered saturated ring which may contain one or more heteroatoms, such as for example a pyrrolidine ring, a piperidine ring, a piperazine ring or a morpholine ring, it being possible for the said ring to be unsubstituted or substituted with one or more radicals chosen from a halogen atom, a hydroxyl radical, a C$_1$-C$_6$ alkyl radical, a C$_1$-C$_6$ (poly)hydroxyalkyl radical, a nitro radical, a cyano radical, a C$_1$-C$_6$ cyanoalkyl radical, a C$_1$-C$_6$ alkoxy radical, a (C$_1$-C$_6$)tri-alkylsilane(C$_1$-C$_6$) alkyl radical, an amido radical, an aldehydo radical, a carboxyl radical, a C$_1$-C$_6$ ketoalkyl radical, a thio radical, a C$_1$-C$_6$ thioalkyl radical, a (C$_1$-C$_6$)alkylthio radical, an amino radical, an amino radical protected with a (C$_1$-C$_6$)alkylcarbonyl, carbamyl or (C$_1$-C$_6$) alkylsulphonyl radical;
R'$_3$ represents a carboxyl radical or a linear or branched C$_1$-C$_8$ alkyl radical optionally substituted with one or more radicals chosen from a hydroxyl, C$_1$-C$_2$ alkoxy, C$_1$-C$_4$ (poly)hydroxyalkoxy, amino, C$_1$-C$_2$ (di)alkylamino, carboxyl, C$_1$-C$_4$ alkyl carboxylate, sulphonic, C$_1$-C$_4$ alkyl sulphonate, optionally substituted phenyl and sulphonylamino radical;
A$_1^-$ is an organic or inorganic anion;
Z represents:
a linear or branched C$_1$-C$_4$ alkyl radical;
a radical NR$_3$R$_4$;

a radical $OR_5$;

$R_1$, $R_2$, $R_3$, $R_4$ and $R_5$, which are identical or different, represent:

a $C_1$-$C_6$ alkyl radical optionally substituted with one or more radicals chosen from a radical $OR_6$, a radical $NR_7R_8$, a carboxyl radical, a $C_1$-$C_4$ alkyl carboxylate radical, a sulphonic radical, a carboxamido radical $CONR_7R_8$, a sulphonamido radical $SO_2NR_7R_8$, a 5- or 6-membered heteroaryl or phenyl radical optionally substituted with one or more radicals chosen from a ($C_1$-$C_4$)alkyl, hydroxyl, $C_1$-$C_2$ alkoxy, amino, ($C_1$-$C_2$)(di)alkylamino or $C_1$-$C_4$ hydroxyalkyl radical;

a phenyl radical optionally substituted with one or more radicals chosen from a ($C_1$-$C_4$)alkyl, hydroxy($C_1$-$C_4$) alkyl, hydroxyl, $C_1$-$C_2$ alkoxy, amino and ($C_1$-$C_2$)(di)alkylamino radical;

a 5- or 6-membered heteroaryl radical optionally substituted with one or more radicals chosen from a ($C_1$-$C_4$) alkyl radical, a ($C_1$-$C_2$)alkoxy radical;

$R_3$, $R_4$ and $R_5$ may also represent a hydrogen atom;

$R_6$, $R_7$ and $R_8$, which are identical or different, represent a hydrogen atom; a linear or branched $C_1$-$C_4$ alkyl radical optionally substituted with one or more radicals chosen from a hydroxyl radical, a $C_1$-$C_2$ alkoxy radical, a carboxamido radical $CONR_9R_{10}$, a sulphonyl radical $SO_2R_9$, a phenyl radical optionally substituted with one or more radicals chosen from a ($C_1$-$C_4$)alkyl, hydroxyl, $C_1$-$C_2$ alkoxy, amino and ($C_1$-$C_2$)(di)alkylamino radical; a phenyl radical optionally substituted with one or more radicals chosen from a ($C_1$-$C_4$)alkyl radical, a hydroxyl radical, a $C_1$-$C_2$ alkoxy radical, an amino radical, a ($C_1$-$C_2$)(di)alkylamino radical;

$R_7$ and $R_8$, which are identical or different, may also represent a carboxamido radical $CONR_9R_{10}$; a sulphonyl radical $SO_2R_9$;

$R_9$ and $R_{10}$, which are identical or different, represent a hydrogen atom, a linear or branched $C_1$-$C_4$ alkyl radical optionally substituted with one or more radicals chosen from a hydroxyl radical, a $C_1$-$C_2$ alkoxy radical;

$R_1$ and $R_2$, on the one hand, and $R_3$ and $R_4$, on the other hand, may form with the nitrogen atoms to which they are attached a 5- to 7-membered saturated or unsaturated heterocycle whose carbon atoms may be replaced by an oxygen or nitrogen atom, optionally substituted with one or more radicals chosen from a halogen atom, a radical amino, ($C_1$-$C_4$)(di)alkylamino, (di)hydroxy($C_1$-$C_4$)alkylamino, hydroxyl, carboxyl, carboxamido, ($C_1$-$C_4$)(di)alkylcarboxamido, ($C_1$-$C_2$)alkoxy, $C_1$-$C_4$ alkyl optionally substituted with one or more radicals chosen from a hydroxyl, amino, ($C_1$-$C_4$)(di)alkylamino, $C_1$-$C_2$ alkoxy, carboxyl and sulphonyl radical;

with the exception of the following molecules:

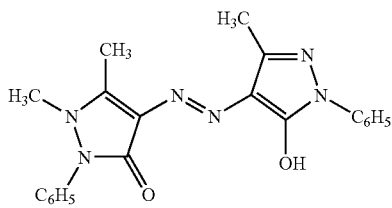

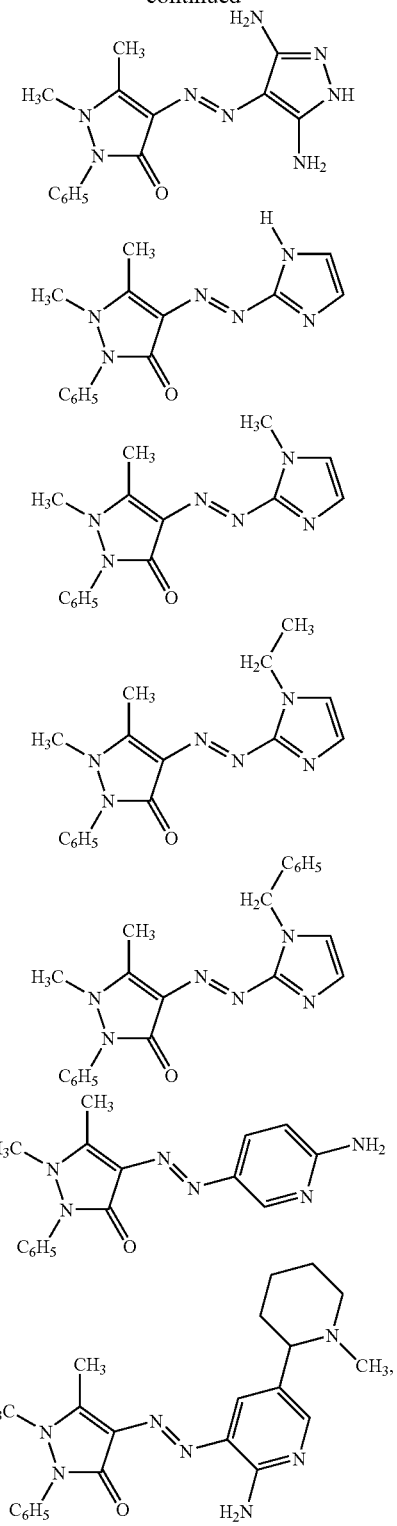

their mesomeric forms, their addition salts with an acid and their solvates.

The subject of the invention is also a composition for dyeing keratin fibres comprising at least one azo derivative containing a pyrazolinone unit of formula (I) as direct dye, and the method for dyeing keratin fibres using this composition.

The subject of the present invention is also a multicompartment device for carrying out the method in accordance with the invention.

The subject of the present invention is also the use, for dyeing keratin fibres, of an azo derivative containing a pyrazolinone unit of formula (I).

The present invention makes it possible in particular to obtain colours that are chromatic and resistant to the various attacks to which the hair may be subjected, in particular to shampoos and to light.

Unless otherwise stated, the limits of the ranges of values which are given in the context of the invention are included in these ranges.

In the context of the invention, unless otherwise stated, the alkyl radicals are linear or branched. An alkoxy radical is an alkyl-O— radical, the alkyl radical being as defined above.

A (poly)hydroxyalkyl radical is an alkyl radical which may be substituted with one or more hydroxyl radicals.

A (poly)hydroxyalkoxy radical is an alkoxy radical which may be substituted with one or more hydroxyl radicals.

A (di)alkylamino radical is an amino radical which may be substituted with one or two alkyl radicals.

A (di)alkylcarboxamido radical is a carboxamido radical which may be substituted with one or two alkyl radicals.

More particularly, in formula (I), the radicals $R_1$ and $R_2$, which are identical or different, are chosen from:
- a $C_1$-$C_4$ alkyl radical optionally substituted with one or more radicals chosen from a hydroxyl radical, a ($C_1$-$C_2$) alkoxy radical, an amino radical, a ($C_1$-$C_2$) (di)alkylamino radical;
- a phenyl radical optionally substituted with one or more radicals chosen from a $C_1$-$C_4$ alkyl radical and a $C_1$-$C_4$ hydroxyalkyl radical.

Preferably, the radicals $R_1$ and $R_2$, which are identical or different, are chosen from a methyl, ethyl, 2-hydroxyethyl, 3-hydroxypropyl, 2-hydroxypropyl and phenyl radical.

More preferably still, the radicals $R_1$ and $R_2$ are identical and are chosen from an ethyl and a phenyl radical.

According to another embodiment, the radicals $R_1$ and $R_2$-form together with the nitrogen atoms to which they are attached a saturated or unsaturated, optionally substituted 5- or 6-membered ring.

Preferably, the radicals $R_1$ and $R_2$ form together with the nitrogen atoms to which they are attached a pyrazolidine or pyridazolidine ring, optionally substituted with one or more radicals chosen from a $C_1$-$C_4$ alkyl, hydroxyl, ($C_1$-$C_2$)alkoxy, carboxyl, carboxamido, amino and ($C_1$-$C_2$)(di)alkylamino radical.

More advantageously still, the radicals $R_1$ and $R_2$ form together with the nitrogen atoms to which they are attached a pyrazolidine or pyridazolidine ring.

According to a particular embodiment of the invention, Z represents a radical $NR_3R_4$ or a radical $OR_5$.

As regards the radicals $R_3$, $R_4$ and $R_5$, the latter, which are identical or different, are more particularly chosen from a hydrogen atom; a $C_1$-$C_4$ alkyl radical optionally substituted with one or more radicals chosen from a hydroxyl, ($C_1$-$C_2$) alkoxy, amino, ($C_1$-$C_2$)(di) alkylamino, carboxyl and $C_1$-$C_4$ alkyl carboxylate radical; a phenyl radical optionally substituted with one or more radicals chosen from a hydroxyl, amino and ($C_1$-$C_2$)alkoxy radical.

Preferably, the radicals $R_3$, $R_4$ and $R_5$, which are identical or different, are chosen from a hydrogen atom, a radical methyl, ethyl, isopropyl, 2-hydroxyethyl, 3-hydroxypropyl, 2-hydroxypropyl, ethyl substituted with an ethyl carboxylate radical, ethyl substituted with a carboxyl radical. According to a particular embodiment, the radicals $R_3$, $R_4$ and $R_5$ represent a hydrogen atom.

According to another embodiment, the radicals $R_3$ and $R_4$ form together with the nitrogen atom to which they are attached a 5- to 7-membered ring chosen from the heterocycles pyrrolidine, piperidine, homopiperidine, piperazine and homopiperazine; it being possible for the said rings to be substituted with one or more radicals chosen from a radical hydroxyl, amino, ($C_1$-$C_2$)(di)alkylamino, ($C_1$-$C_2$)(di)hydroxyalkylamino, ($C_1$-$C_2$)(di)alkylcarboxamido, carboxyl, carboxamido, $C_1$-$C_4$ alkyl optionally substituted with one or more radicals chosen from a hydroxyl, amino and $C_1$-$C_2$ (di)alkylamino radical.

More particularly, the radicals $R_3$ and $R_4$ form together with the nitrogen atom to which they are attached a 5- to 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3, 4-dihydroxy-2-hydroxymethylpyrrolidine, 3-hydroxypyrrolidine, 3,4-dihydroxy-pyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine, N-(2-hydroxyethyl)-homopiperazine.

Preferably, the radicals $R_3$ and $R_4$ form together with the nitrogen atom to which they are attached a 5- to 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, 4-hydroxypiperidine, homopiperidine, homopiperazine, N-methylhomopiperazine, N-(2-hydroxyethyl)homopiperazine.

In accordance with an even more preferred embodiment of the invention, the radicals $R_3$ and $R_4$ form together with the nitrogen atom to which they are attached a 5-membered ring such as pyrrolidine, 3-hydroxypyrrolidine, 3-aminopyrrolidine, 3-dimethylaminopyrrolidine.

According to a particular embodiment of the invention, $W_1$ is an aromatic heterocyclic group of formula (III) below:

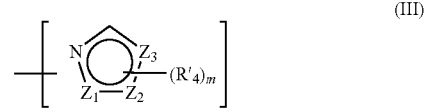

(III)

in which:
$Z_1$ represents C—C, C or N;
$Z_2$ represents N or C;
$Z_3$ represents S, N or C;
m is an integer between 0 and 5, preferably between 0 and 3;
$R'_4$ represent, independently of each other, a $C_1$-$C_8$ alkyl radical optionally substituted with one or more radicals chosen from a hydroxyl, $C_1$-$C_2$ alkoxy, $C_1$-$C_4$ (poly)hydroxyalkoxy, amino, $C_1$-$C_2$ (di)alkylamino, carboxyl, sulphonic, optionally substituted phenyl and sulphonylamino radical, a $C_1$-$C_4$ alkoxy radical, a chlorine atom, a nitro radical, a sulphonic radical; it being possible for two of the radicals $R'_4$ attached to two adjacent atoms to form with one another and with the atoms to which they are attached an optionally substituted, 5- or 6-membered aromatic or heteroaromatic ring.

Preferably, $W_1$ is chosen from the aromatic heterocyclic groups having the following formulae:

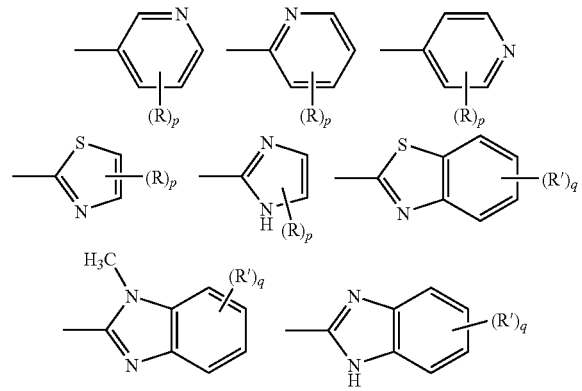

in which:
p is an integer between 0 and 2;
R represent, independently of each other, a $C_1$-$C_4$ alkyl radical, a $C_1$-$C_4$ alkoxy radical, a chlorine atom, a nitro radical, a sulphonic radical;
q is an integer equal to 0 or 1;
R' represent a $C_1$-$C_4$ alkoxy radical.

According to another particular embodiment of the invention, $W_1$ is a cationic aromatic heterocyclic group of formula (IV) below:

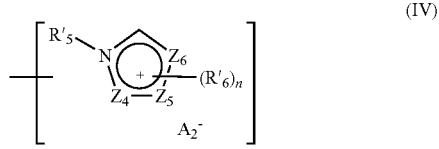

in which:
$Z_4$ represents C—C, C or N;
$Z_5$ represents N or C;
$Z_6$ represents S, N or C;
n is an integer between 0 and 5, preferably between 0 and 3;
$R'_5$ and $R'_6$, independently of each other, have the same definition as $R'_4$;
it being possible for two of the radicals $R'_5$ and $R'_6$ attached to two adjacent atoms to form with one another and with the atoms to which they are attached an optionally substituted, 5- or 6-membered aromatic or heteroaromatic ring;
$A_2^-$ is an organic or inorganic anion.

Preferably, $W_2$ is chosen from the aromatic heterocyclic groups having the following formulae:

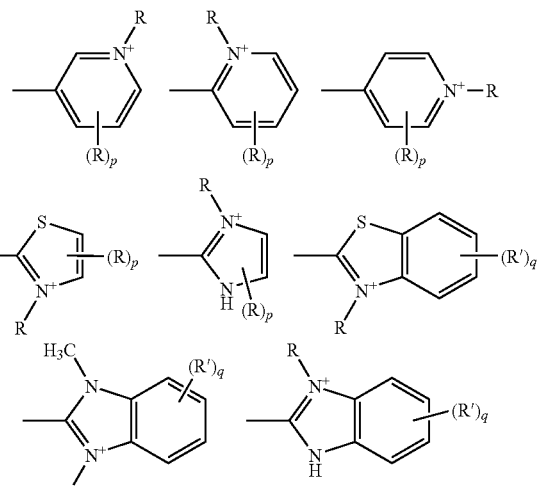

in which:
p is an integer between 0 and 2;
R represent, independently of each other, a $C_1$-$C_4$ alkyl radical, a $C_1$-$C_4$ alkoxy radical, a chlorine atom, a nitro radical, a sulphonic radical;
q is an integer equal to 0 or 1;
R' represent a $C_1$-$C_4$ alkoxy radical.

According to a particular embodiment, $W_1$ is a phenyl radical substituted with an aromatic heterocyclic group of formula (III) as defined above.

According to a particular embodiment, $W_1$ is a phenyl radical substituted with a cationic aromatic heterocyclic group of formula (IV) as defined above.

According to a particular embodiment, $W_1$ is a phenyl radical substituted with a radical $NR'_1R'_2$ and $R'_1$ and $R'_2$ represent, independently of each other, a carboxyl radical or a $C_1$-$C_4$ alkyl radical optionally substituted with one or more radicals chosen from a hydroxyl, $C_1$-$C_2$ alkoxy, amino, $C_1$-$C_2$ (di)alkylamino, carboxyl, $C_1$-$C_4$ alkyl carboxylate, sulphonic, $C_1$-$C_4$ alkyl sulphonate and phenyl radical. By way of examples, $R'_1$ and $R'_2$ represent, independently of each other, a methyl radical, an ethyl radical, a 2-hydroxyethyl radical, a carboxyl radical, a methyl radical substituted with a —COOH radical, or a —COOCH$_3$ radical or a —COOC$_2$H$_5$ radical, an ethyl radical substituted with a —COOH radical or a —COOCH$_3$ radical or a —COOC$_2$H$_5$ radical, an ethyl radical substituted with an —SO$_3$H radical or an —SO$_3$CH$_3$ radical or an —SO$_3$C$_2$H$_5$ radical.

According to a particular embodiment, $W_1$ is a phenyl radical substituted with a cationic group of the quaternary ammonium type of formula (II) and $R'_1$, $R'_2$ and $R'_3$ represent, independently of each other, a carboxyl radical or a $C_1$-$C_4$ alkyl radical optionally substituted with one or more radicals chosen from a hydroxyl, $C_1$-$C_2$ alkoxy, amino, $C_1$-$C_2$ (di)alkylamino, carboxyl, $C_1$-$C_4$ alkyl carboxylate, sulphonic, $C_1$-$C_4$ alkyl sulphonate and phenyl radical. By way of examples, $R'_1$, $R'_2$ and $R'_3$ represent, independently of each other, a methyl radical, an ethyl radical, a 2-hydroxyethyl radical, a carboxyl radical, a methyl radical substituted with a —COOH radical or a —COOCH$_3$ radical or a —COOC$_2$H$_5$ radical, or an ethyl radical substituted with a —COOH radical or a —COOCH$_3$ radical or a —COOC$_2$H$_5$ radical, an ethyl radical substituted with an —SO$_3$H radical or an —SO$_3$CH$_3$ radical or an —SO$_3$C$_2$H$_5$ radical.

According to a particular embodiment, $A_1^-$ and $A_2^-$ are chosen from a halide such as a chloride, bromide, fluoride, iodide; a hydroxide; a sulphate; a hydrogen sulphate; a ($C_1$-$C_6$) alkyl sulphate such as for example a methyl sulphate or an ethyl sulphate; an acetate; a tartrate; an oxalate; a ($C_1$-$C_6$) alkyl sulphonate such as a methyl sulphonate; an aryl sulphonate that is unsubstituted or substituted with a $C_1$-$C_4$ alkyl radical such as for example a 4-toluoyl sulphonate.

The compounds of formula (I) may be optionally salified by strong inorganic acids such as for example HCl, HBr, HI, $H_2SO_4$, $H_3PO_4$, or organic acids such as, for example, acetic, lactic, tartaric, citric, succinic, benzenesulphonic, para-toluenesulphonic, formic or methanesulphonic acid.

They may also be in the form of solvates, for example a hydrate or a solvate of a linear or branched alcohol such as ethanol or isopropanol.

By way of examples of compounds of formula (I), there may be mentioned the compounds presented below, $A_2^-$ being as defined above:

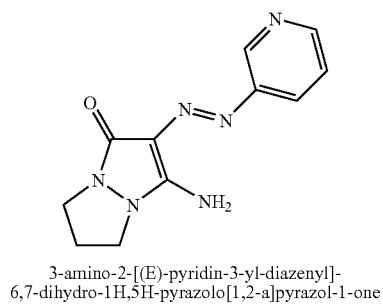

3-amino-2-[(E)-pyridin-3-yl-diazenyl]-
6,7-dihydro-1H,5H-pyrazolo[1,2-a]pyrazol-1-one

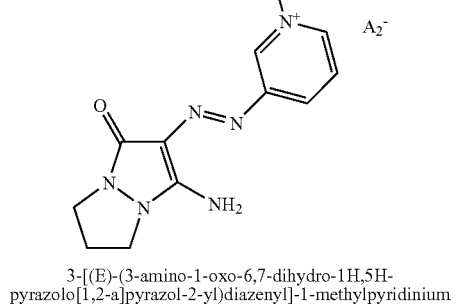

3-[(E)-(3-amino-1-oxo-6,7-dihydro-1H,5H-
pyrazolo[1,2-a]pyrazol-2-yl)diazenyl]-1-methylpyridinium

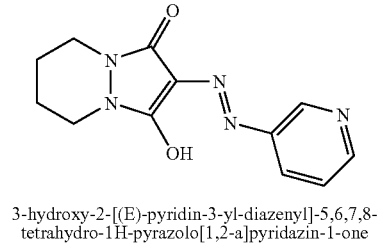

3-hydroxy-2-[(E)-pyridin-3-yl-diazenyl]-5,6,7,8-
tetrahydro-1H-pyrazolo[1,2-a]pyridazin-1-one

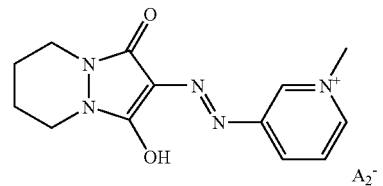

3-[(E)-(3-hydroxy-1-oxo-5,6,7,8-tetrahydro-
1H-pyrazolo[1,2-a]pyridazin-2-yl)-diazenyl]-1-methylpyridinium

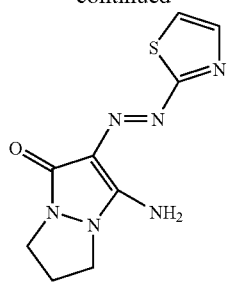

3-amino-2-[(E)-1,3-thiazol-2-yldiazenyl]-6,7-
dihydro-1H,5H-pyrazolo[1,2-a]pyrazol-1-one

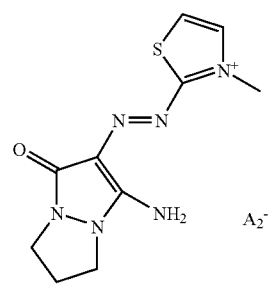

2-[(E)-(3-amino-1-oxo-6,7-dihydro-1H,5H-
pyrazolo[1,2-a]pyrazol-2-yl)diazenyl]-3-methyl-1,3-thiazol-3-ium

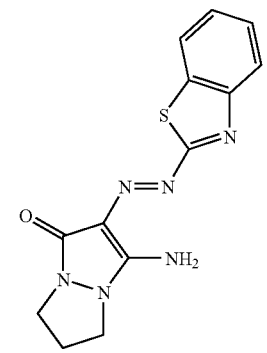

3-amino-2-[(E)-1,3-benzo-
thiazol-2-yldiazenyl]-6,7-
dihydro-1H,5H-pyrazolo[1,2-a]-
pyrazol-1-one

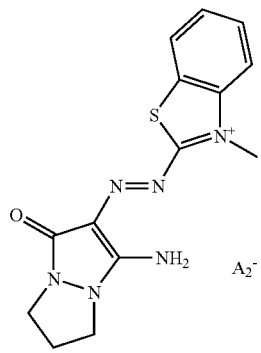

2-[(E)-(3-amino-1-oxo-6,7-
dihydro-1H,5H-pyrazolo[1,2-a]-
pyrazol-2-yl)diazenyl]-3-
methyl-1,3-benzothiazol-3-ium -continued

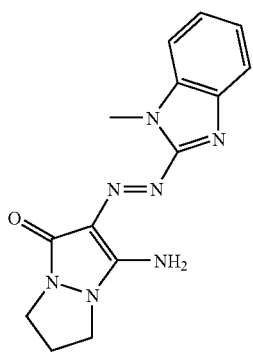

3-amino-2-[(E)-(1-methyl-1H-
benzimidazol-2-yl)diazenyl]-
6,7-dihydro-1H,5H-pyrazolo[1,2-
a]pyrazol-1-one

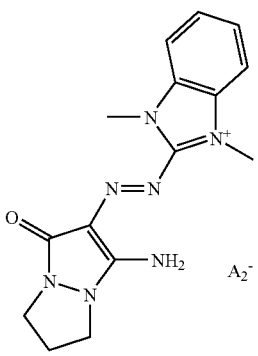

2-[(E)-(3-amino-1-oxo-6,7-
dihydro-1H,5H-pyrazolo[1,2-a]-
pyrazol-2-yl)diazenyl]-1,3-
dimethyl-1H-benzimidazol-3-ium

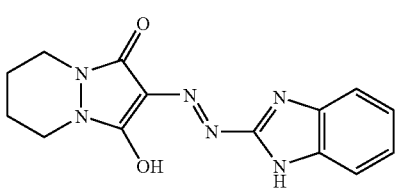

2-[(E)-1H-benzimidazol-2-yl-
diazenyl]-3-hydroxy-5,6,7,8-
tetrahydro-1H-pyrazolo[1,2-a]-
pyridazin-1-one

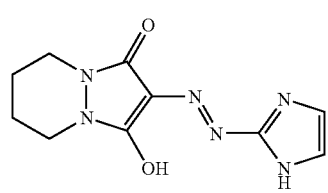

3-hydroxy-2-[(E)-1H-imidazol-
2-yldiazenyl]-5,6,7,8-tetra-
hydro-1H-pyrazolo[1,2-a]-
pyridazin-1-one -continued

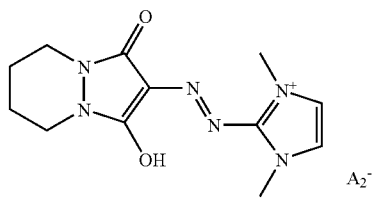

2-[(E)-(3-hydroxy-1-oxo-
5,6,7,8-tetrahydro-1H-pyrazolo-
[1,2-a]pyridazin-2-yl)-
diazenyl]-1,3-dimethyl-1H-
imidazol-3-ium

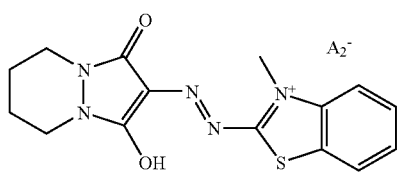

2-[(E)-(3-hydroxy-1-oxo-
5,6,7,8-tetrahydro-1H-pyrazolo-
[1,2-a]pyridazin-2-yl)-
diazenyl]-3-methyl-1,3-benzo-
thiazol-3-ium

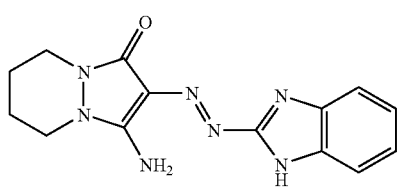

3-amino-2-[(E)-1H-benzimidazol-
2-yldiazenyl]-5,6,7,8-tetra-
hydro-1H-pyrazolo[1,2-a]-
pyridazin-1-one

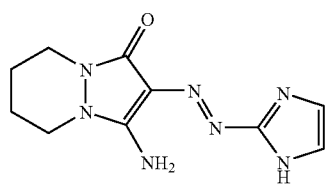

3-amino-2-[(E)-1H-imidazol-
2-yldiazenyl]-5,6,7,8-tetra-
hydro-1H-pyrazolo[1,2-a]-
pyridazin-1-one

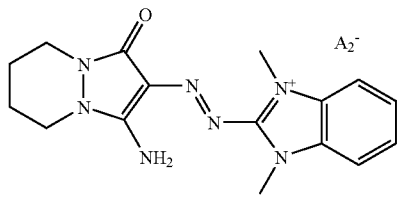

2-[(E)-(3-amino-1-oxo-5,6,7,8-
tetrahydro-1H-pyrazolo[1,2-a]-
pyridazin-2-yl)diazenyl]-1,3-
dimethyl-1H-3,1-benzimidazol-3-ium -continued

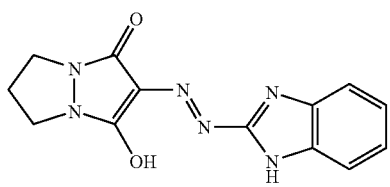

2-[(E)-1H-benzimidazol-2-yl-
diazenyl]-3-hydroxy-6,7-
dihydro-1H,5H-pyrazolo[1,2-a]-
pyrazol-1-one

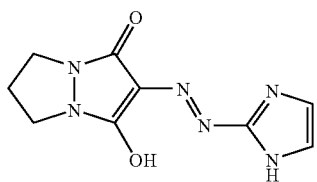

3-hydroxy-2-[(E)-1H-imidazol-2-
yldiazenyl]-6,7-dihydro-1H,5H-
pyrazolo[1,2-a]pyrazol-1-one

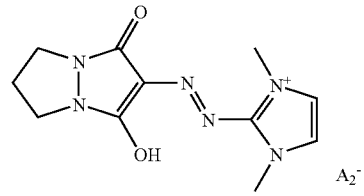

2-[(E)-(3-hydroxy-1-oxo-
6,7-dihydro-1H,5H-pyrazolo-[1,2-a]-
pyrazol-2-yl)-diazenyl]-1,3-
dimethyl-1H-imidazol-3-ium

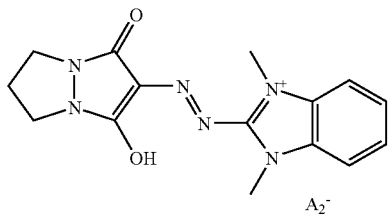

2-[(E)-(3-hydroxy-1-oxo-
6,7-dihydro-1H,5H-pyrazolo-[1,2-a]-
pyrazol-2-yl)-diazenyl]-1,3-
dimethyl-1H-3,1-benzimidazol-3-ium

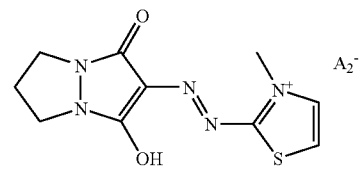

2-[(E)-(3-hydroxy-1-oxo-
6,7-dihydro-1H,5H-pyrazolo-[1,2-a]-
pyrazol-2-yl)-diazenyl]-3-
methyl-1,3-thiazol-3-ium

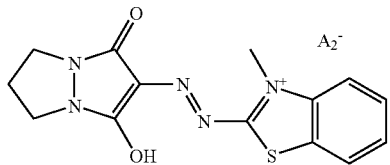

2-[(E)-(3-hydroxy-1-oxo-6,7-
dihydro-1H,5H-pyrazolo[1,2-a]-
pyrazol-2-yl)diazenyl]-3-
methyl-1,3-benzothiazol-3-ium

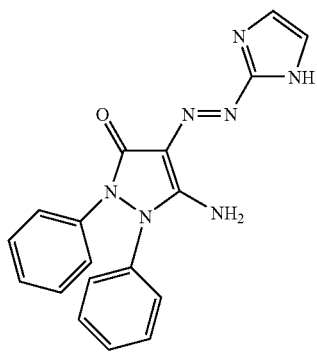

5-amino-4-[(E)-1H-imidazol-2-
yldiazenyl]-1,2-diphenyl-1,2-
dihydro-3H-pyrazol-3-one

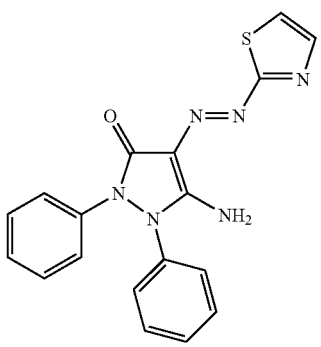

5-amino-1,2-diphenyl-4-[(E)-
1,3-thiazol-2-yldiazenyl]-1,2-
dihydro-3H-pyrazol-3-one

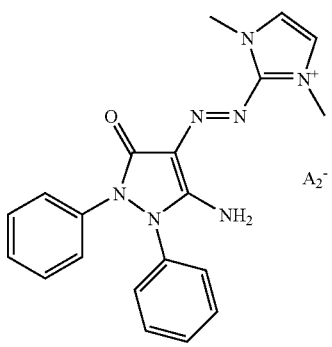

2-[(E)-(5-amino-3-oxo-1,2-
diphenyl-2,3-dihydro-1H-
pyrazol-4-yl)diazenyl]-1,3-
dimethyl-1H-imidazol-3-ium

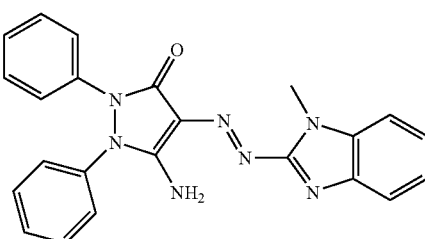

5-amino-4-[(E)-(1-methyl-1H-
benzimidazol-2-yl)diazenyl]-
1,2-diphenyl-1,2-dihydro-3H-
pyrazol-3-one -continued

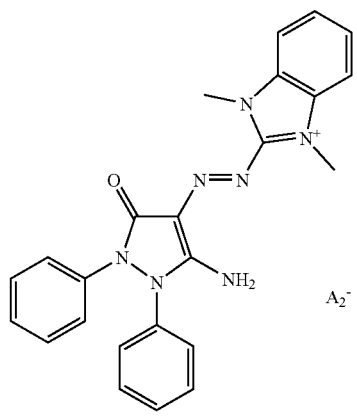

2-[(E)-(5-amino-3-oxo-1,2-
diphenyl-2,3-dihydro-1H-
pyrazol-4-yl)diazenyl]-1,3-
dimethyl-1H-benzimidazol-3-ium

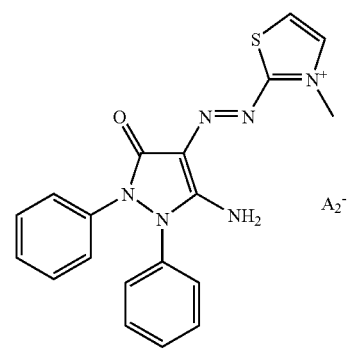

2-[(E)-(5-amino-3-oxo-1,2-
diphenyl-2,3-dihydro-1H-
pyrazol-4-yl)diazenyl]-3-
methyl-1,3-thiazol-3-ium

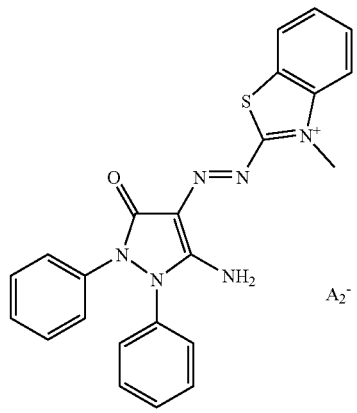

2-[(E)-(5-amino-3-oxo-1,2-
diphenyl-2,3-dihydro-1H-
pyrazol-4-yl)diazenyl]-3-
methyl-1,3-benzothiazol-3-ium -continued

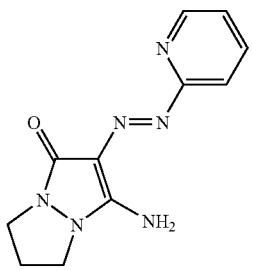

3-amino-2-[(E)-pyridin-2-yl-
diazenyl]-6,7-dihydro-1H,5H-
pyrazolo[1,2-a]pyrazol-1-one

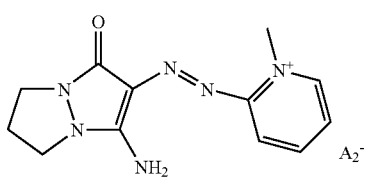

2-[(E)-(3-amino-1-oxo-6,7-
dihydro-1H,5H-pyrazolo[1,2-
a]pyrazol-2-yl)diazenyl]-1-
methylpyridinium

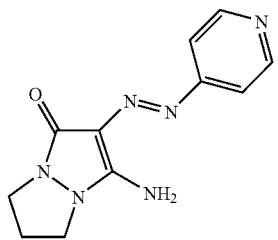

3-amino-2-[(E)-pyridin-4-yl-
diazenyl]-6,7-dihydro-1H,5H-
pyrazolo[1,2-a]pyrazol-1-one

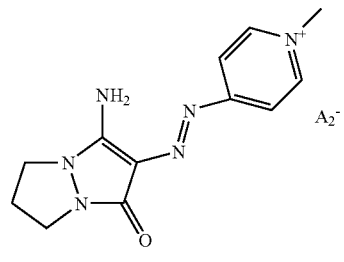

4-[(E)-(3-amino-1-oxo-6,7-
dihydro-1H,5H-pyrazolo[1,2-a]-
pyrazol-2-yl)diazenyl]-1-
methylpyridinium

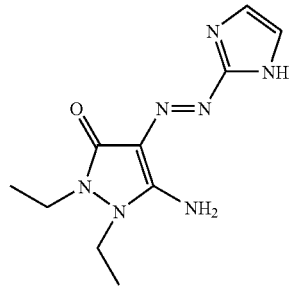

5-amino-4-[(E)-1H-imidazol-2-
yldiazenyl]-1,2-diethyl-1,2-
dihydro-3H-pyrazol-3-one -continued

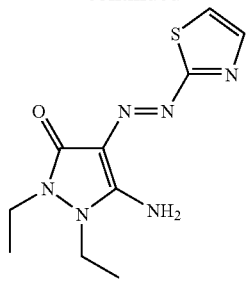

5-amino-1,2-diethyl-4-[(E)-1,3-
thiazol-2-yldiazenyl]-1,2-
dihydro-3H-pyrazol-3-one

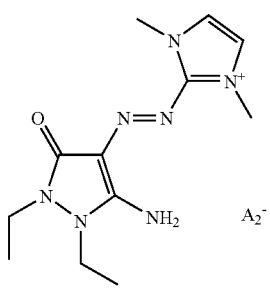

2-[(E)-(5-amino-3-oxo-1,2-
diethyl-2,3-dihydro-1H-pyrazol-
4-yl)diazenyl]-1,3-dimethyl-1H-
imidazol-3-ium

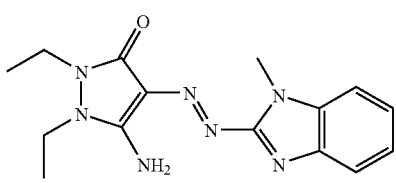

5-amino-4-[(E)-(1-methyl-1H-
benzimidazol-2-yl)diazenyl]-
1,2-diethyl-1,2-dihydro-3H-
pyrazol-3-one

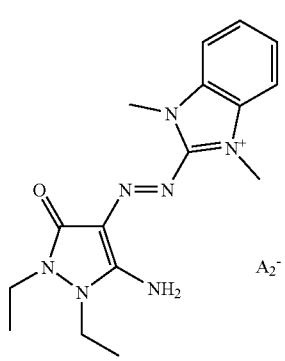

2-[(E)-(5-amino-3-oxo-1,2-
diethyl-2,3-dihydro-1H-pyrazol-
4-yl)diazenyl]-1,3-dimethyl-1H-
benzimidazol-3-ium -continued

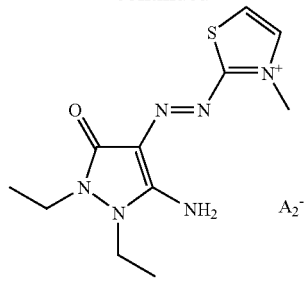

2-[(E)-(5-amino-3-oxo-1,2-
diethyl-2,3-dihydro-1H-pyrazol-
4-yl)diazenyl]-3-methyl-1,3-
thiazol-3-ium

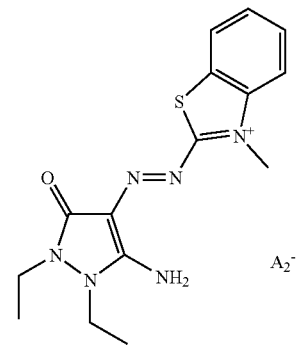

2-[(E)-(5-amino-3-oxo-1,2-
diethyl-2,3-dihydro-1H-pyrazol-
4-yl)diazenyl]-3-methyl-1,3-
benzothiazol-3-ium

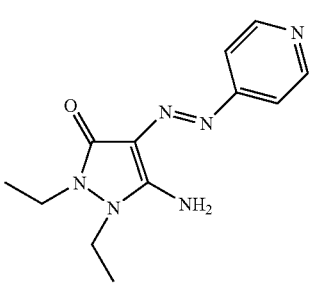

5-amino-1,2-diethyl-4-[(E)-
pyridin-4-yldiazenyl]-1,2-
dihydro-3H-pyrazol-3-one

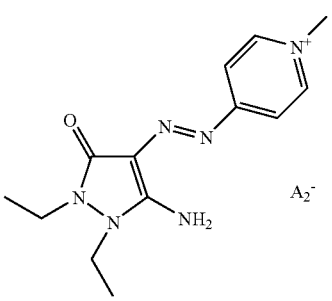

4-[(E)-(5-amino-1,2-diethyl-3-
oxo-2,3-dihydro-1H-pyrazol-4-
yl)diazenyl]-1-methylpyridinium -continued

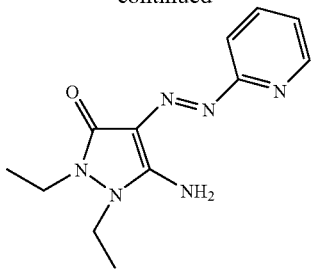

5-amino-1,2-diethyl-4-[(E)-
pyridin-2-yldiazenyl]-1,2-
dihydro-3H-pyrazol-3-one

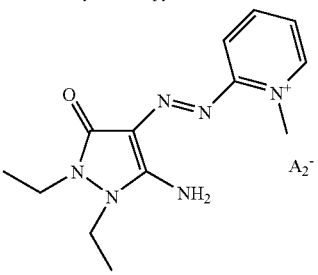

2-[(E)-(5-amino-1,2-diethyl-3-
oxo-2,3-dihydro-1H-pyrazol-4-
yl)diazenyl]-1-methylpyridinium

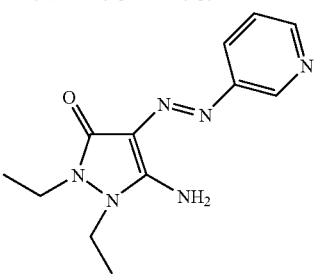

5-amino-1,2-diethyl-4-[(E)-
pyridin-3-yldiazenyl]-1,2-
dihydro-3H-pyrazol-3-one

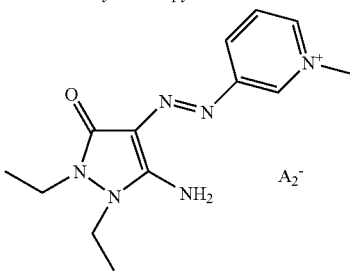

3-[(E)-(5-amino-1,2-diethyl-3-
oxo-2,3-dihydro-1H-pyrazol-4-
yl)diazenyl]-1-methylpyridinium

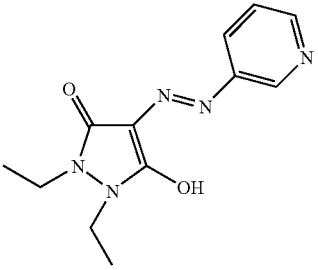

1,2-diethyl-5-hydroxy-4-[(E)-
pyridin-3-yldiazenyl]-1,2-
dihydro-3H-pyrazol-3-one -continued

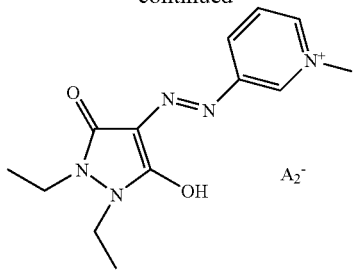

3-[(E)-(1,2-diethyl-5-hydroxy-
3-oxo-2,3-dihydro-1H-pyrazol-4-
yl)diazenyl]-1-methylpyridinium

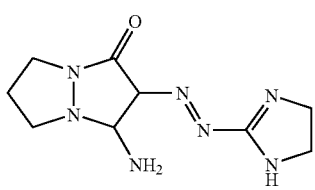

3-amino-2-[(E)-1H-imidazol-
2-yldiazenyl]-6,7-dihydro-
1H,5H-pyrazolo[1,2-a]pyrazol-1-one

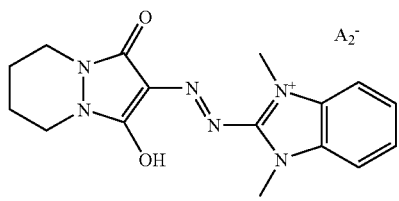

2-[(E)-(3-hydroxy-1-oxo-
5,6,7,8-tetrahydro-1H-pyrazolo-
[1,2-a]pyridazin-2-yl)-
diazenyl]-1,3-dimethyl-1H-
3,1-benzimidazol-3-ium

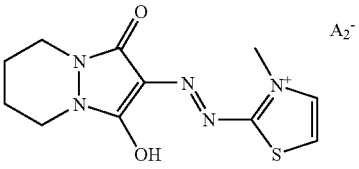

2-[(E)-(3-hydroxy-1-oxo-
5,6,7,8-tetrahydro-1H-pyrazolo-
[1,2-a]pyridazin-2-yl)-
diazenyl]-3-methyl-1,3-thiazol-
3-ium

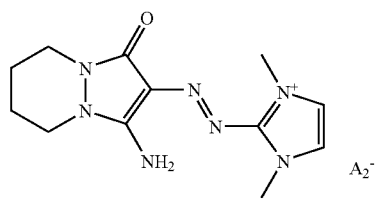

2-[(E)-(3-amino-1-oxo-5,6,7,8-
tetrahydro-1H-pyrazolo[1,2-a]-
pyridazin-2-yl)diazenyl]-1,3-
dimethyl-1H-imidazol-3-ium -continued

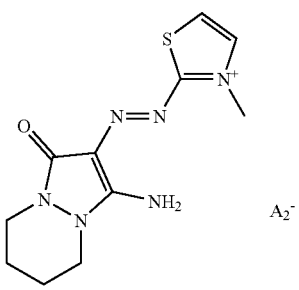

2-[(E)-(3-amino-1-oxo-5,6,7,8-
tetrahydro-1H-pyrazolo[1,2-a]-
pyridazin-2-yl)diazenyl]-
3-methyl-1,3-thiazol-3-ium

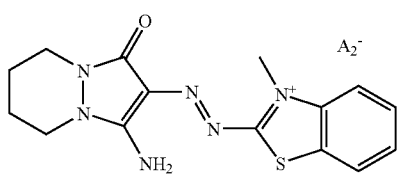

2-[(E)-(3-amino-1-oxo-5,6,7,8-
tetrahydro-1H-pyrazolo[1,2-a]-
pyridazin-2-yl)diazenyl]-3-
methyl-1,3-benzothiazol-3-ium Preferably, the azo derivatives containing a pyrazolinone unit of formula (I) are chosen from the following compounds:

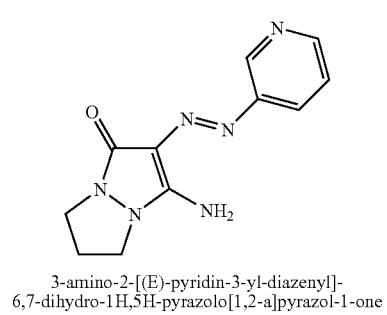

3-amino-2-[(E)-pyridin-3-yl-diazenyl]-
6,7-dihydro-1H,5H-pyrazolo[1,2-a]pyrazol-1-one

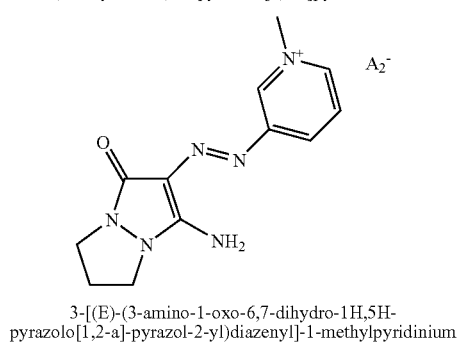

3-[(E)-(3-amino-1-oxo-6,7-dihydro-1H,5H-
pyrazolo[1,2-a]-pyrazol-2-yl)diazenyl]-1-methylpyridinium

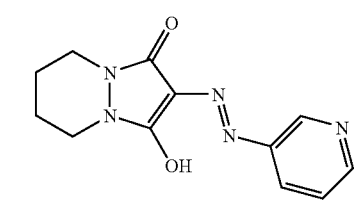

3-hydroxy-2-[(E)-pyridin-3-yl-diazenyl]-5,6,7,8-
tetrahydro-1H-pyrazolo[1,2-a]pyridazin-1-one

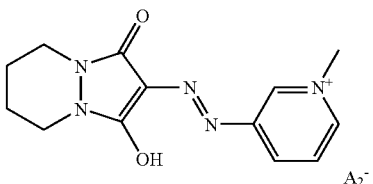

3-[(E)-(3-hydroxy-1-oxo-5,6,7,8-tetrahydro-
1H-pyrazolo-[1,2-a]pyridazin-2-yl)-diazenyl]-1-methylpyridinium

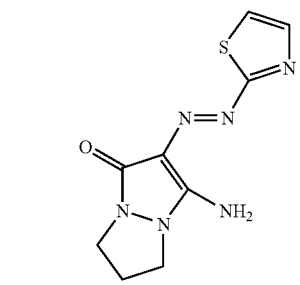

3-amino-2-[(E)-1,3-thiazol-2-yldiazenyl]-6,7-
dihydro-1H,5H-pyrazolo[1,2-a]pyrazol-1-one

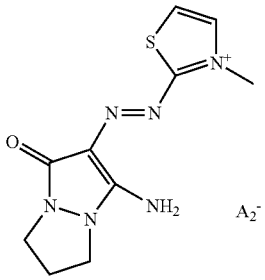

2-[(E)-(3-amino-1-oxo-6,7-dihydro-1H,5H-
pyrazolo[1,2-a]-pyrazol-2-yl)diazenyl]-3-methyl-1,3-thiazol-3-ium

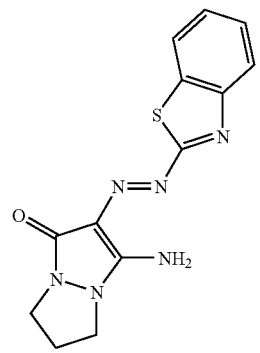

3-amino-2-[(E)-1,3-benzo-
thiazol-2-yldiazenyl]-6,7-
dihydro-1H,5H-pyrazolo[1,2-a]-
pyrazol-1-one -continued

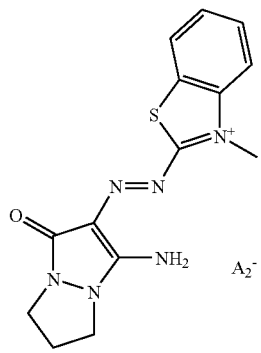

2-[(E)-(3-amino-1-oxo-6,7-
dihydro-1H,5H-pyrazolo[1,2-a]-
pyrazol-2-yl)diazenyl]-3-
methyl-1,3-benzothiazol-3-ium

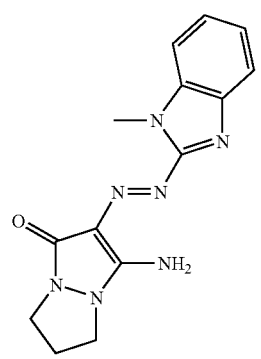

3-amino-2-[(E)-1-methyl-1H-
benzimidazol-2-yl)diazenyl]-
6,7-dihydro-1H,5H-pyrazolo-
[1,2-a]pyrazol-1-one

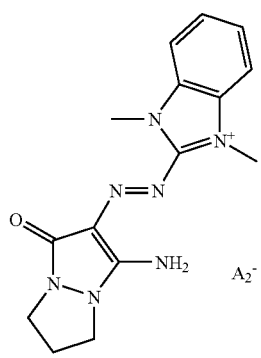

2-[(E)-(3-amino-1-oxo-6,7-
dihydro-1H,5H-pyrazolo[1,2-a]-
pyrazol-2-yl)diazenyl]-1,3-
dimethyl-1H-benzimidazol-3-ium

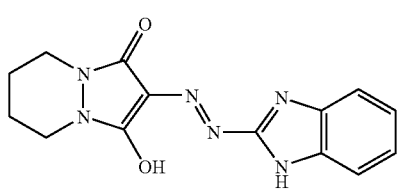

2-[(E)-1H-benzimidazol-2-yl-
diazenyl]-3-hydroxy-5,6,7,8-
tetrahydro-1H-pyrazolo[1,2-a]-
pyridazin-1-one -continued

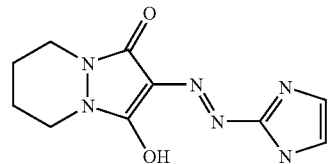

3-hydroxy-2-[(E)-1H-imidazol-
2-yldiazenyl]-5,6,7,8-tetra-
hydro-1H-pyrazolo[1,2-a]-
pyridazin-1-one

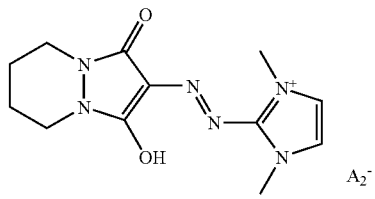

2-[(E)-(3-hydroxy-1-oxo-
5,6,7,8-tetrahydro-1H-pyrazolo-
[1,2-a]pyridazin-2-yl)-
diazenyl]-1,3-dimethyl-1H-
imidazol-3-ium

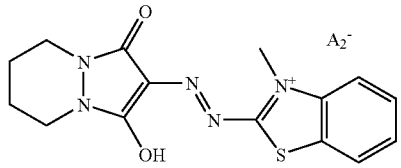

2-[(E)-(3-hydroxy-1-oxo-
5,6,7,8-tetrahydro-1H-pyrazolo-
[1,2-a]pyridazin-2-yl)-
diazenyl]-3-methyl-1,3-benzo-
thiazol-3-ium

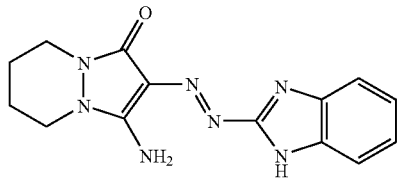

3-amino-2-[(E)-1H-benzimidazol-
2-yldiazenyl]-5,6,7,8-tetra-
hydro-1H-pyrazolo[1,2-a]-
pyridazin-1-one

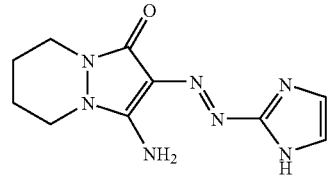

3-amino-2-[(E)-1H-imidazol-
2-yldiazenyl]-5,6,7,8-
tetrahydro-1H-pyrazolo[1,2-
a]pyridazin-1-one

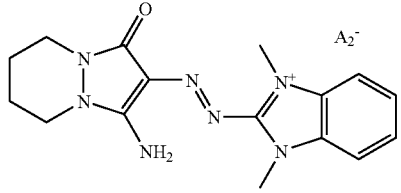

2-[(E)-(3-amino-1-oxo-5,6,7,8-
tetrahydro-1H-pyrazolo[1,2-a]-
pyridazin-2-yl)diazenyl]-1,3-
dimethyl-1H-3,1-benzimidazol-3-ium

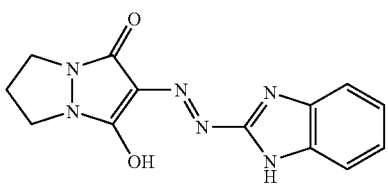

2-[(E)-1H-benzimidazol-2-yl-
diazenyl]-3-hydroxy-6,7-
dihydro-1H,5H-pyrazolo[1,2-a-
pyrazol-1-one

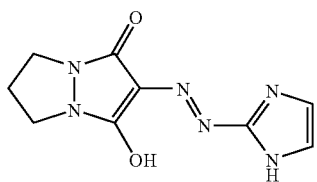

3-hydroxy-2-[(E)-1H-imidazol-2-
yldiazenyl]-6,7-dihydro-1H,5H-
pyrazolo[1,2-a]pyrazol-1-one

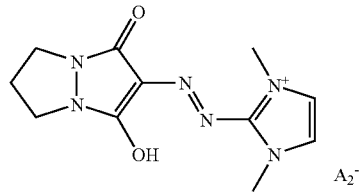

2-[(E)-(3-hydroxy-1-oxo-
6,7-dihydro-1H,5H-pyrazolo-[1,2-a]-
pyrazol-2-yl)-diazenyl]-1,3-
dimethyl-1H-imidazol-3-ium

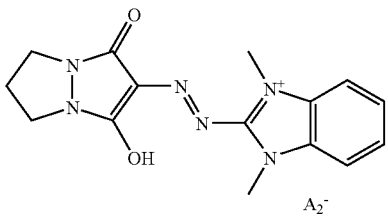

2-[(E)-(3-hydroxy-1-oxo-
6,7-dihydro-1H,5H-pyrazolo[1,2-a]-
pyrazol-2-yl)-diazenyl]-1,3-
dimethyl-1H-3,1-benzimidazol-3-ium

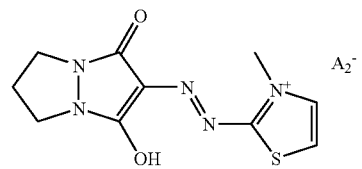

2-[(E)-(3-hydroxy-1-oxo-
6,7-dihydro-1H,5H-pyrazolo-[1,2-a]-
pyrazol-2-yl)-diazenyl]-3-
methyl-1,3-thiazol-3-ium

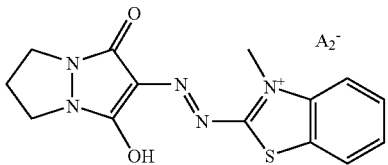

2-[(E)-(3-hydroxy-1-oxo-6,7-
dihydro-1H,5H-pyrazolo[1,2-a]-
pyrazol-2-yl)diazenyl]-3-
methyl-1,3-benzothiazol-3-ium

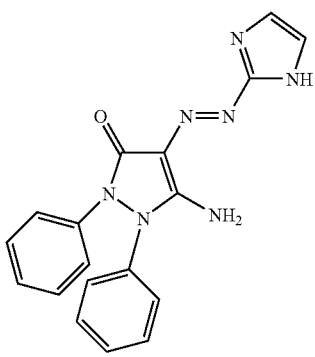

5-amino-4-[(E)-1H-imidazol-2-
yldiazenyl]-1,2-diphenyl-1,2-
dihydro-3H-pyrazol-3-one

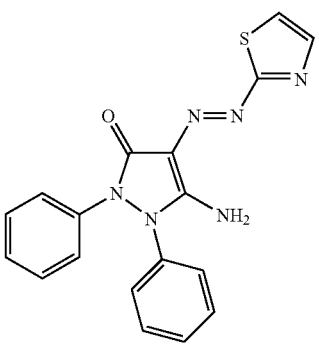

5-amino-1,2-diphenyl-4-[(E)-
1,3-thiazol-2-yldiazenyl]-1,2-
dihydro-3H-pyrazol-3-one

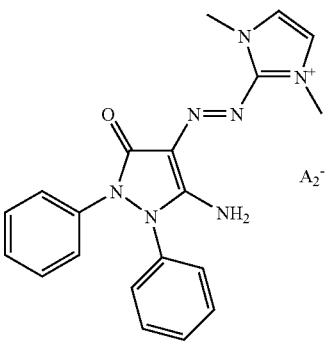

2-[(E)-(5-amino-3-oxo-1,2-
diphenyl-2,3-dihydro-1H-
pyrazol-4-yl)diazenyl]-
1,3-dimethyl-1H-imidazol-3-ium

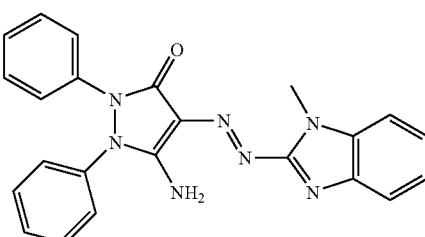

5-amino-4-[(E)-(1-methyl-1H-
benzimidazol-2-yl)diazenyl]-
1,2-diphenyl-1,2-dihydro-3H-
pyrazol-3-one

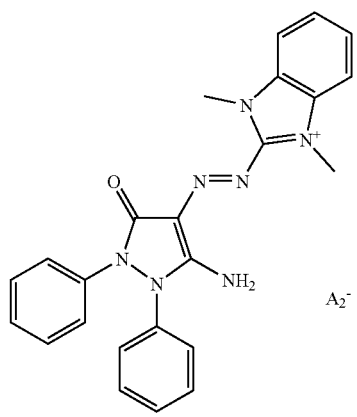

2-[(E)-(5-amino-3-oxo-1,2-
diphenyl-2,3-dihydro-1H-
pyrazol-4-yl)diazenyl]-1,3-
dimethyl-1H-benzimidazol-3-ium

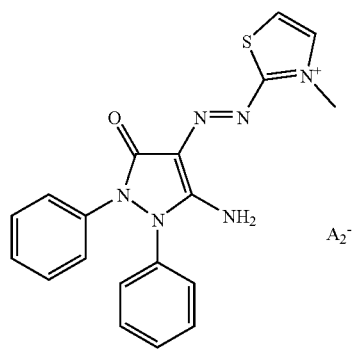

2-[(E)-(5-amino-3-oxo-1,2-
diphenyl-2,3-dihydro-1H-
pyrazol-4-yl)diazenyl]-3-
methyl-1,3-thiazol-3-ium

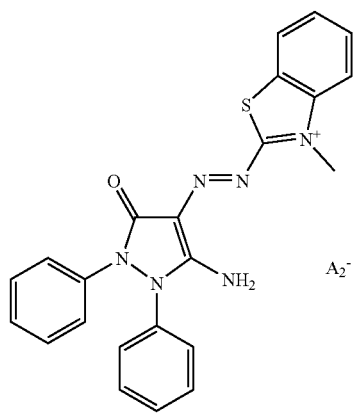

2-[(E)-(5-amino-3-oxo-1,2-
diphenyl-2,3-dihydro-1H-
pyrazol-4-yl)diazenyl]-3-
methyl-1,3-benzothiazol-3-ium

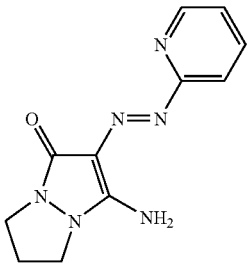

3-amino-2-[(E)-pyridin-2-yl-
diazenyl]-6,7-dihydro-1H,5H-
pyrazolo[1,2-a]pyrazol-1-one

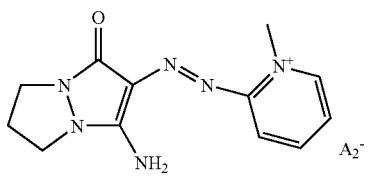

2-[(E)-(3-amino-1-oxo-6,7-
dihydro-1H,5H-pyrazolo-
[1,2-a]pyrazol-2-yl)diazenyl]-
1-methylpyridinium

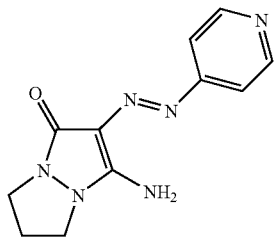

3-amino-2-[(E)-pyridin-4-yl-
diazenyl]-6,7-dihydro-1H,5H-
pyrazolo[1,2-a]pyrazol-1-one

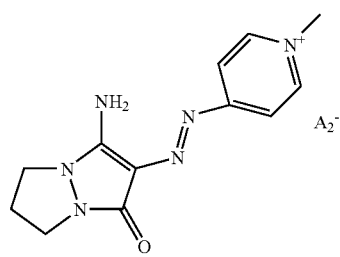

4-[(E)-(3-amino-1-oxo-6,7-
dihydro-1H,5H-pyrazolo-
[1,2-a]-pyrazol-2-yl)diazenyl]-
1-methylpyridinium

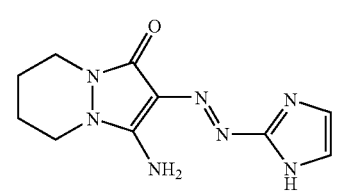

3-amino-2-[(E)-1H-imidazol-
2-yldiazenyl]-6,7-dihydro-
1H,5H-pyrazolo[1,2-a]pyrazol-
1-one -continued

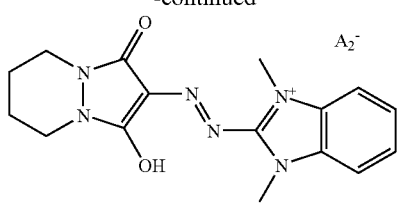

2-[(E)-(3-hydroxy-1-oxo-
5,6,7,8-tetrahydro-1H-pyrazolo-
[1,2-a]pyridazin-2-yl)-
diazenyl]-1,3-dimethyl-1H-
3,1-benzimidazol-3-ium

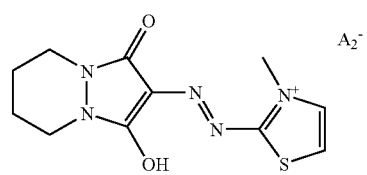

2-[(E)-(3-hydroxy-1-oxo-
5,6,7,8-tetrahydro-1H-pyrazolo-
[1,2-a]pyridazin-2-yl)-
diazenyl]-3-methyl-1,3-thiazol-
3-ium

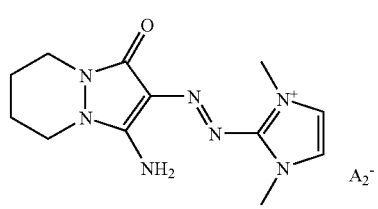

2-[(E)-(3-amino-1-oxo-5,6,7,8-
tetrahydro-1H-pyrazolo-[1,2-
a]pyridazin-2-yl)-diazenyl]-1,3-
dimethyl-1H-imidazol-3-ium

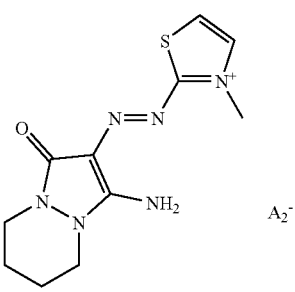

2-[(E)-(3-amino-1-oxo-5,6,7,8-
tetrahydro-1H-pyrazolo-[1,2-a]-
pyridazin-2-yl)diazenyl]-
3-methyl-1,3-thiazol-3-ium

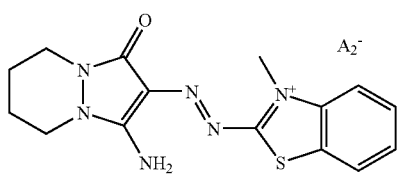

2-[(E)-(3-amino-1-oxo-5,6,7,8-
tetrahydro-1H-pyrazolo-[1,2-a]-
pyridazin-2-yl)-diazenyl]-3-
methyl-1,3-benzothiazol-3-ium -continued

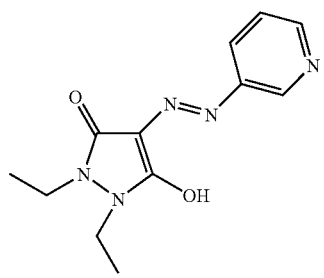

1,2-diethyl-5-hydroxy-4-[(E)-
pyridin-3-yldiazenyl]-
1,2-dihydro-3H-pyrazol-3-one

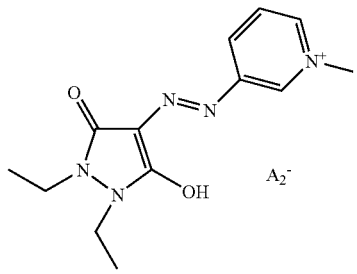

3-[(E)-(1,2-diethyl-5-hydroxy-
3-oxo-2,3-dihydro-1H-pyrazol-
4-yl)diazenyl]-1-
methylpyridinium The azo derivatives containing a pyrazolinone unit of formula (I) that are useful in the context of the invention may for example be prepared according to the synthesis scheme below:

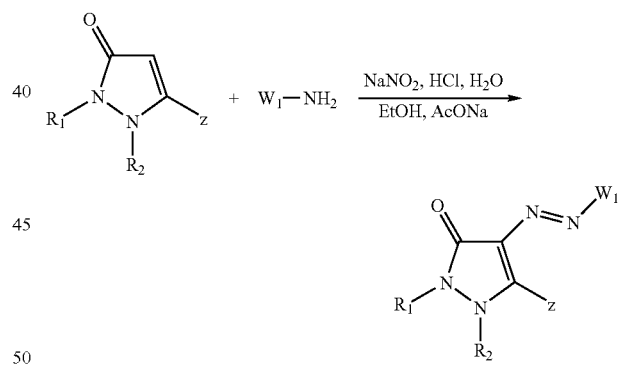

The various steps of this synthesis scheme are inspired by the following publications:

patent application GB 1 005 233;

Helvetica Chemica Acta (1950), 33, 1183-94: synthesis of 3-amino-5-pyrazolones;

Indian Journal of Chemistry, Pr. ELNAGDI, 1971: synthesis of azo compounds of the 4-arylazo-1,2-diphenylpyrazolin-3,5-dione family;

Pigment and Resin Technology (2001), 30(2), 99-108;

Journal of Heterocyclic Chemistry (2001), 38(3), 613-616.

In the case where $W_1$ is a phenyl radical substituted with a group chosen from a radical $NR'_1R'_2$, the synthesis scheme may be represented as follows:

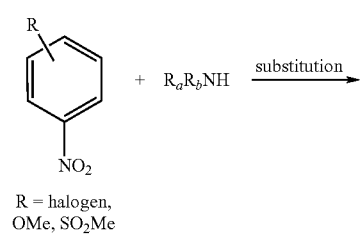

R = halogen, OMe, SO₂Me

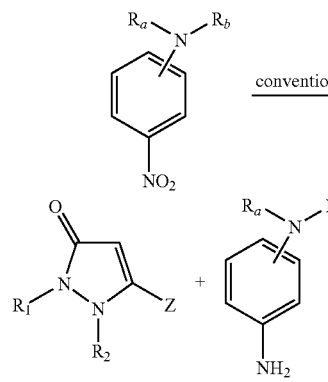

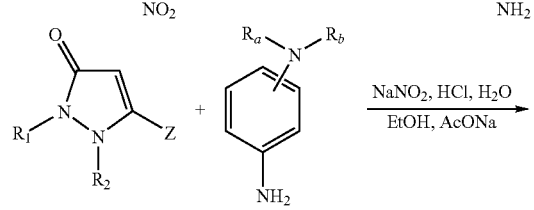

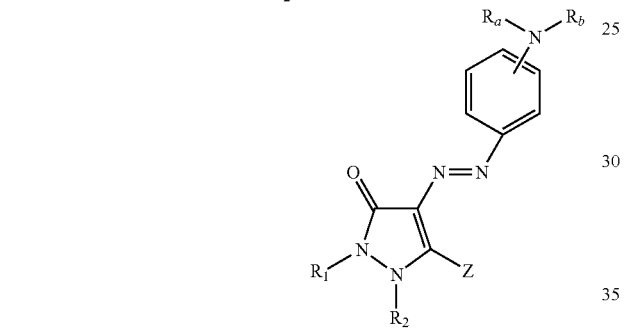

In the case where W₁ is a phenyl radical substituted with a cationic group of the quaternary ammonium type of formula (II), the synthesis scheme may comprise an additional step which may be represented as follows:

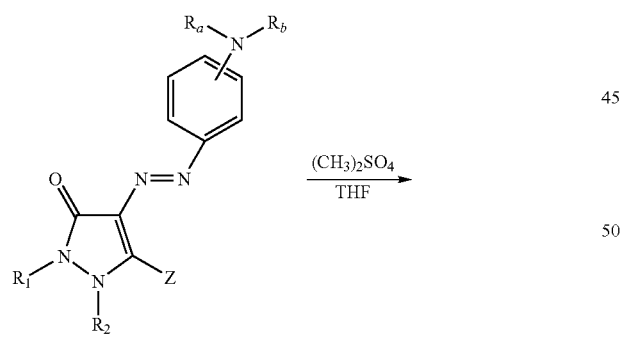

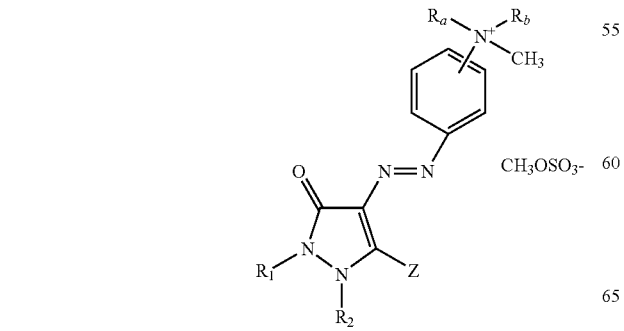

In the case where W₁ is an aromatic heterocyclic group, for example an imidazole ring, the synthesis scheme may be represented as follows:

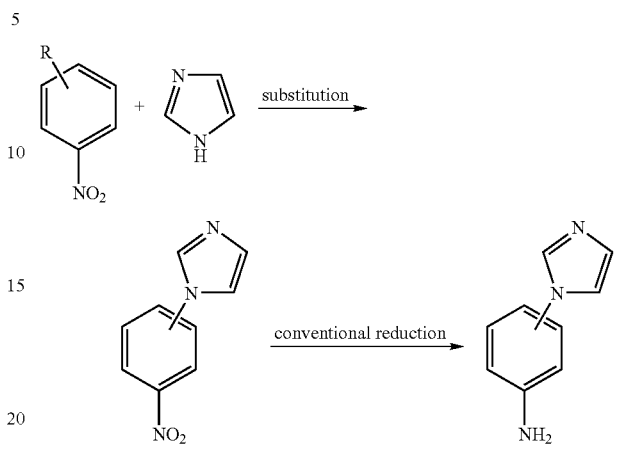

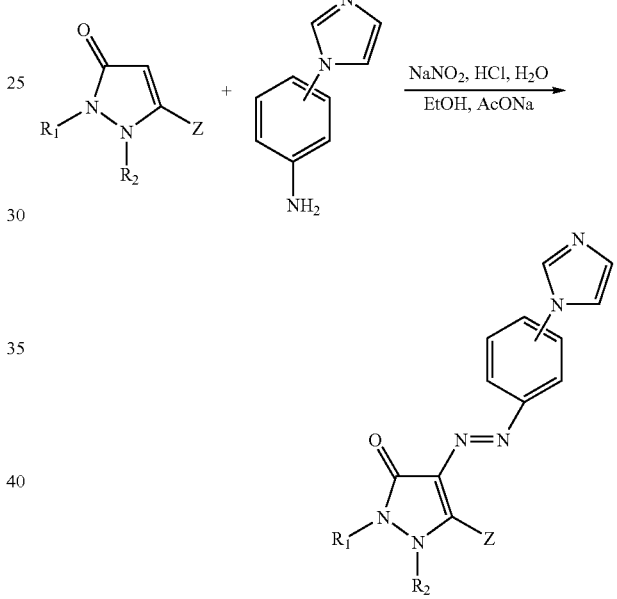

In the case where W₁ is a cationic aromatic heterocyclic group, for example an imidazolium ring, the synthesis scheme may comprise an additional step which may be represented as follows:

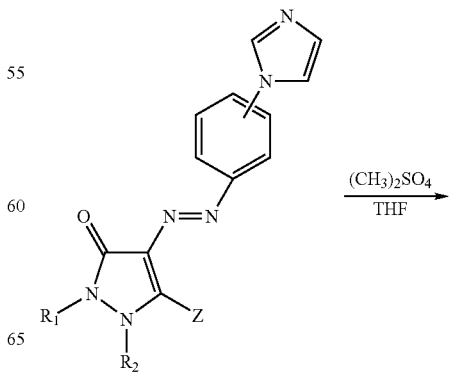

-continued

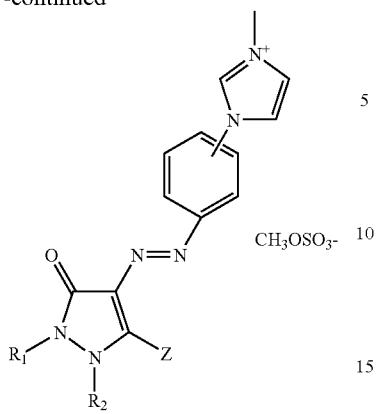

In the case where $W_1$ is an aromatic heterocyclic group, for example a pyridine ring, the synthesis scheme may be represented as follows:

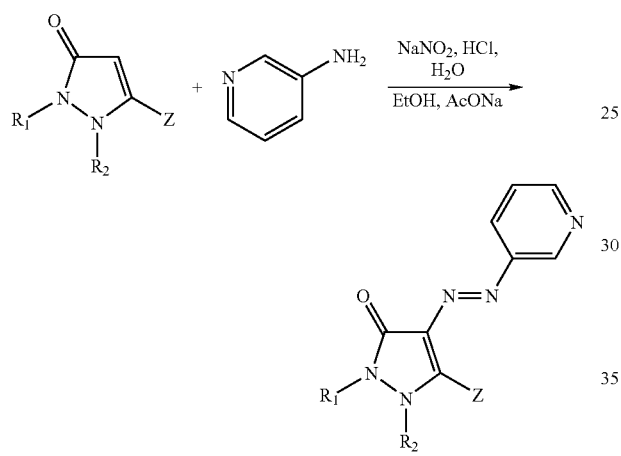

In the case where $W_1$ is a cationic aromatic heterocyclic group, for example a pyridinium ring, the synthesis scheme may comprise an additional step which may be represented as follows:

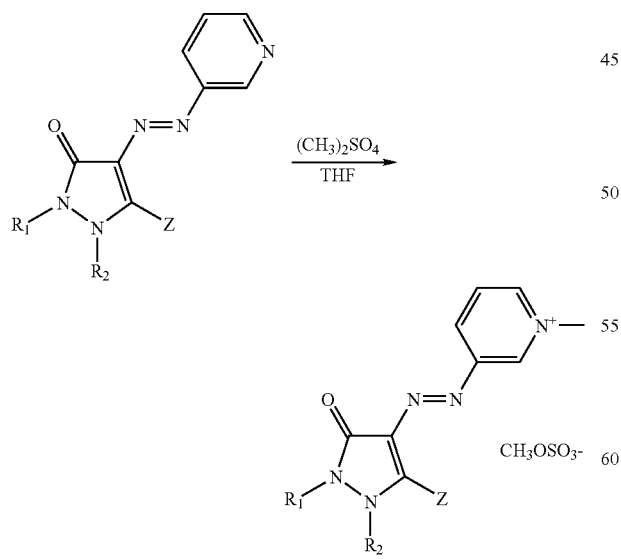

The subject of the present invention is also a composition for dyeing keratin fibres comprising, in an appropriate medium for dyeing, at least one direct dye chosen from azo derivatives containing a pyrazolinone unit of formula (I), their mesomers, their addition salts with an acid and their solvates, with the exception of the following molecules:

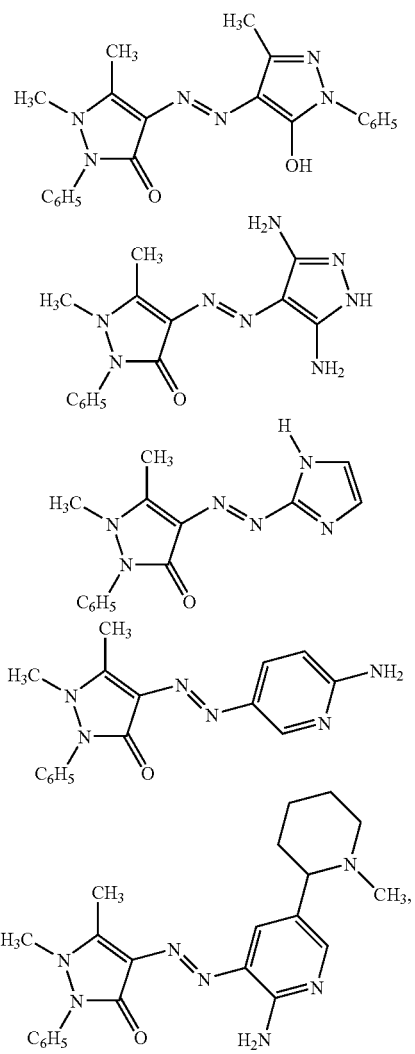

their mesomeric forms, their addition salts with an acid and their solvates.

The following molecules:

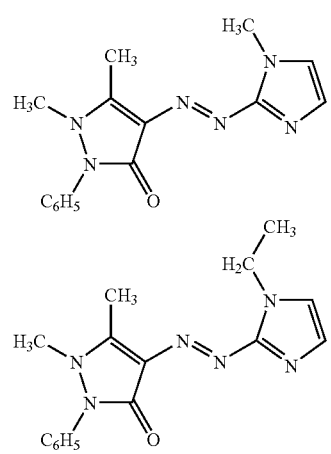

-continued

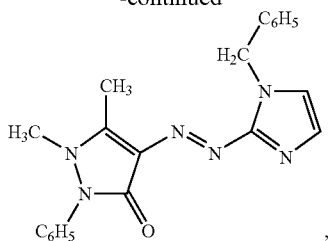

their mesomeric forms, their addition salts with an acid and their solvates are not excluded for the compositions in accordance with the present invention.

The direct dye(s) that are useful in the context of the invention represent in general from 0.01 to 5% by weight relative to the total weight of the composition, more particularly from 0.05 to 2% by weight relative to the total weight of the composition.

The composition according to the invention may further comprise an oxidation base. This oxidation base may be chosen from oxidation bases conventionally used for oxidation dyeing, for example para-phenylenediamines, bis-phenylalkylenediamines, para-aminophenols, ortho-aminophenols and heterocyclic bases.

Among the para-phenylenediamines, there may be mentioned more particularly, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl) amino-2-methylaniline, 4-N,N-bis(β-hydroxyethyl)-amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and their addition salts with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and their addition salts with an acid are particularly preferred.

Among the bis-phenylalkylenediamines, there may be mentioned, by way of example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylene-diamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and their addition salts with an acid.

Among the para-aminophenols, there may be mentioned, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol, 4-amino-2-fluorophenol, and their addition salts with an acid.

Among the ortho-aminophenols, there may be mentioned, by way of example, 2-aminophenol, 2-amino-5-methylphenol, 2-amino-6-methylphenol, 5-acetamido-2-aminophenol, and their addition salts with an acid.

Among the heterocyclic bases, there may be mentioned, by way of example, the pyridine derivatives, the pyrimidine derivatives and the pyrazole derivatives and the derivatives of the pyrazolo[1,2-a]pyrazol-1-one type.

Among the pyridine derivatives, there may be mentioned the compounds described for example in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their addition salts with an acid.

Among the pyrimidine derivatives, there may be mentioned the compounds described for example in patents DE 2 359 399; JP 88-169 571; JP 05 163 124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in patent application FR-A-2 750 048 and among which there may be mentioned pyrazolo-[1,5-a]pyrimidine-3,7-diamine; 2,5-dimethylpyrazolo-[1,5-a]pyrimidine-3,7-diamine; pyrazolo[1,5-a]-pyrimidine-3,5-diamine; 2,7-dimethylpyrazolo [1,5-a]-pyrimidine-3,5-diamine; 3-aminopyrazolo[1,5-a]-pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]-pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo-[1,5-a]pyrimidine and their addition salts with an acid and their tautomeric forms when a tautomeric equilibrium exists.

Among the pyrazole derivatives, there may be mentioned the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxy-ethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

Among the derivatives of the pyrazolo[1,2-a]pyrazol-1-one type, there may be mentioned compounds such as 2,3-diamino-6,7-dihydro-1H,5H-pyrazolo[1,2-a]pyrazol-1-one.

The composition according to the invention may further contain one or more couplers conventionally used for dyeing keratin fibres. Among these couplers, there may be mentioned in particular meta-phenylenediamines, meta-aminophenols, metadiphenols, naphthalene couplers and heterocyclic couplers.

By way of example, there may be mentioned 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxy-ethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and their addition salts with an acid.

In the composition of the present invention, the oxidation base(s) are in general present in a quantity of between 0.001 and 10% by weight of the total weight of the dye composition, and more preferably 0.005 to 6% by weight. The coupler(s) are in general present in a quantity of between 0.001 and 10% by weight of the total weight of the dye composition, and more preferably between 0.005 and 6% by weight.

In general, the addition salts with an acid which can be used in the context of the dye compositions of the invention for the oxidation bases and the couplers are chosen in particular from hydrochlorides, hydrobromides, sulphates, citrates, succinates, tartrates, lactates, tosylates, benzenesulphonates, phosphates and acetates.

The composition according to the invention may optionally comprise at least one additional direct dye different from the azo derivatives containing a pyrazolinone unit in accordance with the invention. It may be chosen from cationic or non-ionic species.

By way of non-limiting examples, there may be mentioned nitrobenzene dyes, azo, azomethine, methine, tetraaza-pentamethine, anthraquinone, naphthoquinone, benzoquinone, phenothiazine, indigoid, xanthene, phenanthridine and phthalocyanine dyes, those derived from triarylmethane and natural dyes, alone or as mixtures.

It may for example be chosen from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl) aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, 1-amino-2-nitro-4-hydroxy-5-methylbenzene.

The additional direct dye may also be chosen from the yellow and green-yellow nitrobenzene direct dyes, there may for example be mentioned the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-di(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-β-hydroxyethyl)amino-3-nitrobenzenesulphonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl) amino-2-nitrobenzene, 4-(β-hydroxyethyl)amino-3-nitrobenzamide.

There may also be mentioned the blue or purple nitrobenzene direct dyes, such as for example 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)-amino-4-(N-methyl-N-β-hydroxyethyl) amino-2-nitrobenzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, 2-nitro-para-phenylenediamines having the following formula (V):

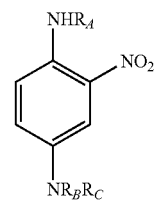

(V)

in which:

$R_B$ represents a $C_1$-$C_4$ alkyl radical, a β-hydroxyethyl or β-hydroxypropyl or γ-hydroxypropyl radical;

$R_A$ and $R_C$, which are identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able to simultaneously denote a β-hydroxyethyl radical when $R_B$ is a γ-hydroxypropyl radical, such as those described in French patent FR 2 692 572.

Among the azo direct dyes which can be used according to the invention, there may be mentioned the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369, FR 2 844 269.

Among these compounds, the following dyes may be mentioned most particularly: 1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]-pyridinium methylsulphate.

The following dyes, described in COLOUR INDEX INTERNATIONAL 3rd edition, may also be mentioned among the azo direct dyes: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

There may also be mentioned 1-(4'-aminodiphenylazo)-2-methyl-4-bis(β-hydroxyethyl)aminobenzene and 4-hydroxy-3-(2-methoxyphenylazo)-1-naphthalenesulphonic acid.

The following dyes may be mentioned among the quinone direct dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

The following compounds may be mentioned among the azine dyes: Basic Blue 17, Basic Red 2.

The following compounds may be mentioned among the triarylmethane dyes which can be used according to the invention: Basic Green 1, Acid Blue 9, Basic Violet 3, Basic Violet 14, Basic Blue 7, Acid Violet 49, Basic Blue 26, Acid Blue 7.

The following compounds may be mentioned among the indoamine dyes which can be used according to the invention: 2-β-hydroxyethylamino-5-[bis(β-4'-hydroxyethyl)amino]anilino-1,4-benzoquinone, 2-β-hydroxyethylamino-5-(2'-methoxy-4'-amino)anilino-1,4-benzoquinone, 3-N(2'-chloro-4'-hydroxy)phenylacetylamino-6-methoxy-1,4-benzoquinone imine, 3-N(3'-chloro-4'-methylamino)phenylureido-6-methyl-1,4-benzoquinone imine, 3-[4'-N-(ethylcarbamoylmethyl)amino]phenylureido-6-methyl-1,4-benzoquinone imine.

The following compounds may be mentioned among the tetraazapentamethine type dyes which can be used according to the invention: 2-((E)-{(E)-[(1,3-dimethyl-1,3-dihydro-2H-imidazol-2-ylidene)hydrazono]methyl}-diazenyl)-1,3-dimethyl-1H-imidazol-3-ium chloride; 2-{(E)-[(1Z)-N-(1,3-dimethyl-1,3-dihydro-2H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)-hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]hydrazono}ethyl)diazenyl]pyridinium chloride; 1-methyl-2-((E)-{E)-[(2Z)-(1-methylpyridin-2(1H)-ylidene)hydrazono]methyl}diazenyl)pyridinium chloride; 1-(2-hydroxyethyl)-2-[(E)-((E)-{(2E)-[1-(2-hydroxyethyl)pyridin-2(1H)-ylidene]hydrazono}methyl)diazenyl]pyridinium acetate.

Among the natural direct dyes which can be used according to the invention, there may be mentioned lawsone, juglone, alizarin, purpurin, carminic acid, kermesic acid, purpurogallin, protocatechaldehyde, indigo, isatin, curcumin, spinulosin, apigenidin. It is also possible to use extracts or decoctions containing these natural dyes and in particular poultices or extracts based on henna.

If they are present, the content of additional direct dyes in the composition varies in general from 0.001 to 20% by weight relative to the weight of the composition, and preferably from 0.01 to 10% by weight relative to the weight of the composition.

The appropriate medium for dyeing, also called dye carrier, is generally constituted of water or of a mixture of water and at least one organic solvent for solubilizing the compounds which might not be sufficiently soluble in water.

More particularly, the organic solvents are chosen from linear or branched, preferably saturated monoalcohols or diols comprising from 2 to 10 carbon atoms, such as ethyl alcohol, isopropyl alcohol, hexyleneglycol (2-methyl-2,4-pentanediol), neopentyl glycol and 3-methyl-1,5-pentanediol; aromatic alcohols such as benzyl alcohol, phenylethyl alcohol; glycols or glycol ethers such as, for example, ethylene glycol monomethyl, monoethyl and monobutyl ethers, propylene glycol or its ethers such as, for example, propylene glycol monomethyl ether, butylene glycol, dipropylene glycol; and alkyl ethers of diethylene glycol, in particular as $C_1$-$C_4$, such as for example diethylene glycol monoethyl ether or monobutyl ether, alone or as a mixture.

The customary solvents described above, if they are present, usually represent from 1 to 40% by weight, more preferably from 5 to 30% by weight, relative to the total weight of the composition.

The dye composition in accordance with the invention may also contain various adjuvants conventionally used in compositions for dyeing the hair, such as anionic, cationic, non-ionic, amphoteric or zwitterionic surfactants or mixtures thereof, anionic, cationic, non-ionic, amphoteric or zwitterionic polymers or mixtures thereof, inorganic or organic thickening agents, and in particular anionic, cationic, non-ionic and amphoteric polymeric associative thickeners, antioxidants, penetrating agents, sequestering agents, perfumes, buffers, dispersing agents, conditioning agents such as for example modified or non-modified, volatile or non-volatile silicones, film-forming agents, ceramides, preservatives and opacifying agents.

These adjuvants above are in general present in a quantity for each of them of between 0.01 and 20% by weight relative to the weight of the composition.

Of course, persons skilled in the art will be careful to choose this or these optional additional compounds such that the advantageous properties intrinsically attached to the oxidation dye composition in accordance with the invention are not, or not substantially, impaired by the addition(s) envisaged.

The pH of the dye composition in accordance with the invention is generally between about 3 and 12, and preferably between about 5 and 11. It may be adjusted to the desired value by means of acidifying or alkalinizing agents normally used for dyeing keratin fibres or else with the aid of conventional buffer systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines and their derivatives, sodium or potassium hydroxides and the compounds having the following formula (VI):

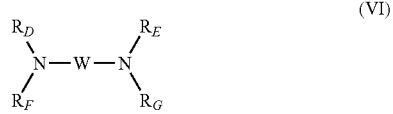

(VI)

in which W is a propylene residue optionally substituted with a hydroxyl group or a $C_1$-$C_4$ alkyl radical; $R_D$, $R_E$, $R_F$ and $R_G$, which are identical or different, represent a hydrogen atom, a $C_1$-$C_4$ alkyl or $C_1$-$C_4$ hydroxyalkyl radical.

The dye composition according to the invention may be provided in various forms, such as in the form of liquids, creams, gels, or in any other form appropriate for dyeing keratin fibres, and in particular human hair.

The composition according to the invention may additionally comprise at least one oxidizing agent in order to allow simultaneous lightening.

The oxidizing agent may be any oxidizing agent conventionally used in the field. Accordingly, it may be chosen from hydrogen peroxide, urea peroxide, alkali metal bromates, persalts such as perborates and persulphates, and enzymes among which there may be mentioned peroxidases, oxidoreductases containing 2 electrons such as uricases, and oxygenases containing 4 electrons such as laccases.

The subject of the invention is also a dyeing method consisting in bringing a composition comprising, in an appropriate medium for dyeing, at least one direct dye chosen from the azo derivatives containing a pyrazolinone unit of formula (I), their mesomeric forms, their addition salts with an acid and their solvates, into contact with the said dry or wet fibres, for an exposure time sufficient to obtain the desired colour.

When the oxidizing agent is present, it may either be added to the composition comprising the compound(s) of formula (I) at the time of use, or it may be applied directly to the keratin fibre.

Regardless of the variant selected, with or without oxidizing agent, the exposure time is in general between a few seconds and 30 minutes, preferably between 3 and 15 minutes.

The temperature at which the composition is allowed to act is in general between 15 and 220° C., more particularly between 15 and 80° C., preferably between 15 and 40° C.

At the end of the exposure time, the composition is removed by rinsing with water, followed by washing with a shampoo, and optionally drying.

Another subject of the invention is a multicompartment device or kit for dyeing in which a first compartment contains the composition comprising, in an appropriate medium for dyeing, at least one direct dye chosen from the azo derivatives containing a pyrazolinone unit of formula (I), their mesomeric forms, their addition salts with an acid and their solvates, and a second compartment contains the oxidizing composition. This device may be equipped with a means which makes it possible to deliver the desired mixture on the hair, such as the devices described in patent FR-2 586 913.

The following molecules:

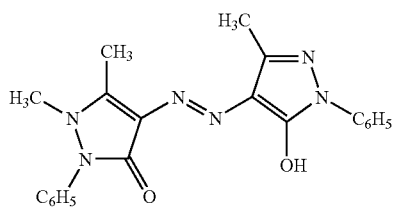

-continued

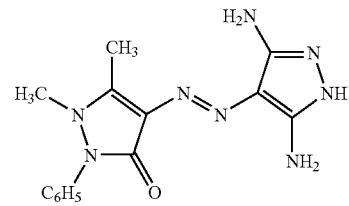

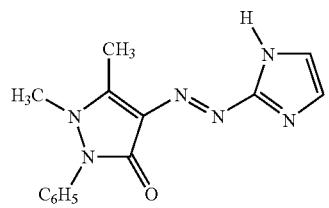

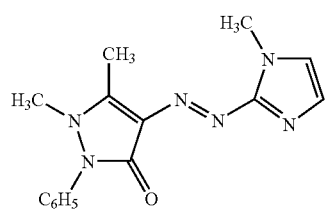

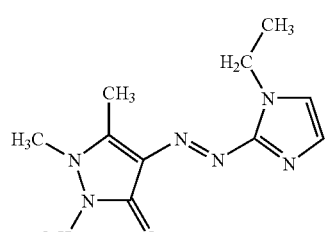

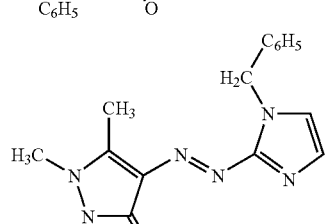

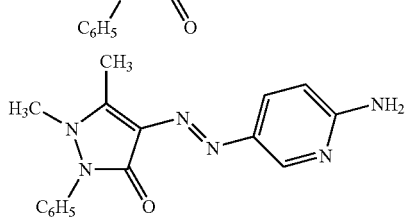

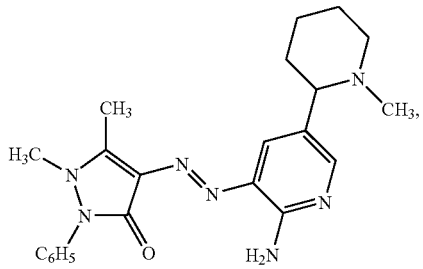

their mesomeric forms, their addition salts with an acid and their solvates are not excluded for the methods and the devices in accordance with the present invention.

The examples which follow serve to illustrate the invention without however being limiting.

EXAMPLES

Examples of Synthesis

Example 1

Synthesis of 3-amino-2-[(E)-pyridin-3-yldiazenyl]-6,7-dihydro-1H,5H-pyrazolo[1,2-a]pyrazol-1-one and of 3-[(E)-(3-amino-1-oxo-6,7-dihydro-1H,5H-pyrazolo-[1,2-a]pyrazol-2-yl)diazenyl]-1-methylpyridinium methyl sulphate

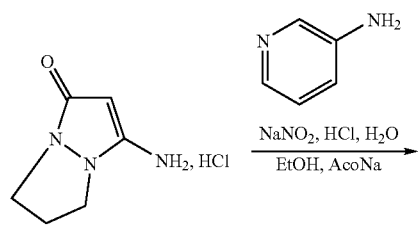

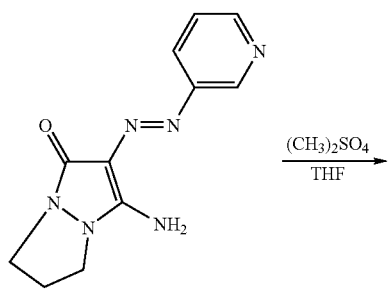

Step 1: Synthesis of 3-amino-2-[(E)-pyridin-3-yldiazenyl]-6,7-dihydro-1H,5H-pyrazolo[1,2-a]pyrazol-1-one

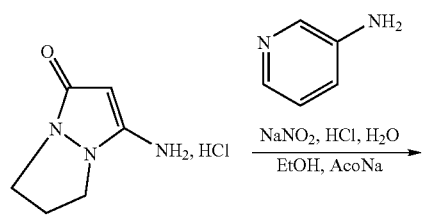

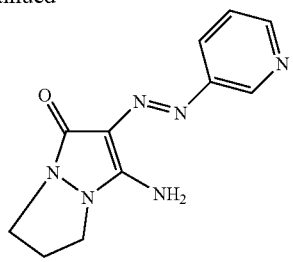

0.025 mole of 3-aminopyridine is solubilized in 10 ml of 6N hydrochloric acid. The medium is cooled to zero degrees, and then a solution of 0.025 mole of sodium nitrite in 10 ml of water is added over 10 minutes. The medium is then kept stirring for 30 minutes at a temperature of between 0 and 5° C.

A mixture of 0.025 mole of 3-amino-6,7-dihydro-1H,5H-pyrazolo[1,2-a]pyrazol-1-one hydrochloride, 20 ml of ethanol, 20 ml of water and 0.075 mole of sodium acetate is then added to the reaction medium.

After two hours at a temperature of between 0 and 5° C., the medium is poured over 500 g of ice and the pH is adjusted to 8. The yellow solid obtained is drained, washed with water and dried under vacuum in the presence of phosphorus pentaoxide to constant weight. 5.81 g of a yellow powder are recovered.

Step 2: Synthesis of 3-[(E)-(3-amino-1-oxo-6,7-dihydro-1H,5H-pyrazolo[1,2-a]pyrazol-2-yl)diazenyl]-1-methyl-pyridinium methyl sulphate

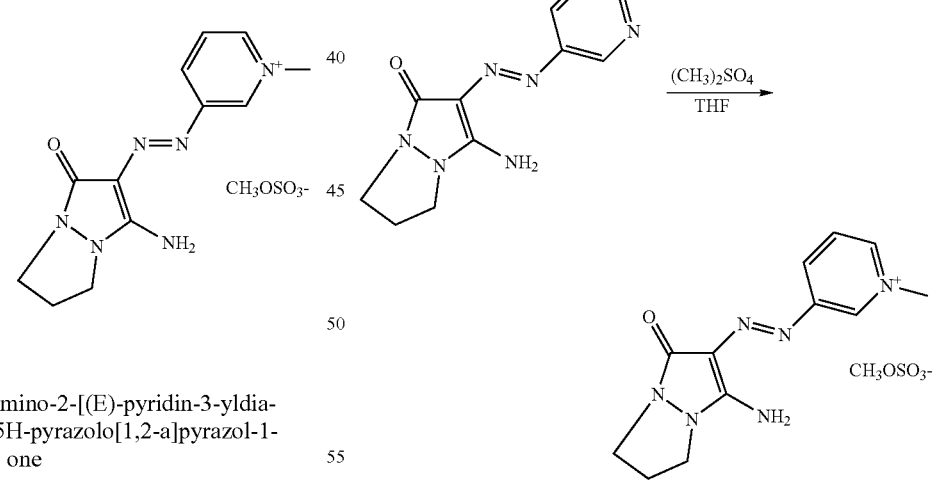

1 mmol of dimethyl sulphate is added to a mixture of 5 mmol of 3-amino-2-[(E)-pyridin-3-yldiazenyl]-6,7-dihydro-1H,5H-pyrazolo[1,2-a]pyrazol-1-one and 20 ml of THF. The temperature of the medium is brought to 75° C. for 2 hours.

After cooling to room temperature, the orange-yellow solid formed is drained, washed with isopropyl ether and dried under vacuum in the presence of phosphorus pentaoxide to constant weight. 1.81 g of an orange-yellow powder are recovered, that is a yield of 97.7%. $^1$H NMR analysis, DMSO D6: 2.44 (q, 2H); 3.37 (s, 3H); 3.62 (t, 2H); 3.8 (t, 2H); 4.37 (s, 3H); 8.05 (dd, 1H); 8.58 (d+broad s, 3H); 8.68 (d, 1H); 9.12 (broad s, 1H).

Example 2

Synthesis of 3-hydroxy-2-[(E)-pyridin-3-yldiazenyl]-5,6,7,8-tetrahydro-1H-pyrazolo[1,2-a]pyridazin-1-one and of 3-[(E)-(3-hydroxy-1-oxo-5,6,7,8-tetrahydro-1H-pyrazolo[1,2-a]pyridazin-2-yl)diazenyl]-1-methyl-pyridinium methyl sulphate

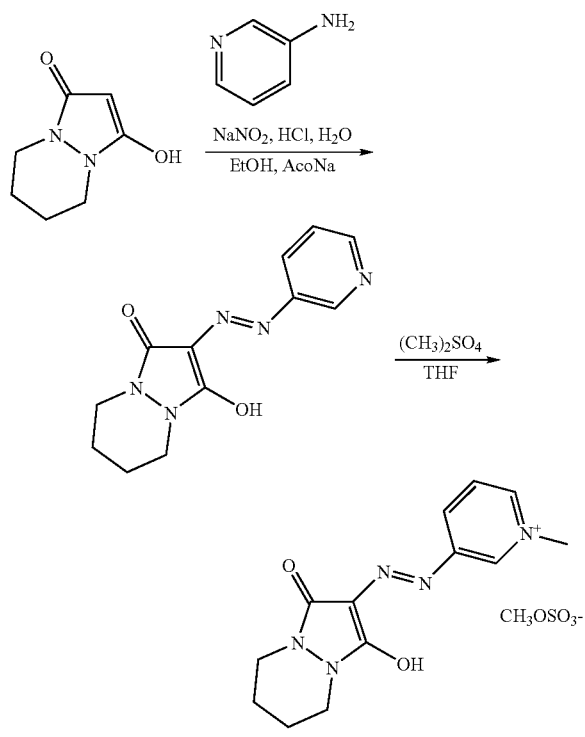

Step 1: Synthesis of 3-hydroxy-2-[(E)-pyridin-3-yl-diazenyl]-5,6,7,8-tetrahydro-1H-pyrazolo[1,2-a]-pyridazin-1-one

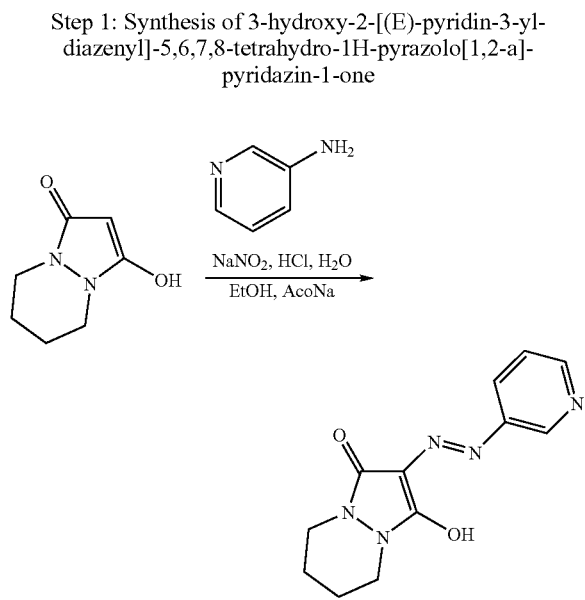

2.24 g of 3-aminopyridine are solubilized in 10 ml of 6N hydrochloric acid. The medium is cooled to zero degrees, and then a solution of 1.79 g of sodium nitrite in 10 ml of water are added over 10 minutes. The medium is then kept stirring for 30 minutes at a temperature of between 0 and 5° C.

A mixture of 4 g of tetrahydro-1H-pyrazolo-[1,2-a]pyridazine-1,3(2H)-dione, 20 ml of ethanol, 20 ml of water and 6.57 g of sodium acetate is then added to the reaction medium.

After two hours at a temperature of between 0 and 5° C., the medium is poured over 500 g of ice and the pH is adjusted to 8. After extracting with dichloromethane, drying the organic phase over sodium sulphate and evaporating under reduced pressure, 2.5 g of product are obtained.

Analysis by Mass Spectrometry

The quasi-molecular ions [M+H]+, [M+Na]+, [M+Na+CH$_3$OH]+, [2M+H]+, [2M+Na]+, [M−H]−, [M−H+H$_2$O]−, [2M−2H+Na]+ of the expected molecule C$_{12}$H$_{13}$N$_5$O$_2$ are mainly detected.

The results obtained by NMR confirm that the expected product was indeed obtained.

Step 2: Synthesis of 3-[(E)-(3-hydroxy-1-oxo-5,6,7,8-tetrahydro-1H-pyrazolo[1,2-a]pyridazin-2-yl)diazenyl]-1-methylpyridinium methyl sulphate

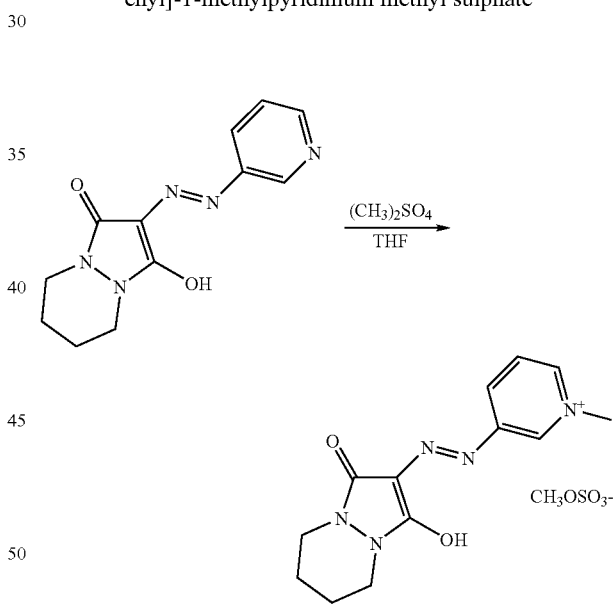

0.72 ml of dimethyl sulphate is added to a mixture of 1.9 mmol of 3-hydroxy-2-[(E)-pyridin-3-yldiazenyl]-5,6,7,8-tetrahydro-1H-pyrazolo[1,2-a]pyridazin-1-one and 5 ml of THF. The medium turns to red instantly and the stirring is maintained for 3 hours.

The red-orange solid formed is drained, washed with THF and dried under vacuum in the presence of phosphorus pentaoxide to constant weight. 0.65 g of a red-orange powder is recovered, that is a yield of 97.7%.

$^1$H NMR analysis, DMSO D6: 1.44 (m, 4H); 3.37 (s, 4); 3.59 (m, 4H); 3.49 (s, 3H); 8.08 (m, 1H); 8.59 (m, 1H); 8.71 (m, 1H); 9.12 (broad s, 1H); 12.96 (broad s, 1H).

Example 3

Synthesis of 1,2-diethyl-5-hydroxy-4-[(E)-pyridin-3-yl-diazenyl]-1,2-dihydro-3H-pyrazol-3-one and of 3-[(E)-(1,2-diethyl-5-hydroxy-3-oxo-2,3-dihydro-1H-pyrazol-4-yl)diazenyl]-1-methylpyridinium methyl sulphate

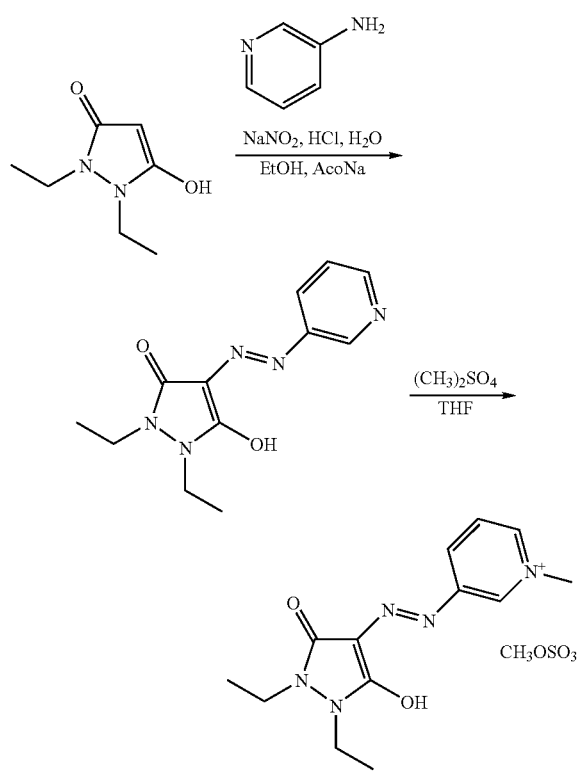

Step 1: Synthesis of 1,2-diethyl-5-hydroxy-4-[(E)-pyridin-3-yldiazenyl]-1,2-dihydro-3H-pyrazol-3-one

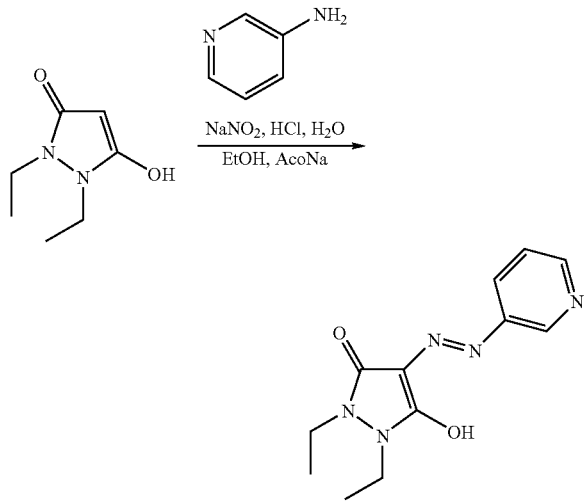

60.2 mg of 3-aminopyridine are solubilized in 0.25 ml of 6N hydrochloric acid. The medium is cooled to zero degrees, and then a solution of 44.2 mg of sodium nitrite in 0.25 ml of water is added over 3 minutes. The medium is then kept stirring for 10 minutes at a temperature of between 0 and 5° C. A mixture of 100 mg of 5-amino-1,2-diethyl-1,2-dihydro-3H-pyrazol-3-one, 0.5 ml of ethanol, 0.5 ml of water and 3 equivalents of sodium acetate is added to the reaction medium.

After 10 minutes at this temperature at a temperature of between 0 and 5° C., the orange precipitate obtained is drained, washed with water and dried under vacuum in the presence of phosphorus pentaoxide to constant weight. 0.105 g of a red-orange-yellow powder is recovered.

Analysis by Mass Spectrometry

The quasi-molecular ions [M+H]+, [M+Na]+, [M+Na+CH$_3$OH]+, [2M+H]+, [2M+Na]+, [M−H]−, [M+Cl]−, [2M−2H+Na]− of the expected molecule $C_{12}H_{15}N_5O_2$ are mainly detected.

The results obtained by NMR confirm that the expected product was indeed obtained.

Step 2: Synthesis of 3-[(E)-(1,2-diethyl-5-hydroxy-3-oxo-2,3-dihydro-1H-pyrazol-4-yl)diazenyl]-1-methylpyridinium methyl sulphate

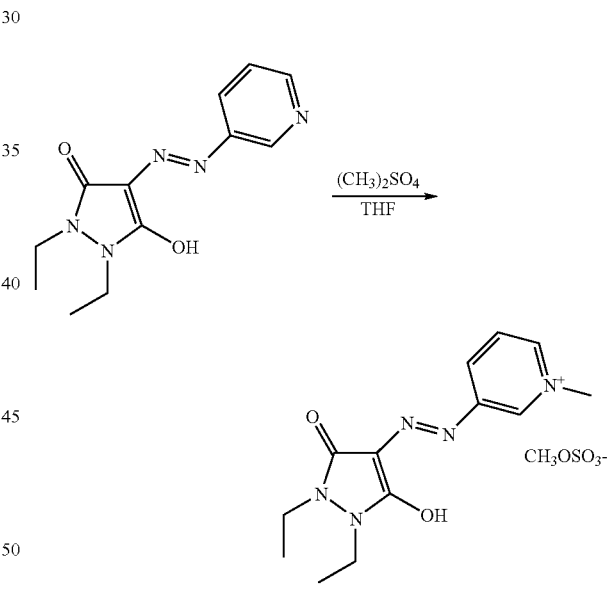

0.7 ml of dichloromethane and 0.4 mmol of 1,2-diethyl-5-hydroxy-4-[(E)-pyridin-3-yldiazenyl]-1,2-dihydro-3H-pyrazol-3-one are mixed, and then one equivalent of dimethyl sulphate is added to the mixture obtained. The medium turns to orange-red instantly.

The gummy red-orange solid is triturated in isopropyl ether, drained, washed with isopropyl ether and dried under vacuum in the presence of phosphorus pentaoxide to constant weight. 133 mg of a red powder are thus obtained with a yield of 84.8%.

$^1$H NMR analysis, DMSO D6: 1.08 (2t, 6H); 3.37 (s, 3); 3.71 (m, 4H); 8.10 (dd, 1H); 8.71 (d, 1H); 9.15 (broad s, 1H); 13.06 (broad s, 1H).

Example 4

Synthesis of 3-amino-2-[(E)-1,3-thiazol-2-yldiazenyl]-6,7-dihydro-1H,5H-pyrazolo[1,2-a]pyrazol-1-one and of 2-[(E)-(3-amino-1-oxo-6,7-dihydro-1H,5H-pyrazolo-[1,2-a]pyrazol-2-yl)diazenyl]-3-methyl-1,3-thiazol-3-ium methyl sulphate

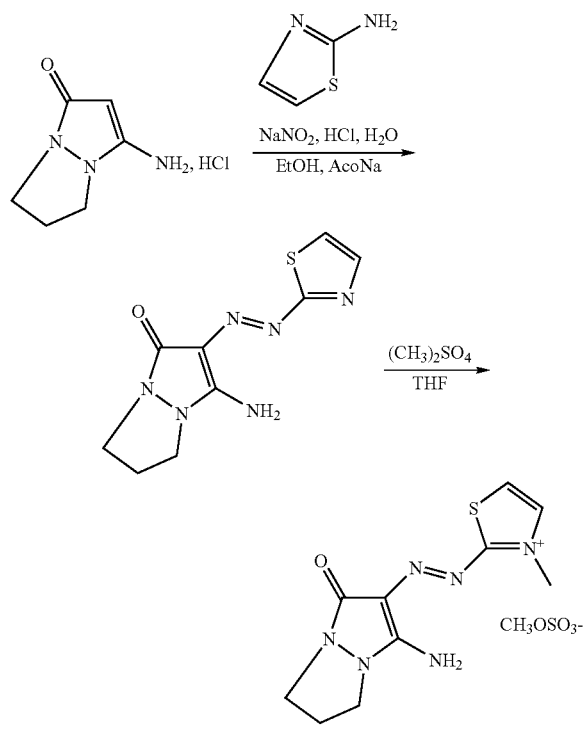

Step 1: Synthesis of 3-amino-2-[(E)-1,3-thiazol-2-yldiazenyl]-6,7-dihydro-1H,5H-pyrazolo[1,2-a]pyrazol-1-one

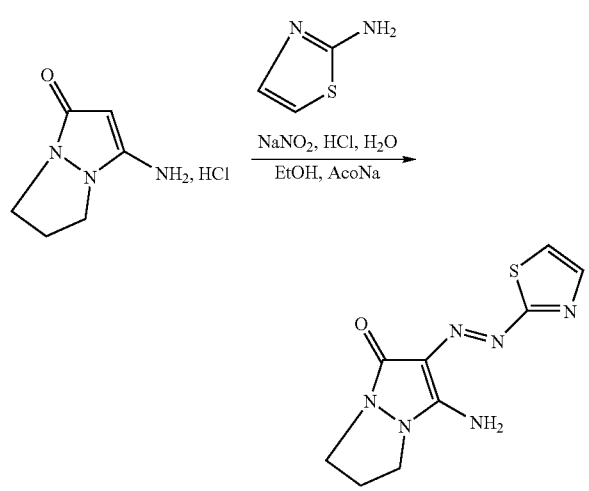

0.57 g of 2-aminothiazole is solubilized in 3 ml of 6N hydrochloric acid. The medium is cooled to zero degrees, and then a solution of 0.39 g of sodium nitrite in 3 ml of water is added over 3 minutes. The medium is then kept stirring for 10 minutes between 0 and 5° C. A mixture of 1 g of 3-amino-6,7-dihydro-1H,5H-pyrazolo[1,2-a]pyrazol-1-one hydrochloride, 5 ml of ethanol, 5 ml of water and 1.7 g of sodium acetate is added to the reaction medium.

After 40 minutes at a temperature of between 0 and 5° C., the orange precipitate obtained is drained, washed with water and dried under vacuum in the presence of phosphorus pentaoxide. 0.74 g of a red powder is recovered with a yield of 52.1%.

Analysis by Mass Spectrometry

The quasi-molecular ions [M+H]+, [M+Na]+, [M+Na+CH$_3$OH]+, [2M+H]+, [2M+Na]+, [M−H]−, [M+Cl]−, [2M−2H+Na]− of the expected molecule $C_9H_{10}N_6OS$ are mainly detected.

The results obtained by NMR confirmed that the expected product was indeed obtained.

Step 2: Synthesis of 2-[(E)-(3-amino-1-oxo-6,7-dihydro-1H,5H-pyrazolo[1,2-a]pyrazol-2-yl)diazenyl]-3-methyl-1,3-thiazol-3-ium methyl sulphate

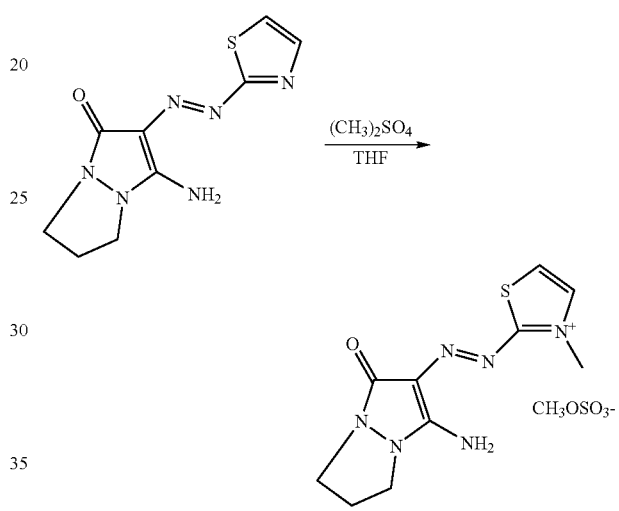

1 ml of dichloromethane, 0.5 ml of ethanol, 0.2 ml of N-methylpyrrolidone and 100 mg of 3-amino-2-[(E)-1,3-thiazol-2-yldiazenyl]-6,7-dihydro-1H,5H-pyrazolo-[1,2-a]pyrazol-1-one are mixed, and then two equivalents of dimethyl sulphate are added to the mixture obtained. The medium turns to orange instantly. After heating at 35° C. for 1 hour, the brick red solid obtained is triturated in isopropyl ether, drained, washed with isopropyl ether and dried under vacuum in the presence of phosphorus pentaoxide to constant weight. 105 mg of a brick red powder are recovered with a yield of 80%.

$^1$H NMR analysis, DMSO D6: 2.5 (m, 2H); 3.39 (s, 3H); 3.71 (t, 2H); 3.9 (t+s, 5H); 7.43 (d, 1H); 7.78 (d, 1H)

Example 5

Synthesis of 3-amino-2-[(E)-1H-imidazol-2-yldiazenyl]-6,7-dihydro-1H,5H-pyrazolo[1,2-a]pyrazol-1-one hydrochloride

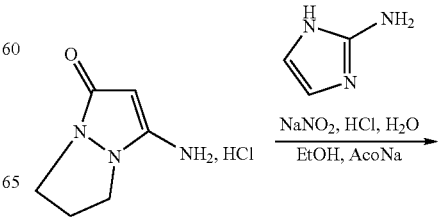

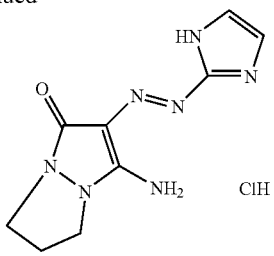

0.75 g of 2-aminoimidazole sulphate is solubilized in 3 ml of 6N hydrochloric acid. The medium is cooled to zero degrees, and then a solution of 0.39 g of sodium nitrite and 3 ml of water is added over 5 minutes. The medium is then kept stirring for 10 minutes.

A mixture of 1 g of 3-amino-6,7-dihydro-1H,5H-pyrazolo[1,2-a]pyrazol-1-one hydrochloride, 5 ml of ethanol, 5 ml of water and 1.4 g of sodium acetate is added to the reaction medium.

After 40 minutes at a temperature of between 0 and 5° C., the orange precipitate obtained is drained, washed with water and dried under vacuum in the presence of phosphorus pentaoxide. 0.97 g of an orange powder is recovered, that is a yield of 71%.

Analysis by Mass Spectrometry

The quasi-molecular ions [M+H]+, [M+Na]+, [2M+Na]+, [M−H]−, [M−2H+Na]−, [M−H+Na+Cl]− and the fragment ions detected at m/z, ESP-=138, m/z, ESP+=140, 166 (which may correspond respectively to $[C_6H_8N_3O]$—, $[C_6H_{10}N_3O]+$, $[C_6H_8N_5O]+$) of the expected molecule $C_9H_{11}N_7O$ are mainly detected.

$^1$H NMR analysis, DMSO D6: 2.46 (m, 2H); 3.62 (t, 2H); 3.97 (t, 2H); 7.39 (s, 2H); 8.60 (broad s, 2H); 11 (broad s, 1H)

Example 6

Synthesis of 3-hydroxy-2-[(E)-1H-imidazol-2-yl-diazenyl]-5,6,7,8-tetrahydro-1H-pyrazolo[1,2-a]-pyridazin-1-one

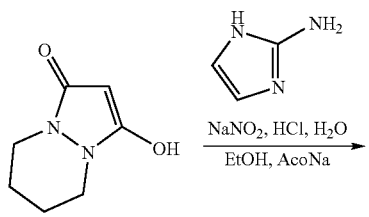

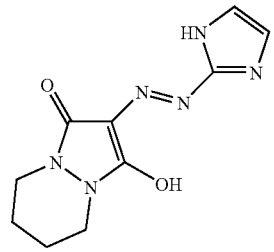

0.86 g of 2-aminoimidazole sulphate is solubilized in 3.5 ml of 6N hydrochloric acid. The medium is cooled to zero degrees, and then a solution of 0.447 g of sodium nitrite in 3.5 ml of water is added over 5 minutes. The medium is then kept stirring for 10 minutes at 0° C.

A mixture of 1 g of 3-amino-6,7-dihydro-1H,5H-pyrazolo[1,2-a]pyrazol-1-one hydrochloride, 5 ml of ethanol, 5 ml of water and 1.6 g of sodium acetate is added to the reaction medium.

After 40 minutes at this temperature of between 0 and 5° C., the dark orange precipitate obtained is drained, washed with water and dried under vacuum in the presence of phosphorus pentaoxide. 0.9 g of an orange-yellow powder is recovered.

Analysis by Mass Spectrometry

The quasi-molecular ions [M+H]+, [M+Na]+, [M+Na+CH$_3$OH]+, [2M+H]+, [2M+Na]+, [M−H]−, [M+Cl]−, [2M−2H+Na]− of the expected molecule $C_{12}H_{13}N_5O_2$ are mainly detected.

$^1$H NMR Analysis, DMSO D6: 1.67 (m, 4H); 3.38 (m, 4H); 7.17 (s, 2H); 13 (2H)

Examples of Dyeing

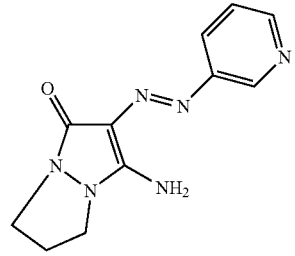

Dye 1

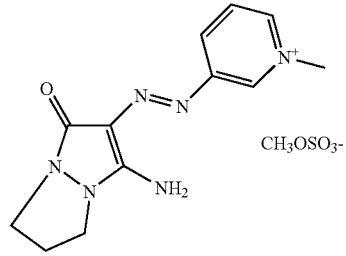

Dye 2

CH$_3$OSO$_3$-

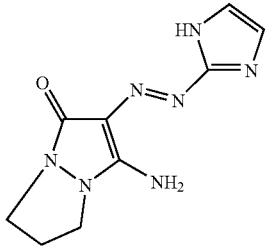

Dye 3

-continued

Dye 4

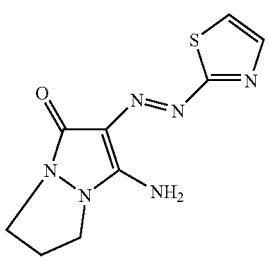

Dye 5

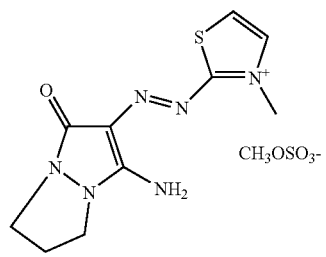

Dye 6

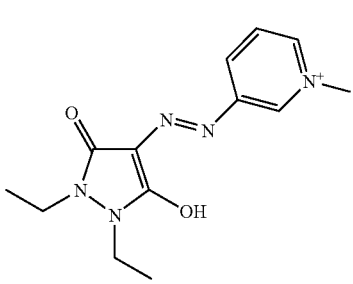

Dyeing in Acidic Medium

The following dye compositions are prepared:

| Composition | 1 | 2 | 3 | 4 | 5 | 6 |
|---|---|---|---|---|---|---|
| Dye 1 | $10^{-3}$ mole | — | — | — | — | — |
| Dye 2 | — | $10^{-3}$ mole | — | — | — | — |
| Dye 3 | — | — | $10^{-3}$ mole | — | — | — |
| Dye 4 | — | — | — | $10^{-3}$ mole | — | — |
| Dye 5 | — | — | — | — | $10^{-3}$ mole | — |
| Dye 6 | — | — | — | — | — | $10^{-3}$ mole |
| Dye carrier (1) | (*) | (*) | (*) | (*) | (*) | (*) |
| Demineralized water qs | 100 g | 100 g | 100 g | 100 g | 100 g | 100 g |

| (*): dye carrier (1) pH 7: | |
|---|---|
| Ethyl alcohol, 96% | 20.8 g |
| Pentasodium salt of diethylene-triamine-pentaacetic acid as 40% aqueous solution | 0.48 g AM |
| $C_8$-$C_{10}$ alkyl polyglucoside as 60% aqueous solution | 3.6 g AM |
| Benzyl alcohol | 2.0 g |
| Polyethylene glycol with 8 ethylene oxide units | 3.0 g |
| $Na_2HPO_4$ | 0.28 g |
| $KH_2PO_4$ | 0.46 g |

For the dyeings performed under non-lightening conditions (with no oxidant) these compositions are applied directly to the hair.

For dyeings performed under lightening conditions, an oxidizing medium is used. In this case, at the time of use, each composition is mixed with an equal weight of hydrogen peroxide at 20 volumes (6% by weight). A final pH equal to 7 is obtained.

Each composition with or without oxidizing agent is applied to locks of grey hair which is 90% white, in an amount of 6 g of composition per 1 g of hair. After an exposure time of 30 minutes, the locks are rinsed, washed with a standard shampoo, rinsed again and then dried.

The following dyeing results were obtained:

| Dye 1 | yellow |
|---|---|
| Dye 2 | yellow |
| Dye 3 | yellow |
| Dye 4 | bright yellow |
| Dye 5 | chromatic yellow |
| Dye 6 | orange-yellow |

Dyeing in a Basic Medium

The following dye compositions are prepared:

| Composition | 1 | 2 | 3 | 4 | 5 | 6 |
|---|---|---|---|---|---|---|
| Dye 1 | $10^{-3}$ mole | — | — | — | — | — |
| Dye 2 | — | $10^{-3}$ mole | — | — | — | — |
| Dye 3 | — | — | $10^{-3}$ mole | — | — | — |
| Dye 4 | — | — | — | $10^{-3}$ mole | — | — |
| Dye 5 | — | — | — | — | $10^{-3}$ mole | — |
| Dye 6 | — | — | — | — | — | $10^{-3}$ mole |
| Dye carrier (2) | (*) | (*) | (*) | (*) | (*) | (*) |
| Demineralized water qs | 100 g | 100 g | 100 g | 100 g | 100 g | 100 g |

(*): dye carrier (2) pH 9.5:
| | |
|---|---|
| Ethyl alcohol, 96% | 20.8 g |
| Pentasodium salt of diethylene-triamine-pentaacetic acid as 40% aqueous solution | 0.48 g AM |
| $C_8$-$C_{10}$ alkyl polyglucoside in 60% aqueous solution | 3.6 g AM |
| Benzyl alcohol | 2.0 g |
| Polyethylene glycol with 8 ethylene oxide units | 3.0 g |
| $NH_4Cl$ | 4.32 g |
| Aqueous ammonia with 20% of $NH_3$ | 2.94 g |

For the dyeings performed under non-lightening conditions (with no oxidant) these compositions are applied directly to the hair.

For dyeings performed under lightening conditions, an oxidizing medium is used. In this case, at the time of use, each composition is mixed with an equal weight of hydrogen peroxide at 20 volumes (6% by weight). A final pH equal to 9.5 is obtained.

Each composition with or without oxidizing agent is applied to locks of grey hair which is 90% white, in an amount of 6 g of composition per 1 g of hair. After an exposure time of 30 minutes, the locks are rinsed, washed with a standard shampoo, rinsed again and then dried.

The following dyeing results were obtained:

| | |
|---|---|
| Dye 1 | yellow |
| Dye 2 | yellow |
| Dye 3 | yellow |
| Dye 4 | bright yellow |
| Dye 5 | chromatic yellow |
| Dye 6 | orange-yellow |

The invention claimed is:

1. At least one azo pyrazolinone entity chosen from those of formula (I):

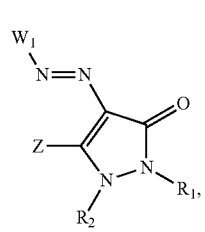

(I)

the mesomeric forms, acid addition salts, and solvates thereof, wherein:
W₁ is attached to the azo functional group via a carbon and is chosen from:
aromatic heterocyclic groups chosen from imidazole, benzimidazole, pyrazole, thiazole, benzothiazole, pyridine, pyrimidine, pyrazine, and pyridazine rings wherein said aromatic heterocyclic group is optionally substituted with at least one substituent;
cationic aromatic heterocyclic groups chosen from imidazolium, benzimidazolium, pyrazolium, thiazolium, benzothiazolium, pyridinium, pyrimidinium, pyrazinium, and pyridazinium rings wherein said cationic aromatic heterocyclic group is substituted with at least one substituent, one of the substituents being carried by a nitrogen atom and combined with an organic or inorganic anion; and
phenyls substituted with a substituent chosen from:
an aromatic heterocyclic group chosen from imidazole, benzimidazole, pyrazole, thiazole, benzothiazole, pyridine, pyrimidinine, pyrazine and pyridazine rings wherein said aromatic heterocyclic group is optionally substituted with at least one substituent;
a cationic aromatic heterocyclic group chosen from imidazolium, benzimidazolium, pyrazolium, thiazolium, benzothiazolium, pyridinium, pyrimidinium, pyrazinium and pyridazinium rings wherein said cationic aromatic heterocyclic group is substituted with at least one substituent, one of the substituents being carried by a nitrogen atom and combined with an organic or inorganic anion;
NR'₁R'₂; and
a cationic quaternary ammonium moiety of formula (II):

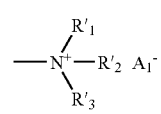

(II)

wherein:
R'₁ and R'₂, which are identical or different, are independently selected from —CO₂H, —C₁-C₆ alkyls optionally substituted with at least one substituent chosen from phenyl, hydroxyl, (C₁-C₆) alkoxy, cyano, amino, (C₁-C₆)(di) alkylamino, —CO₂H, C₁-C₆ alkyl carboxylate, sulphonic, and C₁-C₆ alkyl sulphonate; phenyl, benzyl, C₁-C₆ amidoalkyl, (C₁-C₆) trialkyl-silane (C₁-C₆) alkyl, and C₁-C₆ aminoalkyls wherein said C₁-C₆ aminoalkyl is N-protected by a moiety chosen from $(C_1-C_6)$ alkylcarbonyl, carbamyl, and $(C_1-C_6)$ alkylsulphonyl;

$R'_1$, and $R'_2$ together can optionally form, with the nitrogen atom to which they are attached, a 5- or 7-membered saturated ring optionally containing at least one heteroatom wherein said 5- or 7-membered saturated ring is optionally substituted with at least one substituent chosen from halogen, hydroxyl, $C_1-C_6$ alkyl, $C_1-C_6$ (poly) hydroxyalkyl, nitro, cyano, $C_1-C_6$ cyanoalkyl, $C_1-C_6$ alkoxy, $(C_1-C_6)$ tri-alkylsilane $(C_1-C_6)$ alkyl, amido, aldehydro, —$CO_2H$, $C_1-C_6$ ketoalkyl, thio, $C_1-C_6$ thioalkyl, $(C_1-C_6)$ alkylthio, amino, N-amino $(C_1-C_6)$ alkylcarbonyl, N-amino carbamyl, and N-amino $(C_1-C_6)$ alkylsulphonyl;

$R'_3$ is chosen from —$CO_2H$ and linear or branched $C_1-C_6$ alkyl optionally substituted with at least one substituent chosen from hydroxyl, $C_1-C_2$ alkoxy, $C_1-C_4$ (poly) hydroxyalkoxy, amino, $C_1-C_2$ (di) alkylamino, carboxyl, $C_1-C_4$ alkyl carboxylate, sulphonic, $C_1-C_4$ alkyl sulphonate, optionally substituted phenyl, and sulphonylamino;

$A_1^-$ is chosen from an organic anion and an inorganic anion;

Z is chosen from —$NR_3R_4$; and —$OR_5$;

$R_1$, $R_2$, $R_3$, $R_4$, and $R_5$, which are identical or different, are independently selected from:
  $C_1-C_6$ alkyl optionally substituted with at least one substituent chosen from $OR_6$, $NR_7R_8$, —$CO_2H$, $C_1-C_4$ alkyl carboxylate, sulphonic, —$CONR_7R_8$, —$SO_2NR_7R_8$, 5- or 6-membered heteroaryl, and phenyl wherein said phenyl is optionally substituted with at least one substituent chosen from $(C_1-C_4)$ alkyl, hydroxyl, $C_1-C_2$ alkoxy, amino, $(C_1-C_2)$(di) alkylamino and $C_1-C_4$ hydroxyalkyl;
  phenyl optionally substituted with at least one substituent chosen from $(C_1-C_4)$ alkyl, hydroxy $(C_1-C_4)$alkyl, hydroxyl, $C_1-C_2$ alkoxy, amino, and $(C_1-C_2)$(di) alkylamino; and
  5- or 6-membered heteroaryls optionally substituted with at least one substituent chosen from $(C_1-C_4)$ alkyl and $(C_1-C_2)$ alkoxy;

$R_3$, $R_4$ and $R_5$ can also be H;

$R_6$, $R_7$ and $R_8$, which are identical or different, are independently selected from: H;

linear or branched $C_1-C_4$ alkyls optionally substituted with at least one substituent chosen from hydroxyl, $C_1-C_2$ alkoxy, —$CONR_9R_{10}$, —$SO_2R_9$, and phenyl wherein said phenyl is optionally substituted with at least one substituent chosen from $(C_1-C_4)$ alkyl, hydroxyl, $C_1-C_2$ alkoxy, amino, and $(C_1-C_2)$(di) alkylamino; and phenyls optionally substituted with at least one substituent chosen from $(C_1-C_4)$ alkyl, hydroxyl, $C_1-C_2$ alkoxy, amino, and $(C_1-C_2)$(di) alkylamino;

$R_7$ and $R_8$, which are identical or different, can also be chosen from —$C(O)NR_9R_{10}$ and —$SO_2R_9$;

—$R_9$ and $R_{10}$, which are identical or different, are independently selected from H and linear or branched $C_1-C_4$ alkyl optionally substituted with at least one substituent chosen from hydroxyl and $C_1-C_2$ alkoxy;

$R_1$ and $R_2$, on the one hand, and $R_3$ and $R_4$, on the other hand, can form with the nitrogen atoms to which they are attached a 5- to 7-membered saturated or unsaturated heterocycle whose carbon atoms may be replaced by an oxygen or nitrogen atom,
  wherein said saturated or unsaturated heterocycle is optionally substituted with at least one substituent chosen from halogen, amino, $(C_1-C_4)$(di) alkylamino, (di) hydroxy $(C_1-C_4)$ alkylamino, hydroxyl, carboxyl, carboxamido, $(C_1-C_4)$(di) alkylcarboxamido, $(C_1-C_2)$ alkoxy, and $C_1-C_4$ alkyl wherein said $C_1-C_4$ alkyl is optionally substituted with at least one substituent chosen from hydroxyl, amino, $(C_1-C_4)$(di) alkylamino, $C_1-C_2$ alkoxy, carboxyl, and sulphonyl;

with the proviso that the at least one azo pyrazolinone entity of formula (I) is not chosen from:

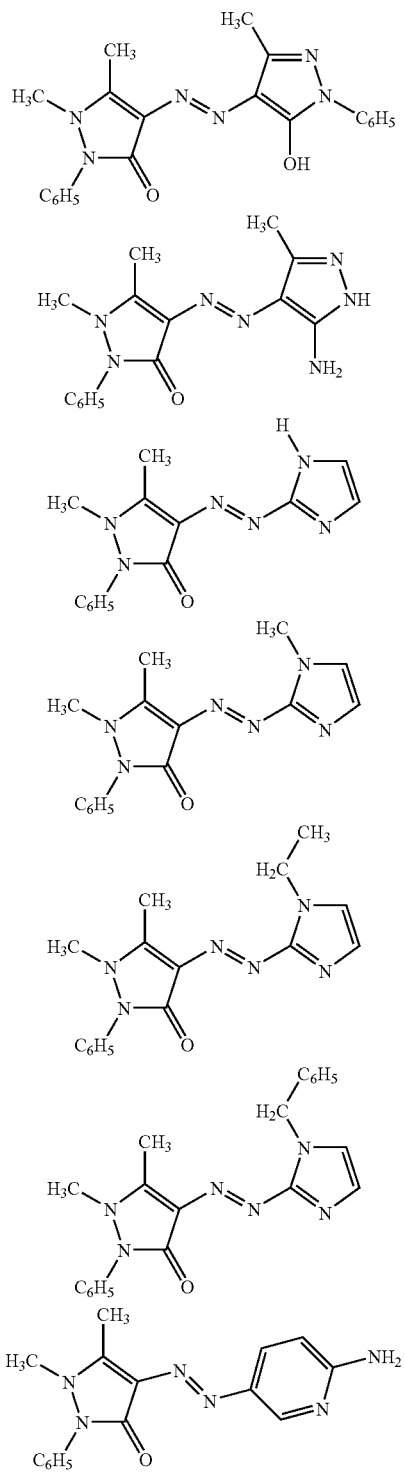

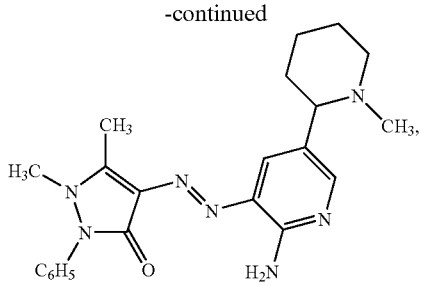

the mesomeric forms, acid addition salts, and solvates thereof.

2. The at least one azo pyrazolinone entity according to claim 1, wherein $R_1$ and $R_2$, which are identical or different, are chosen from:
  $C_1$-$C_4$ alkyl optionally substituted with at least one substituent chosen from hydroxyl, ($C_1$-$C_2$) alkoxy, amino, and ($C_1$-$C_2$)(di) alkylamino; and
  phenyl optionally substituted with at least one substituent chosen from $C_1$-$C_4$ alkyl and $C_1$-$C_4$ hydroxyalkyl.

3. The at least one azo pyrazolinone entity according to claim 2, wherein $R_1$ and $R_2$, which are identical or different, are chosen from methyl, ethyl, 2-hydroxyethyl, 3-hydroxypropyl, 2-hydroxypropyl and phenyl.

4. The at least one azo pyrazolinone entity according to claim 1, wherein $R_1$ and $R_2$ form together with the nitrogen atoms to which they are attached a saturated or unsaturated, optionally substituted 5- or 6-membered ring.

5. The at least one azo pyrazolinone entity according to claim 1, wherein $R_1$ and $R_2$ form together with the nitrogen atoms to which they are attached a pyrazolidine or pyridazolidine ring, optionally substituted with at least one substituent chosen from $C_1$-$C_4$ alkyl, hydroxyl, ($C_1$-$C_2$) alkoxy, carboxyl, carboxamido, amino, and ($C_1$-$C_2$)(di) alkylamino.

6. The at least one azo pyrazolinone entity according to claim 1, wherein $R_3$, $R_4$ and $R_5$, which are identical or different, are chosen from a hydrogen atom; $C_1$-$C_4$ alkyl optionally substituted with at least one substituent chosen from hydroxyl, ($C_1$-$C_2$) alkoxy, amino, ($C_1$-$C_2$)(di) alkylamino, carboxyl, and $C_1$-$C_4$ alkyl carboxylate; phenyl optionally substituted with at least one substituent chosen from hydroxyl, amino, and ($C_1$-$C_2$) alkoxy.

7. The at least one azo pyrazolinone entity according to claim 1, wherein $R_3$, $R_4$ and $R_5$, which are identical or different, are independently chosen from a hydrogen atom, methyl, ethyl, isopropyl, 2-hydroxyethyl, 3-hydroxy-propyl, 2-hydroxypropyl, ethyl substituted with an ethyl carboxylate radical moiety, and ethyl substituted with a carboxyl moiety.

8. The at least one azo pyrazolinone entity according to claim 7, wherein $R_3$, $R_4$ and $R_5$ are a hydrogen atom.

9. The at least one azo pyrazolinone entity according to claim 6, wherein $R_3$, $R_4$ and $R_5$, which are identical or different, are independently chosen from a hydrogen atom, methyl, ethyl, isopropyl, 2-hydroxyethyl, 3-hydroxy-propyl, 2-hydroxypropyl, ethyl substituted with an ethyl carboxylate radical moiety, and ethyl substituted with a carboxyl moiety.

10. The at least one azo pyrazolinone entity according to claim 9, wherein $R_3$, $R_4$ and $R_5$ are a hydrogen atom.

11. The at least one azo pyrazolinone entity according to claim 1, wherein $R_3$ and $R_4$ form together with the nitrogen atom to which they are attached a 5- to 7-membered ring chosen from pyrrolidine, piperidine, homopiperidine, piperazine and homopiperazine wherein said 5 to 7-membered ring is optionally substituted with at least one substituent chosen from hydroxyl, amino, ($C_1$-$C_2$)(di) alkylamino, ($C_1$-$C_2$)(di) hydroxyalkylamino, ($C_1$-$C_2$)(di) alkylcarboxamido, carboxyl, carboxamido, and $C_1$-$C_4$ alkyl wherein said optional at least one substituent is optionally substituted with at least one substituent chosen from hydroxyl, amino and $C_1$-$C_2$ (di) alkylamino.

12. The at least one azo pyrazolinone entity according to claim 11, wherein $R_3$ and $R_4$ form together with the nitrogen atom to which they are attached a 5- to 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxy-methylpyrrolidine, 2-carboxamidopyrrolidine, 3-hydroxy-2-carboxamidopyrrolidine, 2-(diethylcarboxamido)-pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methyl-aminopyrrolidine, 3-dimethylaminopyrrolidine, 4-amino-3-hydroxypyrrolidine, 3-hydroxy-4-(2-hydroxyethyl)-aminopyrrolidine, piperidine, 2,6-dimethylpiperidine, 2-carboxypiperidine, 2-carboxamidopiperidine, 2-hydroxymethylpiperidine, 3-hydroxy-2-hydroxymethyl-piperidine, 3-hydroxypiperidine, 4-hydroxypiperidine, 3-hydroxymethylpiperidine, homopiperidine, 2-carboxy-homopiperidine, 2-carboxamidohomopiperidine, homo-piperazine, N-methylhomopiperazine, and N-(2-hydroxyethyl)-homopiperazine.

13. The at least one azo pyrazolinone entity according to claim 1, wherein $W_1$ is chosen from aromatic heterocyclic groups of formula (III):

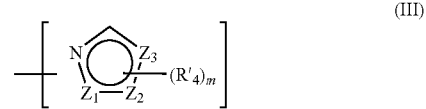

wherein:
  $Z_1$ is chosen from C—C, C and N;
  $Z_2$ is chosen from N and C;
  $Z_3$ is chosen from S, N and C;
  m is an integer ranging from 0 to 5;
  each $R'_4$ is independently selected from:
    $C_1$-$C_8$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, sulphonic, optionally substituted phenyl, and sulphonylamino;
    $C_1$-$C_4$ alkoxy;
    chlorine;
    nitro; and
    sulphonic
  wherein two $R'_4$ moieties attached to two adjacent atoms can optionally form with one another and with the atoms to which they are attached an optionally substituted, 5- or 6-membered aromatic or heteroaromatic ring.

14. The at least one azo pyrazolinone entity according to claim 1, wherein $W_1$ is chosen from cationic aromatic heterocyclic groups of formula (IV):

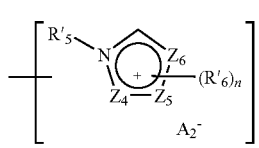

(IV)

wherein:
   $Z_4$ is chosen from C—C, C and N;
   $Z_5$ is chosen from N and C;
   $Z_6$ is chosen from S, N and C;
   n is an integer ranging from 0 to 5;
   $R'_5$ and $R'_6$ are independently selected from:
      $C_1$-$C_8$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, sulphonic, optionally substituted phenyl and sulphonylamino;
      $C_1$-$C_4$ alkoxy;
      chlorine;
      nitro; and
      sulphonic,
   wherein adjacent $R'_5$ and $R'_6$ can optionally form with one another and with the atoms to which they are attached an optionally substituted, 5- or 6-membered aromatic or heteroaromatic ring; and
   $A_2^-$ is chosen from an organic and inorganic anion.

15. The at least one azo pyrazolinone entity according to claim 1, wherein $W_1$ is phenyl substituted with an aromatic heterocyclic group chosen from those of formula (III):

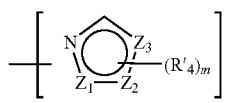

(III)

wherein:
   $Z_1$ is chosen from C—C, C and N;
   $Z_2$ is chosen from N and C;
   $Z_3$ is chosen from S, N and C;
   m is an integer ranging from 0 to 5;
   each $R'_4$ is independently selected from:
      $C_1$-$C_8$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, sulphonic, optionally substituted phenyl and sulphonylamino;
      $C_1$-$C_4$ alkoxy;
      chlorine;
      nitro; and
      sulphonic
   wherein two $R'_4$ moieties attached to two adjacent atoms can optionally form with one another and with the atoms to which they are attached an optionally substituted, 5- or 6-membered aromatic or heteroaromatic ring.

16. The at least one azo pyrazolinone entity according to claim 1, wherein $W_1$ is phenyl substituted with a cationic aromatic heterocyclic group chosen from those of formula (IV):

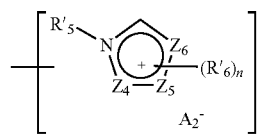

(IV)

wherein:
   $Z_4$ is chosen from C—C, C and N;
   $Z_5$ is chosen from N and C;
   $Z_6$ is chosen from S, N or C;
   n is an integer ranging from 0 to 5;
   $R'_5$ and $R'_6$ are independently selected from:
      $C_1$-$C_8$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, sulphonic, optionally substituted phenyl and sulphonylamino;
      $C_1$-$C_4$ alkoxy;
      chlorine;
      nitro; and
      sulphonic,
   wherein adjacent $R'_5$ and $R'_6$ can optionally form with one another and with the atoms to which they are attached an optionally substituted, 5- or 6-membered aromatic or heteroaromatic ring; and
   $A_2^-$ is chosen from an organic and inorganic anion.

17. The at least one azo pyrazolinone entity according to claim 1, wherein $W_1$ is phenyl substituted with $NR'_1$, $R'_2$ wherein $R'_1$ and $R'_2$ independently are chosen from carboxyl and $C_1$-$C_4$ alkyl wherein said $C_1$-$C_4$ alkyl is optionally substituted with at least one substituent chosen from hydroxyl, $C_1$-$C_2$ alkoxy, amino, $C_1$-$C_2$ (di) alkylamino, carboxyl, $C_1$-$C_4$ alkyl carboxylate, sulphonic, $C_1$-$C_4$ alkyl sulphonate, and phenyl.

18. The at least one azo pyrazolinone entity according to claim 1, wherein $W_1$ is phenyl substituted with a cationic quaternary ammonium moiety chosen from those of formula (II):

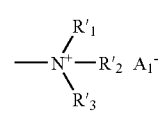

(II)

wherein:
   $R'_1$, $R'_2$ and $R'_3$ are independently chosen from carboxyl and $C_1$-$C_4$ alkyl wherein said $C_1$-$C_4$ alkyl is optionally substituted with at least one substituent chosen from hydroxyl, $C_1$-$C_2$ alkoxy, amino, $C_1$-$C_2$ (di) alkylamino, carboxyl, $C_1$-$C_4$ alkyl carboxylate, sulphonic, $C_1$-$C_4$ alkyl sulphonate, and phenyl; and
   $A_1^-$ is chosen from an organic anion and inorganic anion.

19. The at least one azo pyrazolinone entity according to claim 1, the mesomeric forms, acid addition salts, and solvates thereof, wherein the at least one azo pyrazolinone is chosen from:

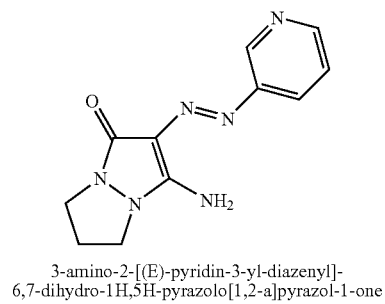

3-amino-2-[(E)-pyridin-3-yl-diazenyl]-
6,7-dihydro-1H,5H-pyrazolo[1,2-a]pyrazol-1-one

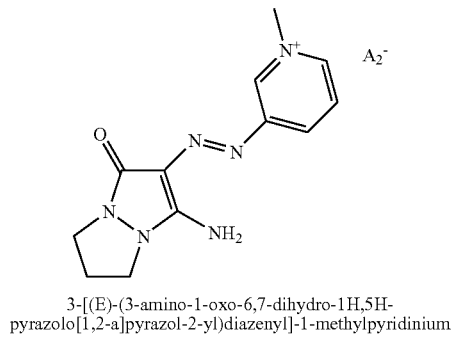

3-[(E)-(3-amino-1-oxo-6,7-dihydro-1H,5H-
pyrazolo[1,2-a]pyrazol-2-yl)diazenyl]-1-methylpyridinium

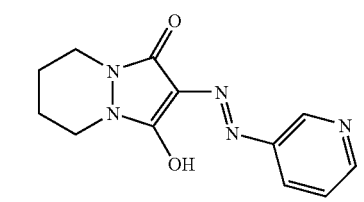

3-hydroxy-2-[(E)-pyridin-3-yl-diazenyl]-5,6,7,8-
tetrahydro-1H-pyrazolo[1,2-a]pyridazin-1-one

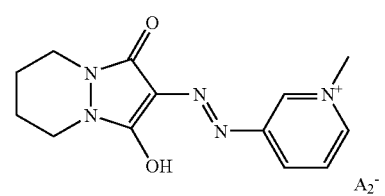

3-[(E)-(3-hydroxy-1-oxo-5,6,7,8-tetrahydro-
1H-pyrazolo[1,2-a]pyridazin-2-yl)-diazenyl]-1-methylpyridinium

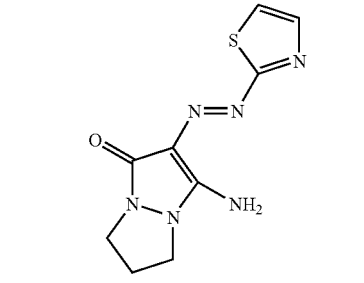

3-amino-2-[(E)-1,3-thiazol-2-yldiazenyl]-6,7-
dihydro-1H,5H-pyrazolo[1,2-a]pyrazol-1-one -continued

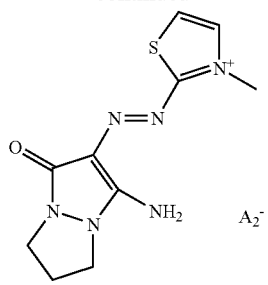

2-[(E)-(3-amino-1-oxo-6,7-dihydro-1H,5H-
pyrazolo[1,2-a]pyrazol-2-yl)diazenyl]-3-methyl-1,3-thiazol-3-ium

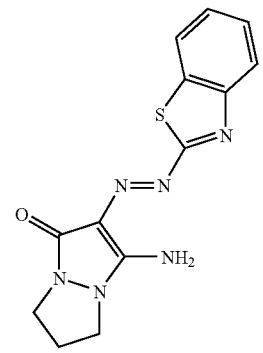

3-amino-2-[(E)-1,3-benzo-
thiazol-2-yldiazenyl]-6,7-
dihydro-1H,5H-pyrazolo[1,2-a]-
pyrazol-1-one

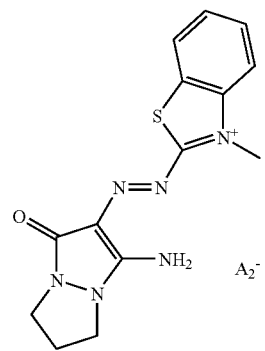

2-[(E)-(3-amino-1-oxo-6,7-
dihydro-1H,5H-pyrazolo[1,2-a]-
pyrazol-2-yl)diazenyl]-3-
methyl-1,3-benzothiazol-3-ium

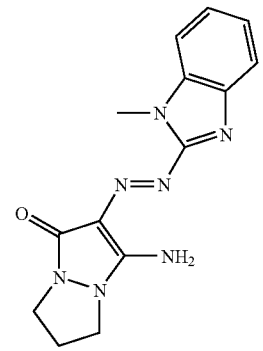

3-amino-2-[(E)-1-methyl-1H-
benzimidazol-2-yl)diazenyl]-
6,7-dihydro-1H,5H-pyrazolo[1,2-
a]pyrazol-1-one -continued

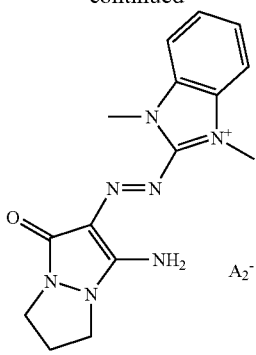

2-[(E)-(3-amino-1-oxo-6,7-
dihydro-1H,5H-pyrazolo[1,2-a]-
pyrazol-2-yl)diazenyl]-1,3-
dimethyl-1H-benzimidazol-3-ium

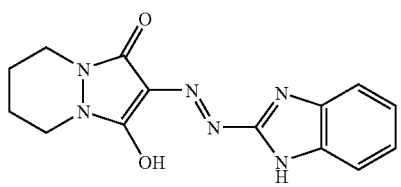

2-[(E)-1H-benzimidazol-2-yl-
diazenyl]-3-hydroxy-5,6,7,8-
tetrahydro-1H-pyrazolo[1,2-a]-
pyridazin-1-one

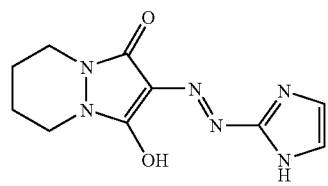

3-hydroxy-2-[(E)-1H-imidazol-
2-yldiazenyl]-5,6,7,8-tetra-
hydro-1H-pyrazolo[1,2-a]-
pyridazin-1-one

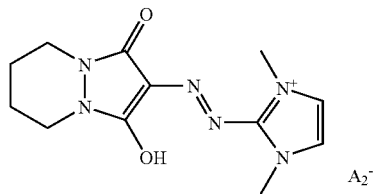

2-[(E)-(3-hydroxy-1-oxo-
5,6,7,8-tetrahydro-1H-pyrazolo-
[1,2-a]pyridazin-2-yl)-
diazenyl]-1,3-dimethyl-1H-
imidazol-3-ium

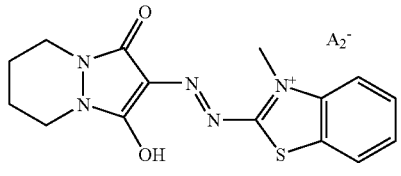

2-[(E)-(3-hydroxy-1-oxo-
5,6,7,8-tetrahydro-1H-pyrazolo-
[1,2-a]pyridazin-2-yl)-
diazenyl]-3-methyl-1,3-benzo-
thiazol-3-ium -continued

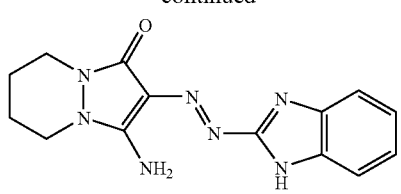

3-amino-2-[(E)-1H-benzimidazol-
2-yldiazenyl]-5,6,7,8-tetra-
hydro-1H-pyrazolo[1,2-a]-
pyridazin-1-one

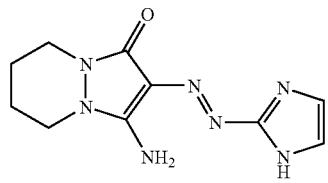

3-amino-2-[(E)-1H-imidazol-
2-yldiazenyl]-5,6,7,8-tetra-
hydro-1H-pyrazolo[1,2-a]-
pyridazin-1-one

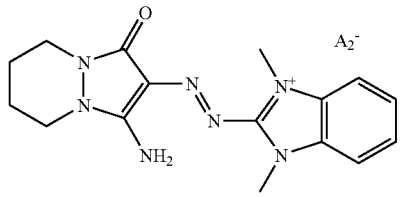

2-[(E)-(3-amino-1-oxo-5,6,7,8-
tetrahydro-1H-pyrazolo[1,2-a]-
pyridazin-2-yl)diazenyl]-1,3-
dimethyl-1H-3,1-benzimidazol-3-ium

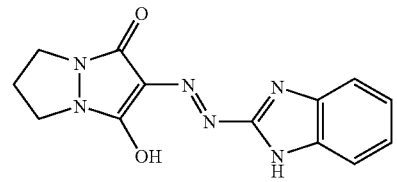

2-[(E)-1H-benzimidazol-2-yl-
diazenyl]-3-hydroxy-6,7-
dihydro-1H,5H-pyrazolo[1,2-a]-
pyrazol-1-one

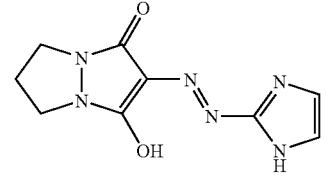

3-hydroxy-2-[(E)-1H-imidazol-2-
yldiazenyl]-6,7-dihydro-1H,5H-
pyrazolo[1,2-a]pyrazol-1-one

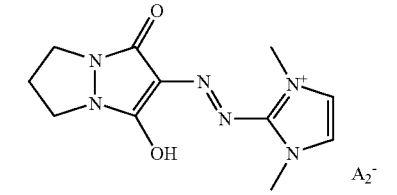

2-[(E)-(3-hydroxy-1-oxo-
6,7-dihydro-1H,5H-pyrazolo-[1,2-a]-
pyrazol-2-yl)-diazenyl]-1,3-
dimethyl-1H-imidazol-3-ium -continued

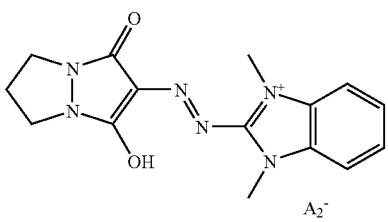

2-[(E)-(3-hydroxy-1-oxo-
6,7-dihydro-1H,5H-pyrazolo-[1,2-a]-
pyrazol-2-yl)-diazenyl]-1,3-
dimethyl-1H-3,1-benzimidazol-3-ium

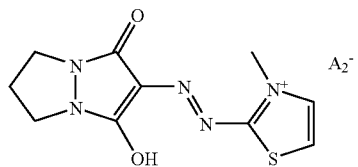

2-[(E)-(3-hydroxy-1-oxo-
6,7-dihydro-1H,5H-pyrazolo-[1,2-a]-
pyrazol-2-yl)-diazenyl]-3-
methyl-1,3-thiazol-3-ium

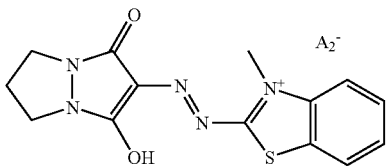

2-[(E)-(3-hydroxy-1-oxo-6,7-
dihydro-1H,5H-pyrazolo[1,2-a]-
pyrazol-2-yl)diazenyl]-3-
methyl-1,3-benzothiazol-3-ium

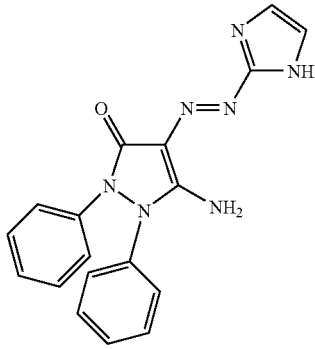

5-amino-4-[(E)-1H-imidazol-2-
yldiazenyl]-1,2-diphenyl-1,2-
dihydro-3H-pyrazol-3-one

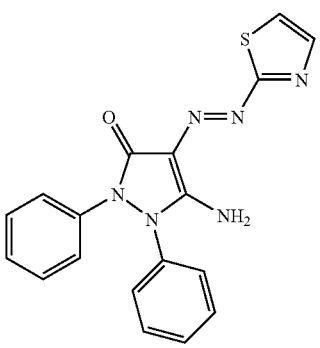

5-amino-1,2-diphenyl-4-[(E)-
1,3-thiazol-2-yldiazenyl]-1,2-
dihydro-3H-pyrazol-3-one -continued

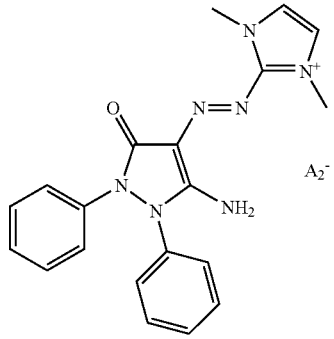

2-[(E)-(5-amino-3-oxo-1,2-
diphenyl-2,3-dihydro-1H-
pyrazol-4-yl)diazenyl]-1,3-
dimethyl-1H-imidazol-3-ium

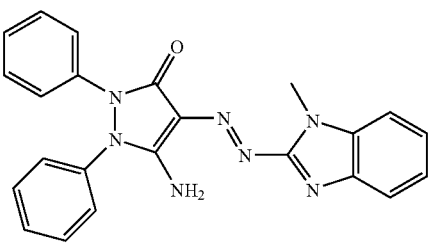

5-amino-4-[(E)-(1-methyl-1H-
benzimidazol-2-yl)diazenyl]-
1,2-diphenyl-1,2-dihydro-3H-
pyrazol-3-one

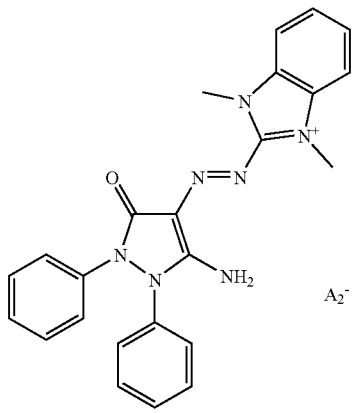

2-[(E)-(5-amino-3-oxo-1,2-
diphenyl-2,3-dihydro-1H-
pyrazol-4-yl)diazenyl]-1,3-
dimethyl-1H-benzimidazol-3-ium

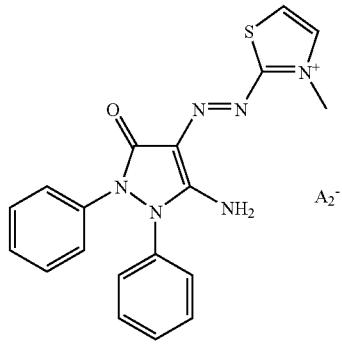

2-[(E)-(5-amino-3-oxo-1,2-
diphenyl-2,3-dihydro-1H-
pyrazol-4-yl)diazenyl]-3-
methyl-1,3-thiazol-3-ium -continued

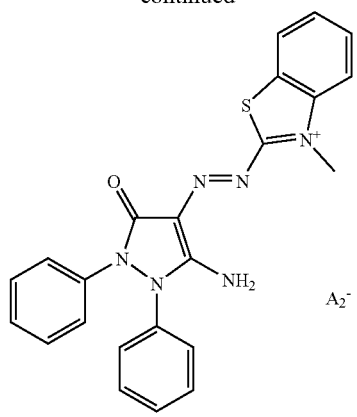

2-[(E)-(5-amino-3-oxo-1,2-diphenyl-2,3-dihydro-1H-pyrazol-4-yl)diazenyl]-3-methyl-1,3-benzothiazol-3-ium

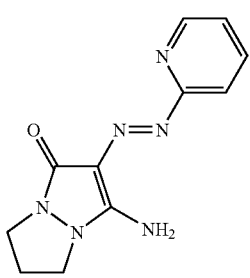

3-amino-2-[(E)-pyridin-2-yl-diazenyl]-6,7-dihydro-1H,5H-pyrazolo[1,2-a]pyrazol-1-one

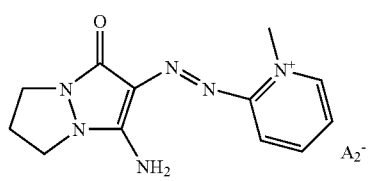

2-[(E)-(3-amino-1-oxo-6,7-dihydro-1H,5H-pyrazolo[1,2-a]pyrazol-2-yl)diazenyl]-1-methylpyridinium

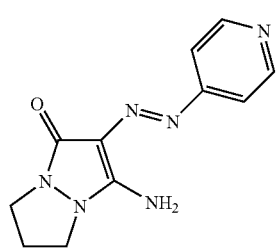

3-amino-2-[(E)-pyridin-4-yl-diazenyl]-6,7-dihydro-1H,5H-pyrazolo[1,2-a]pyrazol-1-one -continued

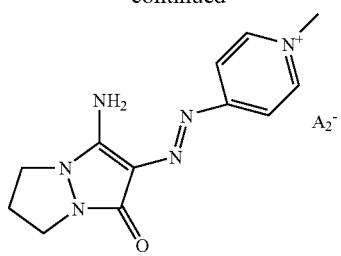

4-[(E)-(3-amino-1-oxo-6,7-dihydro-1H,5H-pyrazolo[1,2-a]-pyrazol-2-yl)diazenyl]-1-methylpyridinium

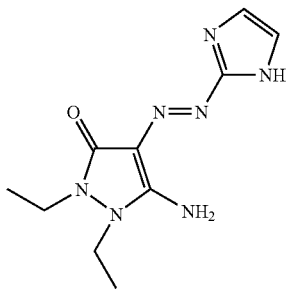

5-amino-4-[(E)-1H-imidazol-2-yldiazenyl]-1,2-diethyl-1,2-dihydro-3H-pyrazol-3-one

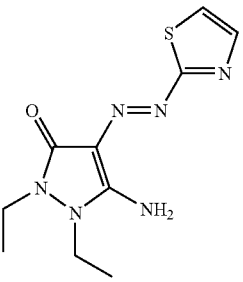

5-amino-1,2-diethyl-4-[(E)-1,3-thiazol-2-yldiazenyl]-1,2-dihydro-3H-pyrazol-3-one

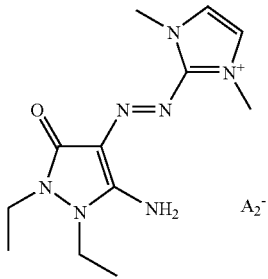

2-[(E)-(5-amino-3-oxo-1,2-diethyl-2,3-dihydro-1H-pyrazol-4-yl)diazenyl]-1,3-dimethyl-1H-imidazol-3-ium

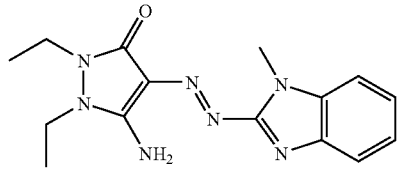

5-amino-4-[(E)-(1-methyl-1H-benzimidazol-2-yl)diazenyl]-1,2-diethyl-1,2-dihydro-3H-pyrazol-3-one

| 71 | 72 |
|---|---|
| -continued | -continued |

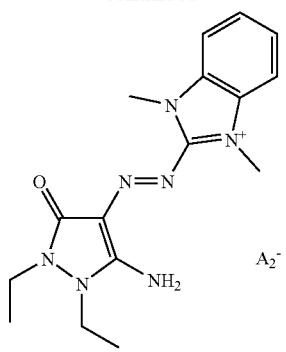

2-[(E)-(5-amino-3-oxo-1,2-
diethyl-2,3-dihydro-1H-pyrazol-
4-yl)diazenyl]-1,3-dimethyl-1H-
benzimidazol-3-ium

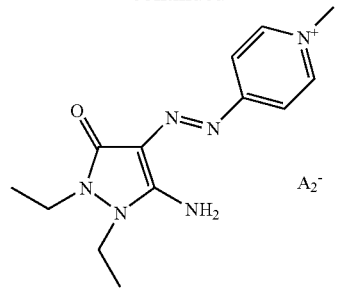

4-[(E)-(5-amino-1,2-diethyl-3-
oxo-2,3-dihydro-1H-pyrazol-4-
yl)diazenyl]-1-methylpyridinium

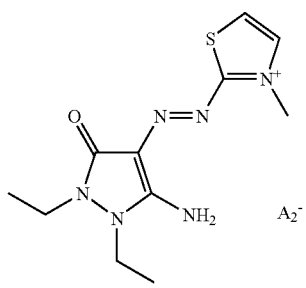

2-[(E)-(5-amino-3-oxo-1,2-
diethyl-2,3-dihydro-1H-pyrazol-
4-yl)diazenyl]-3-methyl-1,3-
thiazol-3-ium

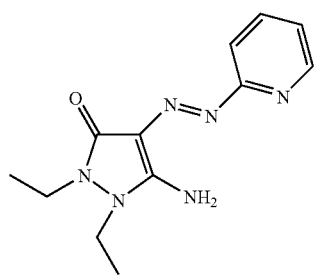

5-amino-1,2-diethyl-4-[(E)-
pyridin-2-yldiazenyl]-1,2-
dihydro-3H-pyrazol-3-one

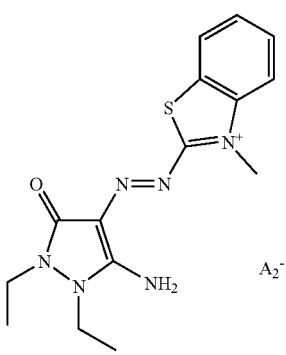

2-[(E)-(5-amino-3-oxo-1,2-
diethyl-2,3-dihydro-1H-pyrazol-
4-yl)diazenyl]-3-methyl-1,3-
benzothiazol-3-ium

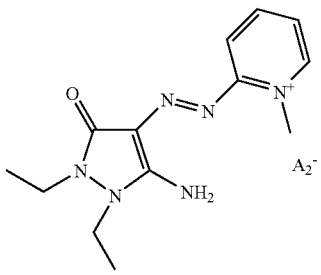

2-[(E)-(5-amino-1,2-diethyl-3-
oxo-2,3-dihydro-1H-pyrazol-4-
yl)diazenyl]-1-methylpyridinium

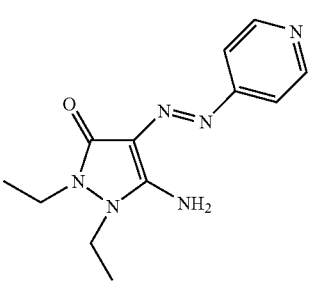

5-amino-1,2-diethyl-4-[(E)-
pyridin-4-yldiazenyl]-1,2-
dihydro-3H-pyrazol-3-one

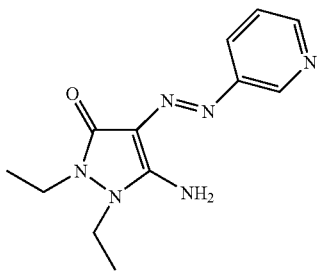

5-amino-1,2-diethyl-4-[(E)-
pyridin-3-yldiazenyl]-1,2-
dihydro-3H-pyrazol-3-one

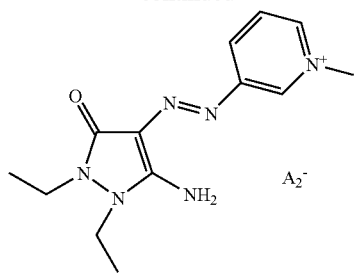

3-[(E)-(5-amino-1,2-diethyl-3-oxo-2,3-dihydro-1H-pyrazol-4-yl)diazenyl]-1-methylpyridinium

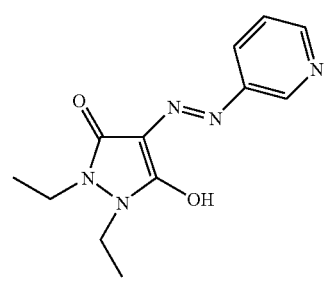

1,2-diethyl-5-hydroxy-4-[(E)-pyridin-3-yldiazenyl]-1,2-dihydro-3H-pyrazol-3-one

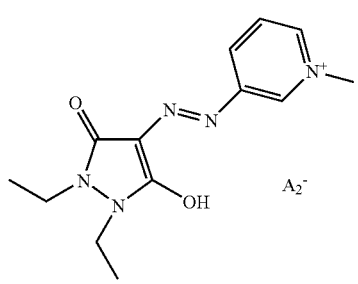

3-[(E)-(1,2-diethyl-5-hydroxy-3-oxo-2,3-dihydro-1H-pyrazol-4-yl)diazenyl]-1-methylpyridinium

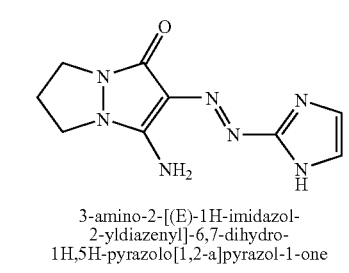

3-amino-2-[(E)-1H-imidazol-2-yldiazenyl]-6,7-dihydro-1H,5H-pyrazolo[1,2-a]pyrazol-1-one

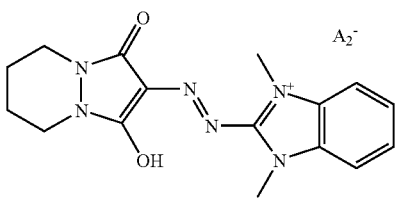

2-[(E)-(3-hydroxy-1-oxo-5,6,7,8-tetrahydro-1H-pyrazolo-[1,2-a]pyridazin-2-yl)-diazenyl]-1,3-dimethyl-1H-3,1-benzimidazol-3-ium

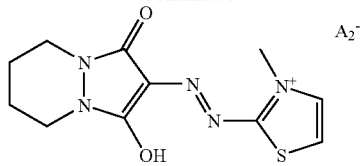

2-[(E)-(3-hydroxy-1-oxo-5,6,7,8-tetrahydro-1H-pyrazolo-[1,2-a]pyridazin-2-yl)-diazenyl]-3-methyl-1,3-thiazol-3-ium

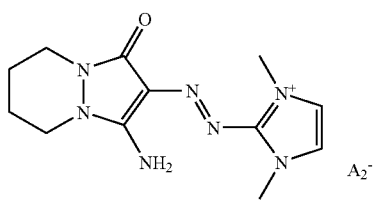

2-[(E)-(3-amino-1-oxo-5,6,7,8-tetrahydro-1H-pyrazolo[1,2-a]-pyridazin-2-yl)diazenyl]-1,3-dimethyl-1H-imidazol-3-ium

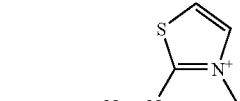

2-[(E)-(3-amino-1-oxo-5,6,7,8-tetrahydro-1H-pyrazolo[1,2-a]-pyridazin-2-yl)-diazenyl]-3-methyl-1,3-thiazol-3-ium

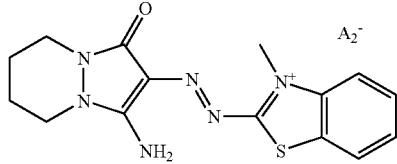

2-[(E)-(3-amino-1-oxo-5,6,7,8-tetrahydro-1H-pyrazolo[1,2-a]-pyridazin-2-yl)diazenyl]-3-methyl-1,3-benzothiazol-3-ium wherein $A_2^-$ is chosen from an organic anion or an inorganic anion.

20. A composition for dyeing keratin fibres comprising, in an appropriate medium for dyeing, at least one azo pyrazolinone entity chosen from those of formula (I):

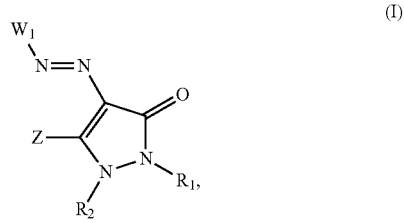

(I)

the mesomeric forms, acid addition salts, and solvates thereof, wherein:

$W_1$ is attached to the azo functional group via a carbon and is chosen from:
aromatic heterocyclic groups chosen from imidazole, benzimidazole, pyrazole, thiazole, benzothiazole, pyridine, pyrimidine, pyrazine, and pyridazine rings wherein said aromatic heterocyclic group is optionally substituted with at least one substituent;
cationic aromatic heterocyclic groups chosen from imidazolium, benzimidazolium, pyrazolium, thiazolium, benzothiazolium, pyridinium, pyrimidinium, pyrazinium, and pyridazinium rings wherein said cationic aromatic heterocyclic group is substituted with at least one substituent, one of the substituents being carried by a nitrogen atom and combined with an organic or inorganic anion; and
phenyls substituted with a substituent chosen from:
an aromatic heterocyclic group chosen from imidazole, benzimidazole, pyrazole, thiazole, benzothiazole, pyridine, pyrimidinine, pyrazine and pyridazine rings wherein said aromatic heterocyclic group is optionally substituted with at least one substituent;
a cationic aromatic heterocyclic group chosen from imidazolium, benzimidazolium, pyrazolium, thiazolium, benzothiazolium, pyridinium, pyrimidinium, pyrazinium and pyridazinium rings wherein said cationic aromatic heterocyclic group is substituted with at least one substituent, one of the substituents being carried by a nitrogen atom and combined with an organic or inorganic anion;
$NR'_1R'_2$; and
cationic quaternary ammonium moieties chosen from those of formula (II):

(II)

wherein:
$R'_1$ and $R'_2$, which are identical or different, are independently selected from —$CO_2H$, —$C_1$-$C_6$ alkyl optionally substituted with at least one substituent chosen from phenyl, hydroxyl, ($C_1$-$C_6$) alkoxy, cyano, amino, ($C_1$-$C_6$)(di) alkylamino, —$CO_2H$, $C_1$-$C_6$ alkyl carboxylate, sulphonic, and $C_1$-$C_6$ alkyl sulphonate; phenyl, benzyl, $C_1$-$C_6$ amidoalkyl, ($C_1$-$C_6$) trialkylsilane ($C_1$-$C_6$) alkyl, and $C_1$-$C_6$ aminoalkyl wherein said $C_1$-$C_6$ aminoalkyl is N-protected by a moiety chosen from ($C_1$-$C_6$) alkylcarbonyl, carbamyl, and ($C_1$-$C_6$) alkylsulphonyl;
$R'_1$ and $R'_2$ together can optionally form, with the nitrogen atom to which they are attached, a 5- or 7-membered saturated ring optionally containing at least one heteroatom wherein said 5- or 7-membered saturated ring is optionally substituted with at least one substituent chosen from halogen, hydroxyl, $C_1$-$C_6$ alkyl, $C_1$-$C_6$ (poly) hydroxyalkyl, nitro, cyano, $C_1$-$C_6$ cyanoalkyl, $C_1$-$C_6$ alkoxy, ($C_1$-$C_6$) tri-alkylsilane ($C_1$-$C_6$) alkyl, amido, aldehydro, —$CO_2H$, $C_1$-$C_6$ ketoalkyl, thio, $C_1$-$C_6$ thioalkyl, ($C_1$-$C_6$) alkylthio, amino, N-amino ($C_1$-$C_6$) alkylcarbonyl, N-amino carbamyl, and N-amino ($C_1$-$C_6$) alkylsulphonyl;
$R'_3$ is chosen from —$CO_2H$ and linear or branched $C_1$-$C_6$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, $C_1$-$C_4$ alkyl carboxylate, sulphonic, $C_1$-$C_4$ alkyl sulphonate, optionally substituted phenyl, and sulphonylamino;
$A_1^-$ is chosen from an organic anion and an inorganic anion;
Z is chosen from —$NR_3R_4$; and —$OR_5$;
$R_1$, $R_2$, $R_3$, $R_4$, and $R_5$, which are identical or different, are independently selected from:
$C_1$-$C_6$ alkyl optionally substituted with at least one substituent chosen from $OR_6$, $NR_7R_8$, —$CO_2H$, $C_1$-$C_4$ alkyl carboxylate, sulphonic, —$CONR_7R_8$, —$SO_2NR_7R_8$, 5- or 6-membered heteroaryl, and phenyl wherein said phenyl is optionally substituted with at least one substituent chosen from ($C_1$-$C_4$) alkyl, hydroxyl, $C_1$-$C_2$ alkoxy, amino, ($C_1$-$C_2$)(di) alkylamino and $C_1$-$C_4$ hydroxyalkyl;
phenyl optionally substituted with at least one substituent chosen from ($C_1$-$C_4$) alkyl, hydroxy ($C_1$-$C_4$)alkyl, hydroxyl, $C_1$-$C_2$ alkoxy, amino, and ($C_1$-$C_2$)(di) alkylamino; and
5- or 6-membered heteroaryls optionally substituted with at least one substituent chosen from ($C_1$-$C_4$) alkyl and ($C_1$-$C_2$) alkoxy;
$R_3$, $R_4$ and $R_5$ can also be H;
$R_6$, $R_7$ and $R_8$, which are identical or different, are independently selected from:
H;
linear or branched $C_1$-$C_4$ alkyls optionally substituted with at least one substituent chosen from hydroxyl, $C_1$-$C_2$ alkoxy, —$CONR_9R_{10}$, —$SO_2R_9$, and phenyl wherein said phenyl is optionally substituted with at least one substituent chosen from ($C_1$-$C_4$) alkyl, hydroxyl, $C_1$-$C_2$ alkoxy, amino, and ($C_1$-$C_2$)(di) alkylamino; and phenyls optionally substituted with at least one substituent chosen from ($C_1$-$C_4$) alkyl, hydroxyl, $C_1$-$C_2$ alkoxy, amino, and ($C_1$-$C_2$)(di) alkylamino;
$R_7$ and $R_8$, which are identical or different, can also be chosen from —$C(O)NR_9R_{10}$ and —$SO_2R_9$;
$R_9$ and $R_{10}$, which are identical or different, are independently selected from H and linear or branched $C_1$-$C_4$ alkyls optionally substituted with at least one substituent chosen from hydroxyl and $C_1$-$C_2$ alkoxy;
$R_1$ and $R_2$, on the one hand, and $R_3$ and $R_4$, on the other hand, can form with the nitrogen atoms to which they are attached a 5- to 7-membered saturated or unsaturated heterocycle whose carbon atoms may be replaced by an oxygen or nitrogen atom, wherein said saturated or unsaturated heterocycle is optionally substituted with at least one substituent chosen from halogen, amino, ($C_1$-$C_4$)(di) alkylamino, (di) hydroxy ($C_1$-$C_4$) alkylamino, hydroxyl, carboxyl, carboxamido, ($C_1$-$C_4$)(di) alkylcarboxamido, ($C_1$-$C_2$) alkoxy, and $C_1$-$C_4$ alkyl wherein said $C_1$-$C_4$ alkyl is optionally substituted with at least one substituent chosen from hydroxyl, amino, ($C_1$-$C_4$)(di) alkylamino, $C_1$-$C_2$ alkoxy, carboxyl, and sulphonyl;
with the proviso that the at least one azo pyrazolinone entity of formula (I) is not chosen from:

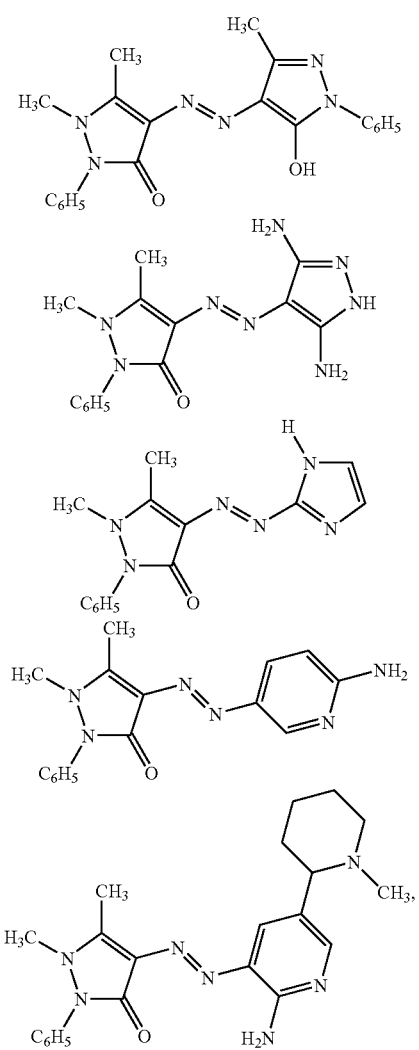

the mesomeric forms, acid addition salts, and solvates thereof.

21. The composition according to claim 20, comprising at least one oxidation base chosen from para-phenylenediamines, bis-phenylalkylenediamines, para-aminophenols, ortho-aminophenols, and heterocyclic bases.

22. The composition according to claim 20, wherein the at least one azo pyrazolinone entity is present in an amount ranging from 0.01 to 5% by weight of the total weight of the composition.

23. The composition according to claim 21, comprising at least one coupler chosen from meta-phenylenediamines, meta-aminophenols, meta-diphenols, naphthalene couplers and heterocyclic couplers.

24. The composition according to claim 20, comprising at least one additional direct dye.

25. The composition according to claim 24, wherein the at least one additional direct dye is chosen from nitrobenzene dyes, azo, azomethine, methine, tetraazapentamethine, anthraquinone, naphthoquinone, benzoquinone, pheno-thiazine, indigoid, xanthene, phenanthridine dyes, phthalocyanine dyes, those derived from triarylmethane, and natural dyes.

26. The composition according to claim 20, wherein the composition comprises at least one additive chosen from anionic, cationic, non-ionic, amphoteric and zwitterionic surfactants; anionic, cationic, non-ionic, amphoteric and zwitterionic polymers; inorganic and organic thickening agents; antioxidants; penetrating agents; sequestering agents; perfumes; buffers; dispersing agents; conditioning agents; film-forming agents; ceramides; preservatives; stabilizers; and opacifying agents.

27. The composition according to claim 20, comprising at least one oxidizing agent.

28. A method for dyeing keratin fibres, comprising applying a dye composition to wet or dry keratin fibers to be dyed wherein the dye composition comprises, in an appropriate medium for dyeing, at least one direct dye chosen from at least one azo pyrazolinone entity chosen from those of formula (I):

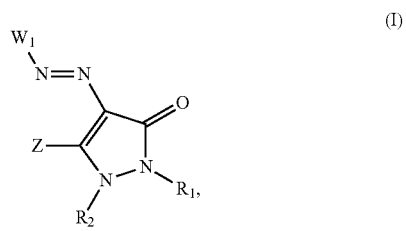

the mesomeric forms, acid addition salts, and solvates thereof, wherein:

$W_1$ is attached to the azo functional group via a carbon and is chosen from:

aromatic heterocyclic groups chosen from imidazole, benzimidazole, pyrazole, thiazole, benzothiazole, pyridine, pyrimidine, pyrazine, and pyridazine rings wherein said aromatic heterocyclic group is optionally substituted with at least one substituent;

cationic aromatic heterocyclic groups chosen from imidazolium, benzimidazolium, pyrazolium, thiazolium, benzothiazolium, pyridinium, pyrimidinium, pyrazinium, and pyridazinium rings wherein said cationic aromatic heterocyclic group is substituted with at least one substituent, one of the substituents being carried by a nitrogen atom and combined with an organic or inorganic anion; and phenyls substituted with a substituent chosen from:

an aromatic heterocyclic group chosen from imidazole, benzimidazole, pyrazole, thiazole, benzothiazole, pyridine, pyrimidinine, pyrazine and pyridazine rings wherein said aromatic heterocyclic group is optionally substituted with at least one substituent;

a cationic aromatic heterocyclic group chosen from imidazolium, benzimidazolium, pyrazolium, thiazolium, benzothiazolium, pyridinium, pyrimidinium, pyrazinium and pyridazinium rings wherein said cationic aromatic heterocyclic group is substituted with at least one substituent, one of the substituents being carried by a nitrogen atom and combined with an organic or inorganic anion;

$NR'_1R'_2$; and a cationic quaternary ammonium moiety chosen from those of formula (II):

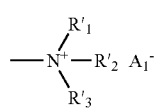
(II)

wherein:
R'₁ and R'₂, which are identical or different, are independently selected from —CO₂H, —C₁-C₆ alkyl optionally substituted with at least one substituent chosen from phenyl, hydroxyl, (C₁-C₆) alkoxy, cyano, amino, (C₁-C₆)(di) alkylamino, —CO₂H, C₁-C₆ alkyl carboxylate, sulphonic, and C₁-C₆ alkyl sulphonate; phenyl, benzyl, C₁-C₆ amidoalkyl, (C₁-C₆) trialkyl-silane (C₁-C₆) alkyl, and C₁-C₆ aminoalkyl wherein said C₁-C₆ aminoalkyl is N-protected by a moiety chosen from (C₁-C₆) alkylcarbonyl, carbamyl, and (C₁-C₆) alkylsulphonyl;
R'₁ and R'₂ together can optionally form, with the nitrogen atom to which they are attached, a 5- or 7-membered saturated ring optionally containing at least one heteroatom wherein said 5- or 7-membered saturated ring is optionally substituted with at least one substituent chosen from halogen, hydroxyl, C₁-C₆ alkyl, C₁-C₆ (poly) hydroxyalkyl, nitro, cyano, C₁-C₆ cyanoalkyl, C₁-C₆ alkoxy, (C₁-C₆) tri-alkylsilane (C₁-C₆) alkyl, amido, aldehydro, —CO₂H, C₁-C₆ ketoalkyl, thio, C₁-C₆ thioalkyl, (C₁-C₆) alkylthio, amino, N-amino (C₁-C₆) alkylcarbonyl, N-amino carbamyl, and N-amino (C₁-C₆) alkylsulphonyl;
R'₃ is chosen from —CO₂H and linear or branched C₁-C₆ alkyl optionally substituted with at least one substituent chosen from hydroxyl, C₁-C₂ alkoxy, C₁-C₄ (poly) hydroxyalkoxy, amino, C₁-C₂ (di) alkylamino, carboxyl, C₁-C₄ alkyl carboxylate, sulphonic, C₁-C₄ alkyl sulphonate, optionally substituted phenyl, and sulphonylamino;
$A_1^-$ is chosen from an organic anion or an inorganic anion;
Z is chosen from —NR₃R₄; and —OR₅;
R₁, R₂, R₃, R₄, and R₅, which are identical or different, are independently selected from:
  C₁-C₆ alkyls optionally substituted with at least one substituent chosen from OR₆, NR₇R₈, —CO₂H, C₁-C₄ alkyl carboxylate, sulphonic, —CONR₇R₈, —SO₂NR₇R₈, 5- or 6-membered heteroaryl, and phenyl wherein said phenyl is optionally substituted with at least one substituent chosen from (C₁-C₄) alkyl, hydroxyl, C₁-C₂ alkoxy, amino, (C₁-C₂)(di) alkylamino and C₁-C₄ hydroxyalkyl;
  phenyls optionally substituted with at least one substituent chosen from (C₁-C₄) alkyl, hydroxy (C₁-C₄)alkyl, hydroxyl, C₁-C₂ alkoxy, amino, and (C₁-C₂)(di) alkylamino; and
  5- or 6-membered heteroaryls optionally substituted with at least one substituent chosen from (C₁-C₄) alkyl and (C₁-C₂) alkoxy;
R₃, R₄ and R₅ can also be H;
R₆, R₇ and R₈, which are identical or different, are independently selected from:
  H;
  linear or branched C₁-C₄ alkyl optionally substituted with at least one substituent chosen from hydroxyl, C₁-C₂ alkoxy, —CONR₉R₁₀, —SO₂R₉, and phenyl wherein said phenyl is optionally substituted with at least one substituent chosen from (C₁-C₄) alkyl, hydroxyl, C₁-C₂ alkoxy, amino, and (C₁-C₂)(di) alkylamino; and phenyls optionally substituted with at least one substituent chosen from (C₁-C₄) alkyl, hydroxyl, C₁-C₂ alkoxy, amino, and (C₁-C₂)(di) alkylamino;

R₇ and R₈, which are identical or different, can also be chosen from —C(O)NR₉R₁₀ and —SO₂R₉;
R₉ and R₁₀, which are identical or different, are independently selected from H and linear or branched C₁-C₄ alkyl optionally substituted with at least one substituent chosen from hydroxyl and C₁-C₂ alkoxy;
R₁ and R₂, on the one hand, and R₃ and R₄, on the other hand, can form with the nitrogen atoms to which they are attached a 5- to 7-membered saturated or unsaturated heterocycle whose carbon atoms may be replaced by an oxygen or nitrogen atom, wherein said saturated or unsaturated heterocycle is optionally substituted with at least one substituent chosen from halogen, amino, (C₁-C₄)(di) alkylamino, (di) hydroxy (C₁-C₄) alkylamino, hydroxyl, carboxyl, carboxamido, (C₁-C₄)(di) alkylcarboxamido, (C₁-C₂) alkoxy, and C₁-C₄ alkyl wherein said C₁-C₄ alkyl is optionally substituted with at least one substituent chosen from hydroxyl, amino, (C₁-C₄)(di) alkylamino, C₁-C₂ alkoxy, carboxyl, and sulphonyl;
with the proviso that the at least one azo pyrazolinone entity of formula (I) is not chosen from:

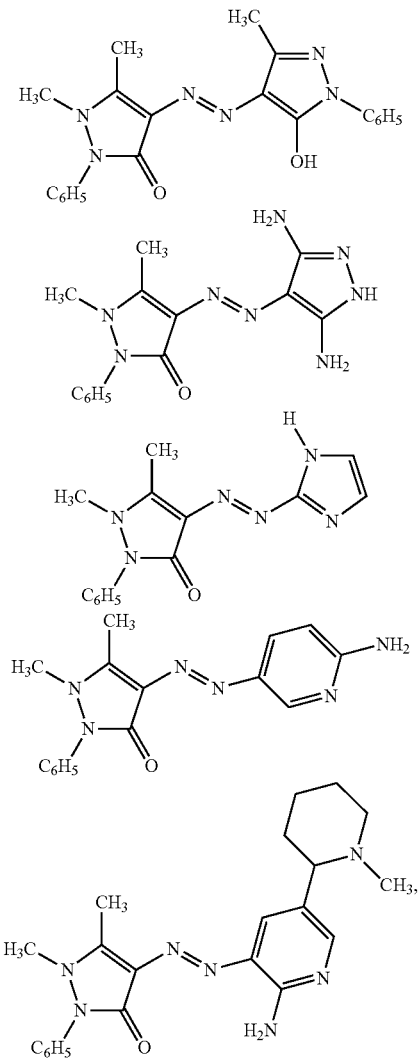

the mesomeric forms, acid addition salts, and solvates thereof; and
leaving the dye composition in contact with said fibres for a sufficient period of time to obtain the desired effect.

29. A multicompartment device comprising
at least one first compartment and at least one second compartment,
wherein the at least one first compartment comprises a composition comprising, in an appropriate medium for dyeing, at least one direct dye chosen from at least one azo pyrazolinone entity chosen from those of formula (I):

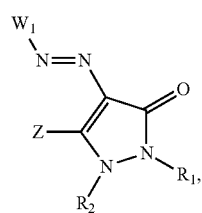

the mesomeric forms, acid addition salts, and solvates thereof, wherein:
$W_1$ is attached to the azo functional group via a carbon and is chosen from:
  aromatic heterocyclic groups chosen from imidazole, benzimidazole, pyrazole, thiazole, benzothiazole, pyridine, pyrimidine, pyrazine, and pyridazine rings wherein said aromatic heterocyclic group is optionally substituted with at least one substituent;
  cationic aromatic heterocyclic groups chosen from imidazolium, benzimidazolium, pyrazolium, thiazolium, benzothiazolium, pyridinium, pyrimidinium, pyrazinium, and pyridazinium rings wherein said cationic aromatic heterocyclic group is substituted with at least one substituent, one of the substituents being carried by a nitrogen atom and combined with an organic or inorganic anion; and
phenyls substituted with a substituent chosen from:
  an aromatic heterocyclic group chosen from imidazole, benzimidazole, pyrazole, thiazole, benzothiazole, pyridine, pyrimidinine, pyrazine and pyridazine rings wherein said aromatic heterocyclic group is optionally substituted with at least one substituent;
  a cationic aromatic heterocyclic group chosen from imidazolium, benzimidazolium, pyrazolium, thiazolium, benzothiazolium, pyridinium, pyrimidinium, pyrazinium and pyridazinium rings wherein said cationic aromatic heterocyclic group is substituted with at least one substituent, one of the substituents being carried by a nitrogen atom and combined with an organic or inorganic anion;
$NR'_1R'_2$; and
a cationic quaternary ammonium moiety chosen from those of formula (II):

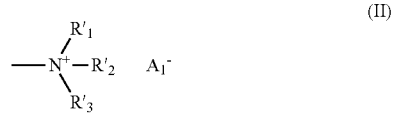

wherein:
$R'_1$ and $R'_2$, which are identical or different, are independently selected from $-CO_2H$, $-C_1$-$C_6$ alkyl optionally substituted with at least one substituent chosen from phenyl, hydroxyl, ($C_1$-$C_6$) alkoxy, cyano, amino, ($C_1$-$C_6$)(di) alkylamino, $-CO_2H$, $C_1$-$C_6$ alkyl carboxylate, sulphonic, and $C_1$-$C_6$ alkyl sulphonate; phenyl, benzyl, $C_1$-$C_6$ amidoalkyl, ($C_1$-$C_6$) trialkylsilane ($C_1$-$C_6$) alkyl, and $C_1$-$C_6$ aminoalkyl wherein said $C_1$-$C_6$ aminoalkyl is N-protected by a moiety chosen from ($C_1$-$C_6$) alkylcarbonyl, carbamyl, and ($C_1$-$C_6$) alkylsulphonyl;
$R'_1$ and $R'_2$ together can optionally form, with the nitrogen atom to which they are attached, a 5- or 7-membered saturated ring optionally containing at least one heteroatom wherein said 5- or 7-membered saturated ring is optionally substituted with at least one substituent chosen from halogen, hydroxyl, $C_1$-$C_6$ alkyl, $C_1$-$C_6$ (poly) hydroxyalkyl, nitro, cyano, $C_1$-$C_6$ cyanoalkyl, $C_1$-$C_6$ alkoxy, ($C_1$-$C_6$) tri-alkylsilane ($C_1$-$C_6$) alkyl, amido, aldehydro, $-CO_2H$, $C_1$-$C_6$ ketoalkyl, thio, $C_1$-$C_6$ thioalkyl, ($C_1$-$C_6$) alkylthio, amino, N-amino ($C_1$-$C_6$) alkylcarbonyl, N-amino carbamyl, and N-amino ($C_1$-$C_6$) alkylsulphonyl;
$R'_3$ is chosen from $-CO_2H$ and linear or branched $C_1$-$C_6$ alkyl optionally substituted with at least one substituent chosen from hydroxyl, $C_1$-$C_2$ alkoxy, $C_1$-$C_4$ (poly) hydroxyalkoxy, amino, $C_1$-$C_2$ (di) alkylamino, carboxyl, $C_1$-$C_4$ alkyl carboxylate, sulphonic, $C_1$-$C_4$ alkyl sulphonate, optionally substituted phenyl, and sulphonylamino;
$A_1^-$ is chosen from an organic anion and an inorganic anion;
Z is chosen from: $-NR_3R_4$; and $-OR_5$;
$R_1$, $R_2$, $R_3$, $R_4$, and $R_5$, which are identical or different, are independently selected from:
  $C_1$-$C_6$ alkyls optionally substituted with at least one substituent chosen from $OR_6$, $NR_7R_8$, $-CO_2H$, $C_1$-$C_4$ alkyl carboxylate, sulphonic, $-CONR_7R_8$, $-SO_2NR_7R_8$, 5- or 6-membered heteroaryl, and phenyl wherein said phenyl is optionally substituted with at least one substituent chosen from ($C_1$-$C_4$) alkyl, hydroxyl, $C_1$-$C_2$ alkoxy, amino, ($C_1$-$C_2$)(di) alkylamino and $C_1$-$C_4$ hydroxyalkyl;
  phenyls optionally substituted with at least one substituent chosen from ($C_1$-$C_4$) alkyl, hydroxy ($C_1$-$C_4$)alkyl, hydroxyl, $C_1$-$C_2$ alkoxy, amino, and ($C_1$-$C_2$)(di) alkylamino; and
  5- or 6-membered heteroaryls optionally substituted with at least one substituent chosen from ($C_1$-$C_4$) alkyl and ($C_1$-$C_2$) alkoxy;
$R_3$, $R_4$ and $R_5$ can also be H;
$R_6$, $R_7$ and $R_8$, which are identical or different, are independently selected from:
  H;
  linear or branched $C_1$-$C_4$ alkyl optionally substituted with at least one substituent chosen from hydroxyl, $C_1$-$C_2$ alkoxy, $-CONR_9R_{10}$, $-SO_2R_9$, and phenyl wherein said phenyl is optionally substituted with at least one substituent chosen from ($C_1$-$C_4$) alkyl, hydroxyl, $C_1$-$C_2$ alkoxy, amino, and ($C_1$-$C_2$)(di) alkylamino; and
  phenyls optionally substituted with at least one substituent chosen from ($C_1$-$C_4$) alkyl, hydroxyl, $C_1$-$C_2$ alkoxy, amino, and ($C_1$-$C_2$)(di) alkylamino;
$R_7$ and $R_8$, which are identical or different, can also be chosen from $-C(O)NR_9R_{10}$ and $-SO_2R_9$;
$R_9$ and $R_{10}$, which are identical or different, are independently selected from H and linear or branched $C_1$-$C_4$ alkyl optionally substituted with at least one substituent chosen from hydroxyl and $C_1$-$C_2$ alkoxy;

R₁ and R₂, on the one hand, and R₃ and R₄, on the other hand, can form with the nitrogen atoms to which they are attached a 5- to 7-membered saturated or unsaturated heterocycle whose carbon atoms may be replaced by an oxygen or nitrogen atom, wherein said saturated or unsaturated heterocycle is optionally substituted with at least one substituent chosen from halogen, amino, ($C_1$-$C_4$)(di) alkylamino, (di) hydroxy ($C_1$-$C_4$) alkylamino, hydroxyl, carboxyl, carboxamido, ($C_1$-$C_4$)(di) alkylcarboxamido, ($C_1$-$C_2$) alkoxy, and $C_1$-$C_4$ alkyl wherein said $C_1$-$C_4$ alkyl is optionally substituted with at least one substituent chosen from hydroxyl, amino, ($C_1$-$C_4$)(di) alkylamino, $C_1$-$C_2$ alkoxy, carboxyl, and sulphonyl;

with the proviso that the at least one azo pyrazolinone entity of formula (I) is not chosen from:

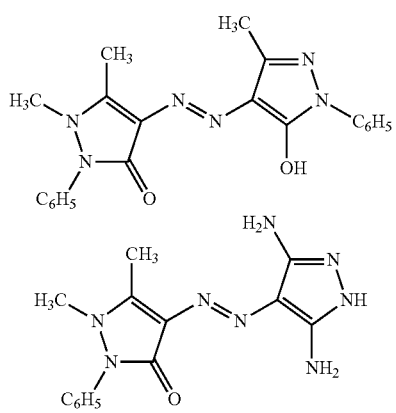

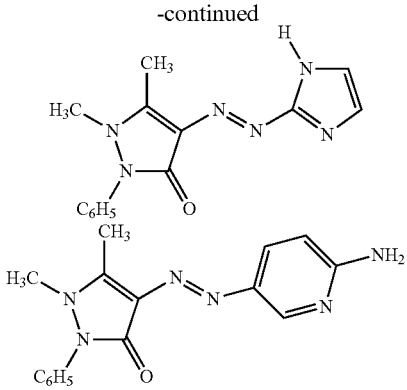

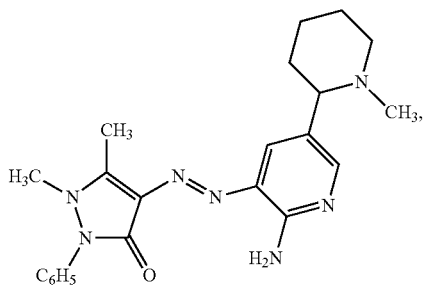

the mesomeric forms, acid addition salts, and solvates thereof, and the at least one second compartment comprises an oxidizing composition.

* * * * *